US012703886B2

(12) United States Patent
Ma et al.

(10) Patent No.: US 12,703,886 B2
(45) Date of Patent: Aug. 11, 2026

(54) NUCLEIC ACID TEST KIT, TEST METHOD, AND USE

(71) Applicant: SHANGHAITECH UNIVERSITY, Shanghai (CN)

(72) Inventors: Peixiang Ma, Shanghai (CN); Xinjie Wang, Shanghai (CN)

(73) Assignee: SHANGHAITECH UNIVERSITY, Shanghai (CN)

( * ) Notice: Subject to any disclaimer, the term of this patent is extended or adjusted under 35 U.S.C. 154(b) by 845 days.

(21) Appl. No.: 17/925,675

(22) PCT Filed: Jul. 16, 2021

(86) PCT No.: PCT/CN2021/106843
§ 371 (c)(1),
(2) Date: Nov. 16, 2022

(87) PCT Pub. No.: WO2021/233480
PCT Pub. Date: Nov. 25, 2021

(65) Prior Publication Data

US 2023/0193408 A1 Jun. 22, 2023

(30) Foreign Application Priority Data

May 19, 2020 (CN) ......................... 202010426283.1

(51) Int. Cl.
*C12Q 1/70* (2006.01)

(52) U.S. Cl.
CPC .................................... *C12Q 1/701* (2013.01)

(58) Field of Classification Search
None
See application file for complete search history.

(56) References Cited

FOREIGN PATENT DOCUMENTS

| | | | | |
|---|---|---|---|---|
| CN | 2784420 Y | | 5/2006 | |
| CN | 106868220 A | | 6/2017 | |
| CN | 110184329 A | | 8/2019 | |
| CN | 110551846 A | | 12/2019 | |
| CN | 110799525 A | | 2/2020 | |
| WO | WO-2018195545 A2 | | 10/2018 | |
| WO | WO-2020028729 A1 | * | 2/2020 | ............. C12Q 1/683 |

OTHER PUBLICATIONS

Ma et al. (Adv. Sci. 2020, 7, 2001300, 9 pages) (Year: 2020).*
Chen et al. (Science 360, 436-439 (2018)) (Year: 2018).*
Ahn et al. (Sci Rep 9, 13911 (2019). https://doi.org/10.1038/s41598-019-50423-6). (Year: 2019).*
Gong et al. (Bioactive Materials 6 (2021) 4580-4590) (Year: 2021).*
Gootenberg et al. (Science 360, 439-444 (2018); including supplemental materials) (Year: 2018).*
Oct. 20, 2021 International Search Report issued in International Patent Application No. PCT/CN2021/106843.
Oct. 20, 2021 Written Opinion of the International Searching Authority issued in International Patent Application No. PCT/CN2021/106843.
R, B., et al., CRISPR provides acquired resistance against viruses in prokaryotes. Science (New York, N.Y.), 2007. 315(5819): p. 1709-12.—(2007).
La, M. and S. EJ, CRISPR interference limits horizontal gene transfer in staphylococci by targeting DNA. Science (New York, N.Y.), 2008. 322(5909): p. 1843-5.—(2008).
B, Z., et al., Cpf1 is a single RNA-guided endonuclease of a class 2 CRISPR-Cas system. Cell, 2015. 163(3): p. 759-71.—(2015).
I, F., et al., The CRISPR-associated DNA-cleaving enzyme Cpf1 also processes precursor CRISPR RNA. Nature, 2016. 532(7600): p. 517-21.—(2016).
JS, C., et al., CRISPR-Cpf1 target binding unleashes indiscriminate single-stranded DNase activity. Science (New York, N.Y.), 2018. 360(6387): p. 436-439.—(2018).
González, JM. et al. A comparative sequence analysis to revise the current taxonomy of the family Coronaviridae. Arch Virol. 2003 ;148(11):p. 2207-35.—(2003).
Ksiazek, TG.et al., A novel coronavirus associated with severe acute respiratory syndrome. N Engl J Med, 2003, 348(20): p. 1953-1966,(2003).
Zaki, AM.et al., Isolation of a Novel Coronavirus From a Man With Pneumonia in Saudi Arabia. N Engl J Med, 2012, 367(19): p. 1814-20.—(2012).
O, P., et al., DNA detection using recombination proteins. PLoS biology, 2006. 4(7): p. e204.—(2006).
Xinjie Wang et al. “Rapid and sensitive detection of COVID-19 using CRISPR/Cas12a-based detection with naked eye readout, CRISPR/Cas12a-NER” Science Bulletin, vol. 65, No. 17, pp. 1436-1439 (May 5, 2020).
Woo-Chan Ann et al.“In vivo genome editing using the Cpf1 ortholog derived from Eubacterium eligens” Scientific reports, vol. 9, pp. 1-7, (Sep. 26, 2019).

(Continued)

*Primary Examiner* — Juliet C Switzer
(74) *Attorney, Agent, or Firm* — Harness, Dickey & Pierce, P.L.C.

(57) ABSTRACT

Disclosed is a nucleic acid test kit, comprising a Cpf1 test system, said Cpf1 test system comprising: a guide RNA, a Cpf1 protein, a nucleic acid probe, and a manganese ion-containing solution. Also provided is a mutated Cpf1 protein and a nucleic acid test kit containing the mutated Cpf1 protein. Also provided is a crRNA for testing coronavirus nucleic acid, and a nucleic acid test kit containing said crRNA. Further provided is a use of the nucleic acid test kit, and a test method for the nucleic acid. When the nucleic acid test kit, mutated Cpf1 protein, or crRNA of the present invention are used for nucleic acid testing (for example, testing the nucleic acid of a SARS-related coronavirus or MERS coronavirus), the signal strength during the test is substantially enhanced, and the test time is thus reduced and the test efficiency improved. In addition, the sensitivity, specificity, and accuracy are high, the test is visual, the cost is low, the operation is simple and convenient, and no large-scale complex t equipment is required.

20 Claims, 18 Drawing Sheets

Specification includes a Sequence Listing.

(56) References Cited

OTHER PUBLICATIONS

Sep. 17, 2020 Office action on Chinese application No. 202010426283.1.

Xie, X., et al. Research Progress on the 2019 Novel Coronavirus. Virologica Sinica, 36(3), 493-501. (Mar. 2020).

* cited by examiner a b c a b

MERS-E-DNA

MERS-Orf1-DNA c a

SARS-Orf1-RNA b

MERS-E-RNA

MERS-Orf1-RNA c a b

SARS-Crmix MERS-Crmix a b a b c

NUCLEIC ACID TEST KIT, TEST METHOD, AND USE

CROSS-REFERENCE TO RELATED APPLICATIONS

The present application is a U.S. National Phase Application under 35 U.S.C. 371 of International Application No. PCT/CN2021/106843, filed on Jul. 16, 2021, which claims the benefit of Chinese patent application 2020104262831 filed on May 19, 2020. The entire disclosures of the aforementioned applications are incorporated herein by reference.

SEQUENCE LISTING

This application contains references to amino acid sequences and/or nucleic acid sequences which have been submitted concurrently herewith as the sequence listing text file entitled "17424-145-NP_English_Sequence_Listing", file size 154 KiloBytes (KB), created on Nov. 14, 2022. The aforementioned sequence listing is hereby incorporated by reference in its entirety pursuant to 37 C.F.R. § 1.52(e)(5).

TECHNICAL FIELD

The present invention belongs to the technical field of biology, and particularly relates to a nucleic acid detection kit including a Cpf1 detection system and a detection method. The present invention further relates to use of the nucleic acid detection kit, in particular to use in rapid detection of nucleic acids of a severe acute respiratory syndrome-associated coronavirus and a Middle East respiratory syndrome coronavirus.

BACKGROUND

Coronaviruses belong to the genus Coronavirus of the family Coronaviridae in the order Nidovirales [6]. A mature coronavirus has an envelope on the surface thereof, the envelope is covered with spikes having spherical ends, so the entire spikes are petal-shaped or pear-shaped, and there is a wide gap between the spikes. Coronavirus particles are named for the regularly arranged crown-like envelope spikes under an electron microscope. Members of the Coronavirus genus have caused several outbreaks, such as Severe Acute Respiratory Syndrome (abbreviated as SARS) in 2002 and Middle East respiratory syndrome coronavirus (MERS-CoV) in 2012. The first SARS case was discovered in Shunde city, Guangdong province in 2002, and then the virus rapidly spread to more than 30 countries and regions including Hong Kong, Vietnam, Singapore, and Canada, with over 8,000 infections and a mortality rate of about 10% [7]. MERS-CoV was first identified in 2012 [8]. From September, 2012 to January, 2020, WHO had reported a total of 2,506 laboratory-confirmed cases, of which 862 cases were dead (at a mortality rate of approximately 34.3%). Unlike the SARS epidemic that broke out in 2002, which was effectively controlled, there is ongoing spreading and infection of MERS-CoV to date, and two confirmed MERS infectors were still reported by WHO in January, 2020. The two disease outbreaks have had a tremendous impact on social life and the economy, and there are currently no effective vaccines and therapeutic drugs for these two highly contagious coronaviruses. Timely diagnosis and isolation are effective ways to control the outbreak of the disease.

Rapid and efficient nucleic acid detection is an effective method for clinical prevention and control of viral diseases.

Most of the existing detection methods for viral diseases are based on a nucleic acid detection. In the guidance document of laboratory diagnostic procedures for Severe Acute Respiratory Syndrome (abbreviated as SARS) and Middle East respiratory syndrome coronavirus (MERS-CoV) issued by WHO, real-time reverse transcription PCR (rRT-PCR) is recommended for detection and diagnosis of the viruses. The detection of viral nucleic acids by rRT-PCR is mainly limited by expensive PCR experimental equipment, the number of personnel able to perform a skilled and stable operation, long detection time, etc. Immunological detection methods are also important means for virus detection, such as double-antibody sandwich ELISA, colloidal gold immunochromatography test paper, and the similar methods. The immunological examination is susceptible to the course of the disease and is easy to miss the diagnosis because there are few antibodies in the patient in the early stage and the corresponding antibody will be produced after a certain period; and a rehabilitated patient after illness may carry such an antibody, which may easily lead to false positive in immunodiagnostics. To effectively control the spread of viral infectious diseases, it is necessary to establish a simple, rapid, and specific novel detection method.

CRISPR-Cas (Clustered regularly interspaced short palindromic repeats, CRISPRs) is an adaptive immune system in bacteria, in which a Cas protein targets and degrades a foreign nucleic acid by an RNA-guided nuclease [1,2]. CRISPR-Cpf1 (Cpf1) belongs to the second family of Cas enzymes and is used for guiding an RNA to direct a double-stranded DNA for cleavage by a single RuvC catalytic domain. Cpf1 enzymes recognize Thymine (T) nucleotide-rich protospacer adjacent motifs (PAMs) [3], catalyze their own guide-CRISPR RNA (crRNA) to mature [4], and specifically recognize and cleave a complementary paired double-stranded DNA (dsDNA) [3]. When the CRISPR/Cpf1 protein recognizes and cleaves the target double-stranded DNA in a sequence-specific manner, it will induce a strong non-specific single-stranded DNA (ssDNA) trans-cleavage activity [5]. Cpf1 has endonuclease activity, and the ligand ion of an endonuclease is usually a magnesium ion. The existing Cpf1-based nucleic acid detection still has low signal intensity, which results in the defects of long detection time and low detection efficiency of low concentration samples in the actual detection. There is therefore a need to further enhance the intensity of the detection signal to meet the needs of the actual detection. In addition, there is an urgent need to improve the sensitivity, specificity, and stability in detecting nucleic acids.

Content of the Present Invention

A technical problem to be solved by the present invention is to overcome the defects such as too high cost, a long detection time, low detection efficiency, insufficient specificity and sensitivity in nucleic acid detection in the prior art, and provided herein is a nucleic acid detection kit, a mutated Cpf1 protein, a crRNA, a detection method, and usage. When the nucleic acid detection kit, mutated Cpf1 protein, or crRNA of the present invention are used for nucleic acid detection (for example, detecting the nucleic acid of a SARS-associated coronavirus or MERS coronavirus), the signal intensity during the detection is substantially enhanced, and thus the detection time is reduced and the detection efficiency is improved. In addition, the sensitivity, specificity, and accuracy are high, the detection is visual, the cost is low, the operation is simple, and no large-scale complex detection equipment is required.

Cpf1 has endonuclease activity, and the ligand ion of an endonuclease is usually a magnesium ion in the art. However, the present inventors have found for the first time that a manganese ion can promote the ability of Cpf1 to cleave a nucleic acid probe (e.g., a single-stranded DNA probe), and thus improve the signal intensity of the Cpf1 detection, so that the Cpf1-mediated in vitro detection signal can be enhanced to reduce the detection time and improve the detection efficiency. In addition, through a large number of experiments in the present invention, it is unexpectedly found that when certain Cpf1 proteins are specifically mutated, the signal intensity during nucleic acid detection can also be significantly improved. The present inventors have also adopted the Cpf1 fluorescence method for the first time to detect SARS-related coronavirus and MERS coronavirus and developed a crRNA through a large number of experiments, which can be used for detecting these viruses with very high sensitivity, specificity, and accuracy.

To solve the aforementioned technical problem, in a first aspect, the present invention provides a nucleic acid detection kit including a Cpf1 detection system, said Cpf1 detection system including a guide RNA, a Cpf1 protein, a nucleic acid probe, and a manganese ion-containing solution.

Preferably, the manganese ion-containing solution is a solution of manganese sulfate, manganese chloride, or manganese acetate.

Preferably, the nucleic acid probe is a single-stranded DNA probe, which preferably includes a fluorescent label, more preferably has a fluorescent group and a fluorescence quenching group at its 5' and 3' terminals, respectively, and further more preferably has a fluorescent group at its 5' terminal and a fluorescence quenching group at its 3' terminal.

The fluorescent group may be conventional in the art, for example, 6-FAM, TET, CY3, CY5, or ROX. The fluorescence quenching group may be conventional in the art, for example, BHQ1, BHQ2, or BHQ3. The sequence of the single-stranded DNA probe is prepared according to conventional methods in the art and may be, for example, TTTATTT.

Preferably, the Cpf1 protein is selected from one or more of AsCpf1 (*Acidaminococcus* sp. BV3L6), BbCpf1 (*Beauveria bassiana* KA00251), BoCpf1 (Bacteroidetes oral), FnCpf1 (*Francisella novicida* U112), HkCpf1 (*Helcococcus kunzii*), Lb4Cpf1 (*Lachnospiraceae bacterium* MC2017), Lb5Cpf1 (*Lachnospiraceae bacterium* NC2008), LbCpf1 (*Lachnospiraceae bacterium* ND2006), Oscpf1 (*Oribacterium* sp.), and TsCpf1 (*Thiomicrospira* sp. XS5).

Preferably, the Cpf1 protein is a codon-optimized Cpf1 protein, the nucleotide sequence of which is preferably as shown in one or more of SEQ ID NOs: 14-23.

Preferably, the Cpf1 protein is a mutated Cpf1 protein, which preferably has an amino acid sequence with 98%, preferably more than 99% sequence homology to a native Cpf1 protein. More preferably, the sequence of the mutated Cpf1 protein includes a sequence in which one or more sites of K180, E184, N607 and K613 as shown in SEQ ID NO: 55 are mutated to R, or one or more sites of T148, T152, G532 and K538 as shown in SEQ ID NO: 54 are mutated to R. For example, the sequence may be a sequence in which E184 and N607 as shown in SEQ ID NO: 55 are mutated to R, a sequence in which E184, N607 and K613 as shown in SEQ ID NO: 55 are mutated to R, a sequence in which K180, E184, N607 and K613 as shown in SEQ ID NO: 55 are mutated to R, a sequence in which T152 and G532 as shown in SEQ ID NO: 54 are mutated to R, a sequence in which T152, G532 and K538 as shown in SEQ ID NO: 54 are mutated to R, and a sequence in which T148, T152, G532 and K538 as shown in SEQ ID NO: 54 are mutated to R. Further more preferably, the nucleotide sequence of the mutated Cpf1 protein is as shown in SEQ ID NOs: 30-41.

Preferably, the guide RNA is an RNA that guides the Cpf1 protein to specifically bind to the nucleic acid, preferably a crRNA; the crRNA is preferably a crRNA for detecting a viral nucleic acid; more preferably a crRNA for detecting a SARS-associated coronavirus or a MERS-CoV virus; and the SARS-associated coronavirus is preferably SARS-CoV (severe acute respiratory syndrome coronavirus) or SARS-CoV-2 (severe acute respiratory syndrome coronavirus 2). More preferably, the crRNA is a crRNA for detecting an orf1ab gene of the SARS-CoV virus, a crRNA for detecting an orf1a gene of the MERS-CoV virus, a crRNA for detecting an upE gene of the MERS-CoV virus, a crRNA for detecting a E gene of the SARS-CoV-2 virus, a crRNA for detecting an S gene of the SARS-CoV-2 virus, a crRNA for detecting an M gene of the SARS-CoV-2 virus and/or a crRNA for detecting an N gene of the SARS-CoV-2 virus; the nucleotide sequence of the orf1ab gene is as shown in SEQ ID NO: 11, the nucleotide sequence of the orf1a gene is as shown in SEQ ID NO: 12, the nucleotide sequence of the upE gene is as shown in SEQ ID NO: 13, and the nucleotide sequence of the E gene is as shown in SEQ ID NO: 46; the nucleotide sequence of the SARS-CoV-2-S gene is as shown in SEQ ID NO: 79; the nucleotide sequence of the SARS-CoV-2-M gene is as shown in SEQ ID NO: 80; and the nucleotide sequence of the SARS-CoV-2-N gene is as shown in SEQ ID NO: 81. Further more preferably, the nucleotide sequence of the crRNA is preferably as shown in one or more of SEQ ID NOs: 1-10, SEQ ID NO: 47, SEQ ID NO: 48 and SEQ ID NO: 53, and SEQ ID NOs: 56-72.

Preferably, the manganese ion in the manganese ion-containing solution has a concentration of 5-600 mM, e.g., 6, 7, 8, 9, 10, 20, 30, 40, 50, 60, 70, 80, 90, 100, 150, 200, 250, 300, 350, 400, 450, or 500 mM, etc. The point values listed are examples only and are not intended to be limiting, and it should be understood that any point value within this concentration range can be freely combined, and thus any combination of concentration ranges is intended to be within the scope of the present invention. For example, the concentration range such as 5-50, 5-100, 5-200, 5-300, 5-400, 5-500, 100-200, 100-300, and 200-300 should be within the scope of the present invention. In experiments, the inventors have found that working concentrations of the manganese ion within 0.5-60 mM are all effective, and the kit generally contains a 10-fold mixed stock solution, so that the concentration of the stock solution is 5-600 mM. In a preferred embodiment of the present invention, the manganese ion in the manganese ion-containing solution as used has a concentration of 100 mM.

Preferably, the nucleic acid probe has a concentration of 1-100 μmol/μL, and preferably 25 μmol/μL.

Preferably, the Cpf1 protein has a concentration of 20-1,000 ng/μL, and preferably 200 ng/μL.

Preferably, the guide RNA has a concentration of 0.1-50 μM, and preferably 1 μm.

Preferably, the nucleic acid detection kit further includes an RNA enzyme inhibitor and a buffer; and preferably the RNA enzyme inhibitor has a concentration of 10-200 U/μL, and preferably 40 U/μL.

Preferably, the buffer preferably includes NaCl, Tris, and BSA, and preferably has a pH of 7.9. In a preferred embodiment of the present invention, the buffer as used is a 10× buffer with a composition of 1,000 mM NaCl, 500 mM Tris, and 1,000 μg/mL BSA, pH 7.9.

To solve the aforementioned technical problem, in a second aspect, the present invention provides a mutated Cpf1 protein with the sequence including a sequence in which one or more sites of K180, E184, N607 and K613 as shown in SEQ ID NO: 55 are mutated to R; alternatively, the sequence includes a sequence in which one or more sites of T148, T152, G532 and K538 as shown in SEQ ID NO: 54 are mutated to R.

Preferably, the sequence of the mutated Cpf1 protein includes a sequence in which E184 and N607 as shown in SEQ ID NO: 55 are mutated to R.

Preferably, the sequence of the mutated Cpf1 protein includes a sequence in which E184, N607 and K613 as shown in SEQ ID NO: 55 are mutated to R.

Preferably, the sequence of the mutated Cpf1 protein includes a sequence in which K180, E184, N607 and K613 as shown in SEQ ID NO: 55 are mutated to R.

Preferably, the sequence of the mutated Cpf1 protein includes a sequence in which T152 and G532 as shown in SEQ ID NO: 54 are mutated to R.

Preferably, the sequence of the mutated Cpf1 protein includes a sequence in which T152, G532 and K538 as shown in SEQ ID NO: 54 are mutated to R.

Preferably, the sequence of the mutated Cpf1 protein includes a sequence in which T148, T152, G532 and K538 as shown in SEQ ID NO: 54 are mutated to R.

More preferably, the nucleotide sequence of the mutated Cpf1 protein is as shown in SEQ ID NOs: 30-41.

To solve the aforementioned technical problem, in a third aspect, the present invention provides a nucleic acid detection kit including a Cpf1 detection system, said Cpf1 detection system including a guide RNA, a nucleic acid probe, and a mutated Cpf1 protein according to the second aspect of the present invention.

Preferably, the guide RNA is an RNA that guides the Cpf1 protein to specifically bind to the nucleic acid, preferably a crRNA; the crRNA is preferably a crRNA for detecting a viral nucleic acid; more preferably a crRNA for detecting a SARS-associated coronavirus or a MERS-CoV virus; the SARS-associated coronavirus is preferably SARS-CoV or SARS-CoV-2; the crRNA is a crRNA for detecting an orf1ab gene of the SARS-CoV virus, a crRNA for detecting an orf1a gene of the MERS-CoV virus, a crRNA for detecting an upE gene of the MERS-CoV virus, a crRNA for detecting a E gene of the SARS-CoV-2 virus, a crRNA for detecting an S gene of the SARS-CoV-2 virus, a crRNA for detecting an M gene of the SARS-CoV-2 virus and/or a crRNA for detecting an N gene of the SARS-CoV-2 virus; the nucleotide sequence of the orf1ab gene is as shown in SEQ ID NO: 11, the nucleotide sequence of the orf1a gene is as shown in SEQ ID NO: 12, the nucleotide sequence of the upE gene is as shown in SEQ ID NO: 13, the nucleotide sequence of the E gene is as shown in SEQ ID NO: 46, and the nucleotide sequence of the SARS-CoV-2-S gene is as shown in SEQ ID NO: 79; the nucleotide sequence of the SARS-CoV-2-M gene is as shown in SEQ ID NO: 80; the nucleotide sequence of the SARS-CoV-2-N gene is as shown in SEQ ID NO: 81; more preferably, the nucleotide sequence of crRNA is as shown in one or more of SEQ ID NOs: 1-10, SEQ ID NO: 47, SEQ ID NO: 48 and SEQ ID NO: 53, and SEQ ID NOs: 56-72;

preferably, the nucleic acid probe is a single-stranded DNA probe, which preferably includes a fluorescent label, more preferably has a fluorescent group and a fluorescence quenching group at its two terminals, respectively, and further more preferably has a fluorescent group at a 5' terminal and a fluorescence quenching group at a 3' terminal. The fluorescent group may be conventional in the art, for example, 6-FAM, TET, CY3, CY5, or ROX. The fluorescence quenching group may be conventional in the art, for example, BHQ1, BHQ2, or BHQ3. The single-stranded DNA probe can be prepared according to conventional methods in the art, and its sequence may be, for example, TTTATTT.

Preferably, the guide RNA has a concentration of 0.1-50 μM, and preferably 1 μm.

Preferably, the mutated Cpf1 protein has a concentration of 20-1,000 ng/μL, and preferably 200 ng/μL.

Preferably, the nucleic acid probe has a concentration of 1-100 μmol/μL, and preferably 25 μmol/μL.

Preferably, the nucleic acid detection kit further includes a metal ion-containing solution such as a magnesium ion-containing solution and a manganese ion-containing solution; and preferably, the metal ion in the solution has a concentration of 5-600 mM, e.g., 6, 7, 8, 9, 10, 20, 30, 40, 50, 60, 70, 80, 90, 100, 150, 200, 250, 300, 350, 400, 450 or 500 mM, etc. The point values listed are examples only and are not intended to be limiting, and it should be understood that any point value within this concentration range can be freely combined, and thus any combination of concentration ranges is intended to be within the scope of the present invention. For example, the concentration range such as 5-50, 5-100, 5-200, 5-300, 5-400, 5-500, 100-200, 100-300, and 200-300 should be within the scope of the present invention. In experiments, the inventors have found that working concentrations of the metal ion within 0.5-60 mM are all effective, and the kit generally contains a 10-fold mixed stock solution, so that the concentration of the stock solution is 5-600 mM. In a preferred embodiment of the present invention, the metal ion in the metal ion-containing solution used has a concentration of 100 mM.

Preferably, the nucleic acid detection kit further includes an RNA enzyme inhibitor and a buffer; preferably the RNA enzyme inhibitor has a concentration of 10-200 U/μL, and preferably 40 U/μL.

Preferably, the buffer includes NaCl, Tris, and BSA, and preferably has a pH of 7.9. In a preferred embodiment of the present invention, the buffer as used is a 10× buffer with the composition of 1,000 mM NaCl, 500 mM Tris, and 1,000 μg/mL BSA, pH 7.9.

To solve the aforementioned technical problem, in the fourth aspect, the present invention provides a crRNA for detecting nucleic acid of a coronavirus, wherein the crRNA is a crRNA for detecting an orf1ab gene of the SARS-CoV virus, a crRNA for detecting an orf1a gene of the MERS-CoV virus, a crRNA for detecting an upE gene of the MERS-CoV virus, a crRNA for detecting a E gene of the SARS-CoV-2 virus, a crRNA for detecting an S gene of the SARS-CoV-2 virus, a crRNA for detecting an M gene of the SARS-CoV-2 virus and/or a crRNA for detecting an N gene of the SARS-CoV-2 virus; the nucleotide sequence of the orf1ab gene is as shown in SEQ ID NO: 11, the nucleotide sequence of the orf1a gene is as shown in SEQ ID NO: 12, the nucleotide sequence of the upE gene is as shown in SEQ ID NO: 13, the nucleotide sequence of the E gene is as shown in SEQ ID NO: 46, and the nucleotide sequence of the SARS-CoV-2-S gene is as shown in SEQ ID NO: 79; the nucleotide sequence of the SARS-CoV-2-M gene is as shown in SEQ ID NO: 80; and the nucleotide sequence of the SARS-CoV-2-N gene is as shown in SEQ ID NO: 81.

Preferably, the nucleotide sequence of the crRNA for detecting the orf1ab gene of the SARS-CoV virus is as shown in one or more of SEQ ID NOs: 1-3.

Preferably, the nucleotide sequence of the crRNA for detecting the orf1a gene of the SARS-CoV virus is as shown in one or more of SEQ ID NOs: 4-7.

Preferably, the nucleotide sequence of the crRNA for detecting the upE gene of the SARS-CoV virus is as shown in one or more of SEQ ID NOs: 8-10.

Preferably, the nucleotide sequence of the crRNA for detecting the E gene of the SARS-CoV-2 virus is as shown in one or more of SEQ ID NO: 47, SEQ ID NO: 48, and SEQ ID NO: 53.

Preferably, the nucleotide sequence of the crRNA for detecting the S gene of the SARS-CoV-2 virus is as shown in one or more of SEQ ID NOs: 56-63.

Preferably, the nucleotide sequence of the crRNA for detecting the M gene of the SARS-CoV-2 virus is as shown in one or more of SEQ ID NOs: 64-68.

Preferably, the nucleotide sequence of the crRNA for detecting the N gene of the SARS-CoV-2 virus is as shown in one or more of SEQ ID NOs: 69-72.

In a preferred embodiment of the present invention, a process for preparing the crRNA includes the steps of designing a 44 bp crRNA by searching for a targeting sequence containing a cpf1 recognition sequence (PAM) TTTN for the orf1ab gene of the nucleic acid of a SARS virus with the sequence of SEQ ID NO: 11; designing a 44 bp crRNA by searching for a targeting sequence containing the cpf1 recognition sequence (PAM) TTTN for the upE gene of the nucleic acid of a MERS virus with the sequence of SEQ ID NO: 12; designing a 44 bp crRNA by searching for a targeting sequence containing the cpf1 recognition sequence (PAM) TTTN for the Orf1 gene of the nucleic acid of the MERS virus with the sequence of SEQ ID NO: 13; designing a 44 bp crRNA by searching for a targeting sequence containing the cpf1 recognition sequence (PAM) TTTN for the E gene of the nucleic acid of a SARS-CoV-2 virus with the sequence of SEQ ID NO: 46; designing a 44 bp crRNA by searching for a targeting sequence containing the cpf1 recognition sequence (PAM) TTTN for the S gene of the nucleic acid of the SARS-CoV-2 virus with the sequence of SEQ ID NO: 79; designing a 44 bp crRNA by searching for a targeting sequence containing the cpf1 recognition sequence (PAM) TTTN for the M gene of the nucleic acid of the SARS-CoV-2 virus with the sequence of SEQ ID NO: 80; and designing a 44 bp crRNA by searching for a targeting sequence containing the cpf1 recognition sequence (PAM) TTTN for the N gene of the nucleic acid of the SARS-CoV-2 virus with the sequence of SEQ ID NO: 81. After the design is complete, the crRNA is prepared. The crRNA can be constructed into a vector pUC57-T7-crRNA to obtain a target crRNA by in vitro transcription, or can be synthesized into an RNA sequence by a company.

To solve the aforementioned technical problem, in a fifth aspect, the present invention provides a nucleic acid detection kit including a Cpf1 detection system, said Cpf1 detection system including a crRNA, a Cpf1 protein, and a nucleic acid probe according to the fourth aspect of the present invention.

Preferably, the Cpf1 protein is selected from one or more of AsCpf1 (*Acidaminococcus* sp. BV3L6), BbCpf1 (*Beauveria bassiana* KA00251), BoCpf1 (Bacteroidetes oral), FnCpf1 (*Francisella novicida* U112), HkCpf1 (*Helcococcus kunzii*), Lb4Cpf1 (*Lachnospiraceae bacterium* MC2017), Lb5Cpf1 (*Lachnospiraceae bacterium* NC2008), LbCpf1 (*Lachnospiraceae bacterium* ND2006), Oscpf1 (*Oribacterium* sp.), and TsCpf1 (*Thiomicrospira* sp. XS5), or those having 98%, preferably more than 99% sequence homology to the amino acid sequence thereof.

Preferably, the Cpf1 protein is a codon-optimized Cpf1 protein, the nucleotide sequence of which is preferably as shown in one or more of SEQ ID NOs: 14-23.

Preferably, the Cpf1 protein is a mutated Cpf1 protein, which preferably has an amino acid sequence with 98%, preferably more than 99% sequence homology to a native Cpf1 protein. More preferably, the sequence of the mutated Cpf1 protein includes a sequence in which one or more sites of K180, E184, N607 and K613 as shown in SEQ ID NO: 55 are mutated to R, or one or more sites of T148, T152, G532 and K538 as shown in SEQ ID NO: 54 are mutated to R. For example, the sequence may be a sequence in which E184 and N607 as shown in SEQ ID NO: 55 are mutated to R, a sequence in which E184, N607 and K613 as shown in SEQ ID NO: 55 are mutated to R, a sequence in which K180, E184, N607 and K613 as shown in SEQ ID NO: 55 are mutated to R, a sequence in which T152 and G532 as shown in SEQ ID NO: 54 are mutated to R, a sequence in which T152, G532 and K538 as shown in SEQ ID NO: 54 are mutated to R, and a sequence in which T148, T152, G532 and K538 as shown in SEQ ID NO: 54 are mutated to R. Further more preferably, the nucleotide sequence of the mutated Cpf1 protein is as shown in SEQ ID NOs: 30-41.

Preferably, the nucleic acid probe is a single-stranded DNA probe, which preferably includes a fluorescent label, more preferably has a fluorescent group and a fluorescence quenching group at its two terminals, respectively, and further more preferably has a fluorescent group at a 5' terminal and a fluorescence quenching group at a 3' terminal. The fluorescent group may be conventional in the art, for example, 6-FAM, TET, CY3, CY5, or ROX. The fluorescence quenching group may be conventional in the art, for example, BHQ1, BHQ2, or BHQ3. The single-stranded DNA probe can be prepared according to conventional methods in the art, and its sequence may be, for example, TTTATTT.

Preferably, the crRNA has a concentration of 0.1-50 μM, and preferably 1 μM.

Preferably, the Cpf1 protein has a concentration of 20-1, 000 ng/μL, and preferably 200 ng/μL.

Preferably, the nucleic acid probe has a concentration of 1-100 μmol/μL, and preferably 25 μmol/μL.

Preferably, the nucleic acid detection kit further includes a metal ion-containing solution such as a magnesium ion-containing solution and a manganese ion-containing solution; and preferably, the metal ion in the solution has a concentration of 5-600 mM, e.g., 6, 7, 8, 9, 10, 20, 30, 40, 50, 60, 70, 80, 90, 100, 150, 200, 250, 300, 350, 400, 450 or 500 mM, etc. The point values listed are examples only and are not intended to be limiting, and it should be understood that any point value within this concentration range can be freely combined, and thus any combination of concentration ranges is intended to be within the scope of the present invention. For example, the concentration range such as 5-50, 5-100, 5-200, 5-300, 5-400, 5-500, 100-200, 100-300, and 200-300 should be within the scope of the present invention. In experiments, the inventors have found that working concentrations of the metal ion within 0.5-60 mM are all effective, and the kit generally contains a 10-fold mixed stock solution, so that a concentration of the stock solution is 5-600 mM. In a preferred embodiment of the present invention, the metal ion in the metal ion-containing solution used has a concentration of 100 mM.

Preferably, the nucleic acid detection kit further includes an RNA enzyme inhibitor and a buffer; and preferably the RNA enzyme inhibitor has a concentration of 10-200 U/μL, and preferably 40 U/μL.

Preferably, the buffer includes NaCl, Tris, and BSA, and preferably has a pH of 7.9. In a preferred embodiment of the present invention, the buffer as used is a 10× buffer consisting of 1,000 mM NaCl, 500 mM Tris, and 1,000 μg/mL BSA, pH 7.9.

To solve the aforementioned technical problem, in a sixth aspect, the present invention provides a method for detecting a nucleic acid by using the Cpf1 detection system described in the nucleic acid detection kit according to the first, third, and fifth aspects of the present invention.

Preferably, the nucleic acid in a sample to be tested is released by using a nucleic acid rapid release reagent.

Preferably, the nucleic acid is obtained by amplifying the nucleic acid in a sample to be tested, preferably by RT-RPA. The time of amplification is preferably 25±5 min, and/or the temperature of amplification is preferably 39±5° C., and/or the primers for amplification are preferably as shown in SEQ ID NOs: 24-29, SEQ ID NOs: 44-45, and SEQ ID NOs: 73-78.

Preferably, the Cpf1 detection system has a reaction temperature of 37±5° C.

Preferably, the Cpf1 detection system has a reaction time of 25±5 min.

Preferably, the method further includes the step of reading a result, preferably by a microplate reader or with naked eyes under a fluorescent lamp.

In a preferred embodiment of the present invention, the detecting method includes the following steps:

step a: using a nucleic acid rapid release reagent to inactivate a sample virus and release the nucleic acid in the sample to be tested; and step b: amplifying nucleic acids in the sample to be tested by using isothermal amplification primers: adding the products obtained in step a into an RT-RPA isothermal amplification system with specific primers SEQ ID NO: 24 and SEQ ID NO: 25 for orf1ab gene fragments from the nucleic acid of a SARS virus, or specific primers SEQ ID NO: 26 and SEQ ID NO: 27 for upE gene fragments from the nucleic acid of a MERS virus, or specific primers SEQ ID NO: 28 and SEQ ID NO: 29 for upE gene fragments from the nucleic acid of the MERS virus, or specific primers SEQ ID NO: 44 and SEQ ID NO: 45 for E gene fragments from a SARS-CoV-2 virus, or specific primers SEQ ID NO: 73 and SEQ ID NO: 74 for S gene fragments from the SARS-CoV-2 virus, or specific primers of SEQ ID NO: 75 and SEQ ID NO: 76 for M gene fragments from the SARS-CoV-2 virus, or specific primers SEQ ID NO: 77 and SEQ ID NO: 78 for N gene fragments from the SARS-CoV-2 virus, and reacting at 37° C. for 30 min to amplify a specific product;

step c: when the Cpf1 detection system is used for identifying and cutting the orf1ab of the nucleic acid of the SARS virus or the upE gene fragment of the nucleic acid of the MERS virus or the Orf1 gene fragment of the nucleic acid of the MERS virus or the E gene fragment of the SARS-CoV-2 virus or the S gene fragment of the SARS-CoV-2 virus or the M gene fragment of the SARS-CoV-2 virus or the N gene fragment of the SARS-CoV-2 virus: adding the product obtained in step b into the Cpf1 detection system and reacting at 37° C. for 25 min; and step d: directly detecting and interpreting whether the viral nucleic acid exists in the sample to be tested by a fluorescence microplate reader or with naked eyes under a fluorescent lamp.

To solve the aforementioned technical problem, in a seventh aspect, the present invention provides use of the nucleic acid detection kit according to the first, third, and fifth aspects of the present invention, the mutated Cpf1 protein according to the second aspect of the present invention, or the crRNA according to the fourth aspect of the present invention in detecting a nucleic acid, preferably a viral nucleic acid, or in preparation of a reagent for detecting a nucleic acid, preferably a viral nucleic acid.

Preferably, the virus is a SARS-associated coronavirus or a MERS-CoV virus; and the SARS-associated coronavirus is preferably SARS-CoV or SARS-CoV-2.

The nucleic acid detection kit for rapid detection of the nucleic acids of SARS and MERS viruses as provided by the present invention can be subjected to fluorescence detection by a microplate reader and can also be subjected to fluorescence detection with naked eyes. In the nucleic acid probe (e.g. ssDNA FQ reporter) of the present invention, when the fluorescence detection is performed by a microplate reader, the detection excitation light is set to 485 nm-520 nm; and when direct detection is performed with naked eyes, a light emitter producing a light source with a wavelength of 485 nm is selected for the detection.

In the present invention, generally, the clinical sample may be subjected to a virus inactivation treatment to release the nucleic acid from the sample to be tested. Viral RNAs can be reverse-transcribed (RT) to obtain DNAs under isothermal conditions, which can be subjected to recombinase polymerase amplification (RPA) [9]. When the fluorescent detection is used, the presence of the viral nucleic acid in the Cpf1 detection system results in the specific activation of the endonuclease activity of the Cpf1 protein mediated by the specific crRNA. The activated Cpf1 protein cleaves the ssDNA FQ reporter labeled with a fluorescent group and a fluorescence quenching group, thereby releasing the activated fluorescent group, and fluorescence reads can be detected by a microplate reader or a green reaction is visible to the naked eyes. Accordingly, when no viral nucleic acid is present in the sample to be tested, there will be no fluorescence reads or no visible green reaction.

In the present invention, the nucleic acid probe may also be generally referred to as a fluorescence-quenched single-stranded DNA (ssDNA) reporter system, which generally contains a fluorescent group and a quenching group. The fluorescence is quenched by the quenching group when the nucleic acid probe is of an intact state, and after being cleaved during the reaction, the nucleic acid probe emits fluorescence. In a preferred embodiment of the present invention, the nucleic acid probe is 5'-6-FAM/TTTATTT/BHQ1-3'.

In a preferred embodiment of the present invention, a method for preparing the Cpf1 protein may include: performing prokaryotic codon optimization on the nucleic acid sequences of cpf1 proteins from different sources to obtain the sequences SEQ ID NOs: 14-23; constructing the sequences into a pET 28a expression vector; performing low-temperature-induced soluble protein expression; and obtaining the target protein by affinity purification and molecular sieve purification.

To solve the aforementioned technical problem, the present invention further provides a method for detecting whether a subject contains a certain virus (e.g., infected with the virus), including performing detection with the nucleic acid detection kit according to the first, third, and fifth aspects of the present invention, the mutated Cpf1 protein according to the second aspect of the present invention, or the crRNA according to the fourth aspect of the present invention. The purpose of the detection is to determine whether the subject contains the nucleic acid of the virus.

Explanation of Terms

The term crRNA refers to CRISPR RNA, which is a short RNA that guides Cas12a (Cpf1) to bind to a target DNA sequence.

The term CRISPR refers to clustered regularly interspaced short palindromic repeats, which are the immune system of many prokaryotes.

The term Cas protein refers to a CRISPR-associated protein, which is an associated protein in a CRISPR system.

The term Cpf1 (also known as Cas12a) refers to a crRNA-dependent endonuclease, which is a type V enzyme in the classification of the CRISPR system.

The term PAM refers to a protospacer-adjacent motif necessary for cleavage by Cas12a, wherein the PAM for FnCas12a is a TTN sequence, and the PAM for LbCas12a is a TTTN sequence.

The term RT-RPA (reverse transcription-recombinase polymerase amplification) is used in the conventional sense of the art and generally refers to reverse transcription isothermal amplification, also known as reverse transcription-recombinase polymerase amplification.

In the present invention, the provided nucleotide sequence is generally considered as including a terminator by default, as would understood by those skilled in the art.

The preferred embodiments of the present invention can be obtained by any combination of the aforementioned preferred conditions based on common knowledge in the art.

The reagents and starting materials used in the present invention are commercially available.

The present invention has the following positive effects:

When the nucleic acid detection kit, mutated Cpf1 protein, or crRNA of the present invention are used for detecting a nucleic acid (for example, detecting the nucleic acid of a SARS-associated coronavirus or MERS coronavirus), the signal intensity during the detection is substantially enhanced, and thus the detection time is reduced and the detection efficiency is improved. In addition, the sensitivity, specificity, and accuracy are high, the detection is visual (detected directly with the naked eyes under a fluorescent lamp), the cost is low, the operation is simple, and no large-scale complex detection equipment is required. These advantages make the kits and detection methods of the present invention more suitable for the basic-level rapid detection, identification, and diagnosis of viruses such as the SARS-associated coronavirus and the MERS-coronavirus in primary experiments and clinical front-line practice. In a preferred embodiment of the present invention, the signal intensity during virus detection is increased by up to 3-5 times over the prior art. In a preferred embodiment of the present invention, the detection sensitivity is 1E8 copies of viruses when the DNA sample of the virus is detected, and 5 copies of viruses when the RNA sample of the virus is detected.

DETAILED DESCRIPTION OF THE PREFERRED EMBODIMENT

The present invention will be described in detail below in connection with specific examples. It should be understood that these examples are only used for describing the present invention and are not intended to limit the scope of the present invention. In addition, it should be understood that various changes and modifications may be made to the present invention by those skilled in the art after reading the content taught by the present invention, and these equivalent forms also fall within the scope defined by the claims appended the present application.

The experimental methods in the following examples which are not specified with specific conditions are generally selected according to conventional methods and conditions or according to the product manual.

In the present invention, a TwistAmp® Basic kit as the RPA amplification kit is purchased from TwistAmp; an MEGAshortscript T7 Transcription Kit as the in vitro crRNA transcription kit and an MEGAclear Kit as the purification kit are purchased from Ambion; conventional reagents such as Tris-Base, BSA, NaCl, Tris-HCl, EDTA, EGTA, $CaCl_2$, $CoCl_2$, $CuSO_4$, $MgCl_2$, $NiSO_4$, $FeSO_4$, $MgSO_4$, $MnCl_2$, $MnSO_4$, $ZnSO_4$, BSA, and glycerol are available from Thermo Fisher; nucleic acid fragments for detection, ssDNA probes and RNA synthesis are completed by GenScript (Nanjing) Biotech Corp.; and the rapid nucleic acid releasing reagent from Vazyme Biotech Co., Ltd. is used for obtaining pretreated nucleic acids in the present invention.

Figure 1:
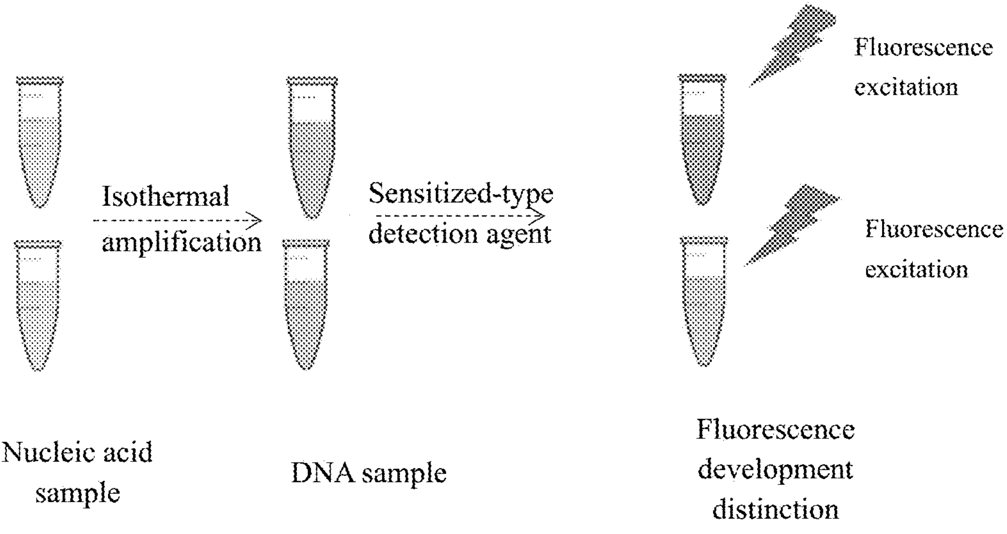
FIG. 1 is a schematic diagram of a method for enhanced Cpf1 rapid detection of a viral nucleic acid.

The overall technical schematic diagram of the present invention is as shown in FIG. 1, including the following three parts: preparation of a nucleic acid sample to be tested, design and preparation of Cpf1 detection components, system construction, and fluorescence detection.

Example 1: Sensitivity-Enhanced Cpf1 Detection Assay

1. Effect of Different Metal Ions on Fluorescence Intensity for Cpf1 Detection

Cpf1 genes from different species were subjected to codon optimization in this example, with the sequences as shown in SEQ ID NOs: 14-23 (the codon-optimized nucleotide sequences respectively corresponding to AsCpf1, BbCpf1, BoCpf1, and FnCpf1 (the amino acid sequence as shown in SEQ ID NO: 55), HkCpf1, Lb4Cpf1, Lb5Cpf1, and LbCpf1 (the amino acid sequence as shown in SEQ ID NO: 54), OsCpf1 and TsCpf1), then cloned into a pet28a plasmid (this step was done by GenScript (Nanjing) Biotech Corp.), expressed in *Escherichia coli*, and purified for detection experiments.

The enhanced Cpf1 detection employed a 20 μL system as shown in Table 1, but not limited thereto, including the adjustment of a ratio of corresponding components, and the metal ions included $CaCl_2$, $CoCl_2$, $CuSO_4$, $NiSO_4$, $FeSO_4$, $MgSO_4$, $MnSO_4$, and $ZnSO_4$.

TABLE 1

| Viral cpf1 detection system | |
|---|---|
| Components | Amount/Sample |
| 10× Buffer | 2 μL |
| Metal ion solution | 1 μL |
| Rnase Inhibitors (40 U/μL, purchased from Vazyme Biotech Co., Ltd.) | 1 μL |
| CRISPR-cpf1 (200 ng/μL) | 1 μL |
| ssDNA FQ reporter (25 pmol/μL) | 1 μL |
| crRNA (1 μM) | 1 μL |
| Sample (DNA reverse transcribed from DNA or RNA of the upE gene of the MERS virus or the ORF1a gene of the MERS virus as prepared in Example 2.1) | X μL |
| $H_2O$ (RNA free) | Up to 20 μL |

The composition of the 10× buffer was: 1,000 mM NaCl, 500 mM Tris, 1,000 μg/mL BSA, and pH 7.9. The ssDNA FQ reporter is 6FAM/TTTATTT/3BHQ1.

The detection efficiency of different metal ions for crRNA3 from the nucleic acid of the MERS virus (with specific information as shown in SEQ ID NO: 6 in Table 2-1 below) was detected sequentially. A Cpf1 detection system was added with each 1 μL of 100 mM metal ion stock solution, with the other components remaining the same, the mixture was mixed homogeneously, and reacted at 37° C. for 30 min, and the above reaction products were subjected to subsequent result detection and judgment.

Figure 2:
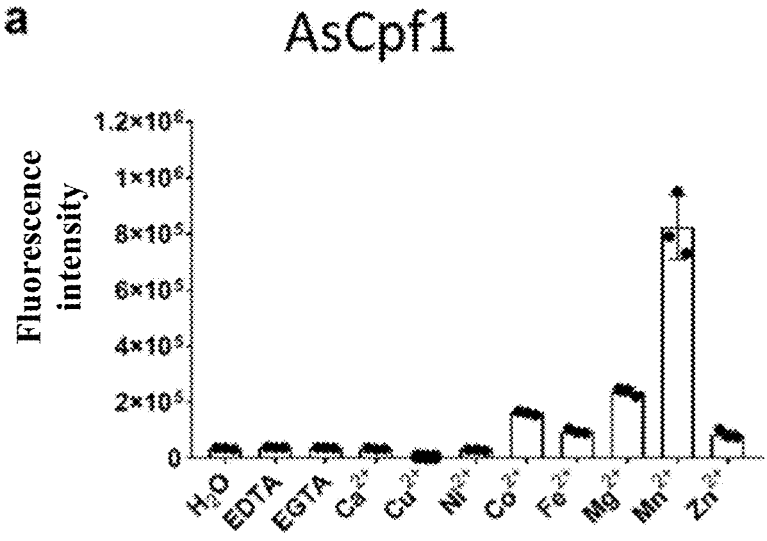
FIG. 2 shows the effect of different metal ions on different Cpf1 signals.
Figure 2:
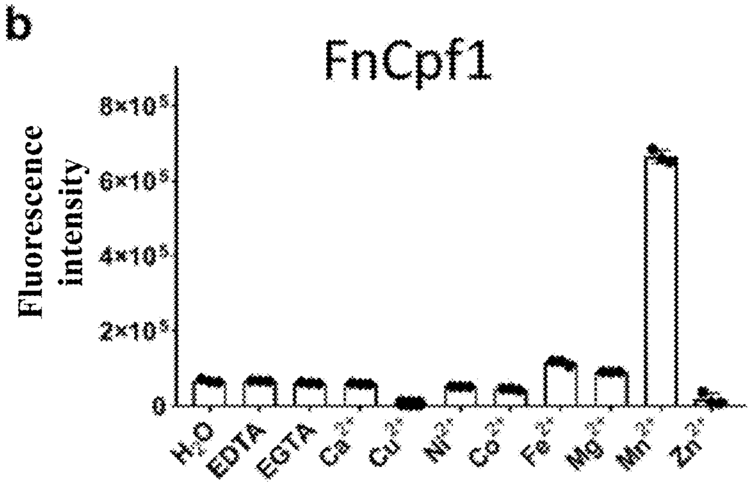
Figure 2:
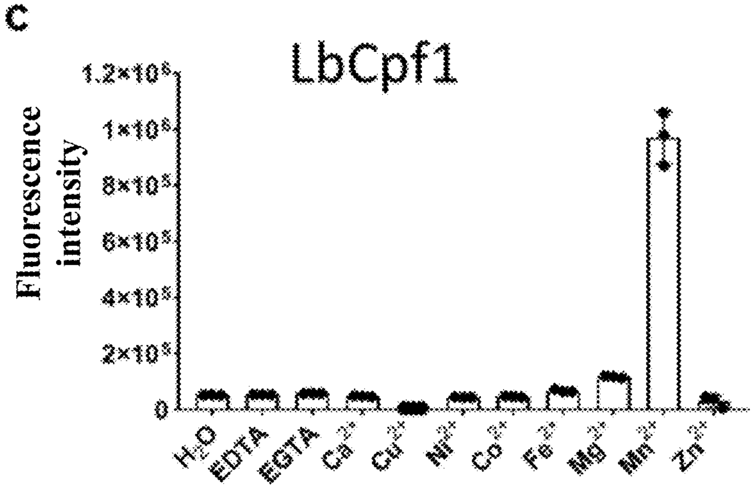

The activity of the Cpf1 detection system was determined with fluorescence detection. The fluorescence of the detection reaction was measured by a full-wavelength microplate reader, with an excitation wavelength of 485 nm and an emission wavelength of 520 nm, and the fluorescence value at 30 min of detection was read as the reaction value. The reaction detection results were as shown in FIG. 2. The results showed that in the detection system of the present invention, the manganese ion can increase the signal intensity for each of AsCpf1, FnCpf1, and LbCpf1, and the fluorescence intensity thereof was significantly increased compared with that of other metal ions and was 3-5 times higher than that of magnesium and iron ions (the result diagrams of AsCpf1, BbCpf1, and BoCpf1 were as shown in FIG. 2, and the resultant results of Cpf1 of other species were similar).

2. Effects of Manganese Ion on Detected Fluorescence Intensities of Different Species of Cpf1

Figure 3:
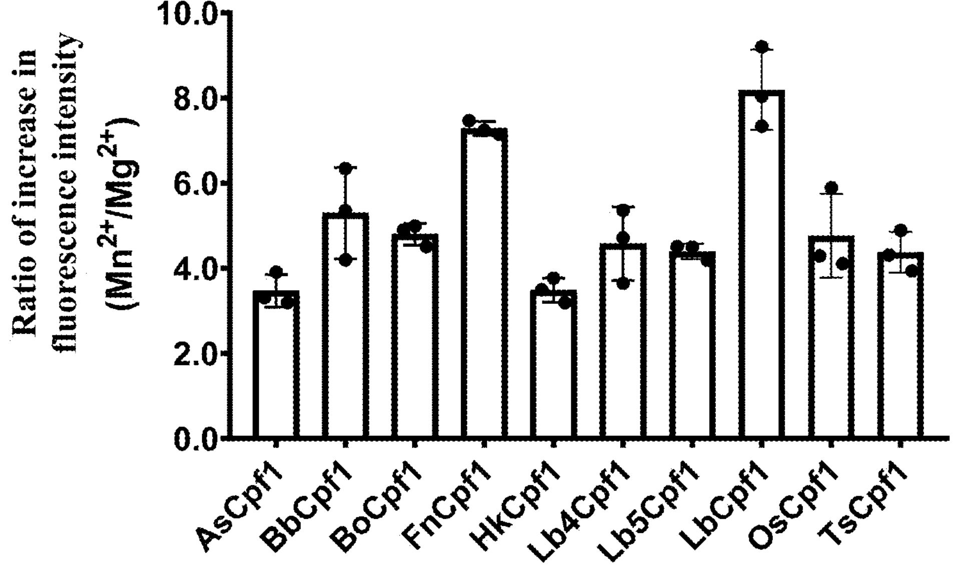
FIG. 3 shows the effect of the manganese ion on the fluorescence detection of different Cpf1 proteins.

The effects of manganese and magnesium ions on the detected fluorescence intensities of different species of Cpf1 were detected sequentially. A Cpf1 detection system was added with each 1 μL of the aforementioned different species of Cpf1 respectively, including AsCpf1, BbCpf1, BoCpf1, FnCpf1, HkCpf1, Lb4Cpf1, Lb5Cpf1, LbCpf1, OsCpf1, and TsCpf1, with the other components remaining the same (same as part 1), the mixture was mixed homogeneously and reacted at 37° C. for 30 min, and the aforementioned reaction products were subjected to subsequent detection and judgment of fluorescence intensity; the fluorescence signal of the manganese ion was divided by the fluorescence signal of the magnesium ion, and the result was as shown in FIG. 3. The result showed that in all of the different species of Cpf1 detection systems of the present invention, the manganese ion can improve the fluorescence signal intensity, with a ratio of the increase in the intensity of the manganese ion relative to the magnesium ion ranging from 3.2 to 8 times.

Figure 11:
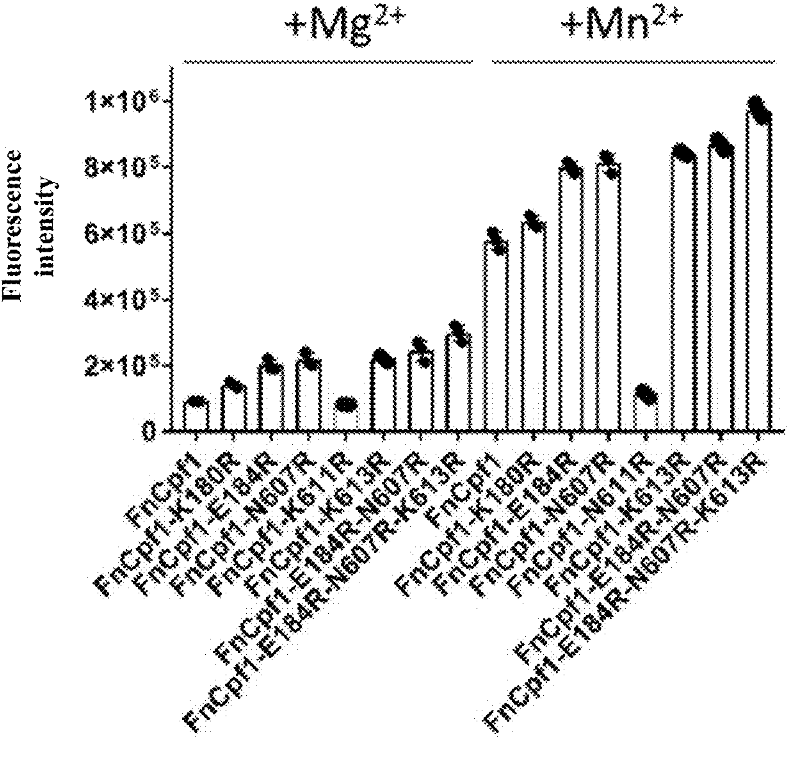
FIG. 11 shows the effect of manganese ions on the fluorescence detection of different Cpf1 mutated proteins.
Figure 11:
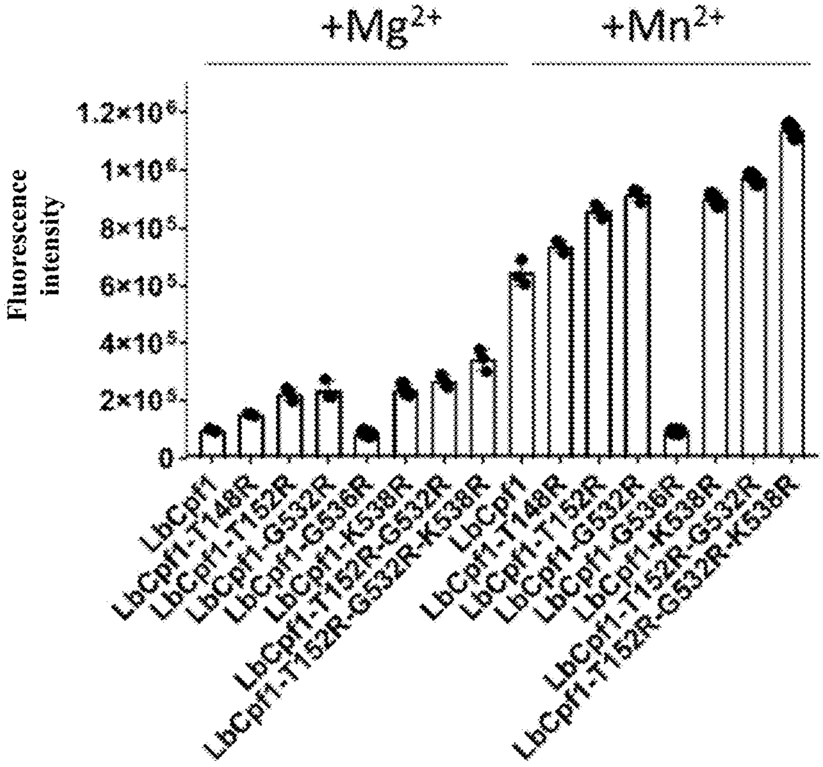

3. Effects of Manganese Ion on Detected Fluorescence Intensities of Different Species of Cpf1 Mutated Proteins The effects of manganese and magnesium ions on the detected fluorescence intensities of different species of Cpf1 (LbCpf1 and FnCpf1) mutated proteins were detected sequentially. A Cpf1 detection system was added with each 1 μL of different species of Cpf1 mutated proteins, including LbCpf1 (with the amino acid sequence as shown in SEQ ID NO: 54), LbCpf1-T148R (SEQ ID NO: 36), LbCpf1-T152R (SEQ ID NO: 37), LbCpf1-G532R (SEQ ID NO: 38), LbCpf1-K536R (SEQ ID NO: 42), LbCpf1-K538R (SEQ ID NO: 39), LbCpf1-T152R/G532R (SEQ ID NO: 40), LbCpf1-T152R/G532R/K538R (SEQ ID NO: 41), FnCpf1 (with the amino acid sequence as shown in SEQ ID NO: 55), FnCpf1-K180R (SEQ ID NO: 30), FnCpf1-E184R (SEQ ID NO: 31), FnCpf1-N607R (SEQ ID NO: 32), FnCpf1-K611R (SEQ ID NO: 43), FnCpf1-K613R (SEQ ID NO: 33), FnCpf1-E184R/N607R (SEQ ID NO: 34), FnCpf1-E184R/N607R/K613R (SEQ ID NO: 35), with the other components remaining the same (same as part 1), the mixture was mixed homogeneously, and reacted at 37° C. for 30 min, and the aforementioned reaction products were subjected to subsequent detection and judgment of results, and the detection results were as shown in FIG. 11. The results showed that in the different species of Cpf1 mutation detection system of the present invention, some mutations could increase the signal intensity, but LbCpf1-K536R and FnCpf1-K611R could not increase the signal intensity. The manganese ion can increase the fluorescence signal intensity of the active mutated protein, with a ratio of the increase in the intensity of the manganese ion relative to the magnesium ion ranging from 3 to 5 times. In addition, the Cpf1 mutated protein also has a corresponding increase in fluorescent signal intensity relative to the unmutated Cpf1 protein, wherein the mutants FnCpf1-E184R, FnCpf1-N607R, FnCpf1-K613R, FnCpf1-E184R/N607R, FnCpf1-E184R/N607R/K613R, and LbCpf1-T152R, LbCpf1-G532R, LbCpf1-K538R, LbCpf1-T152R/G532R, LbCpf1-T152R/

G532R/K538R had a ½-1 times increase in fluorescent signal intensity relative to their unmutated proteins.

4. Enhancing Effects of Different Forms of Manganese Salts on Signal

Figure 4:
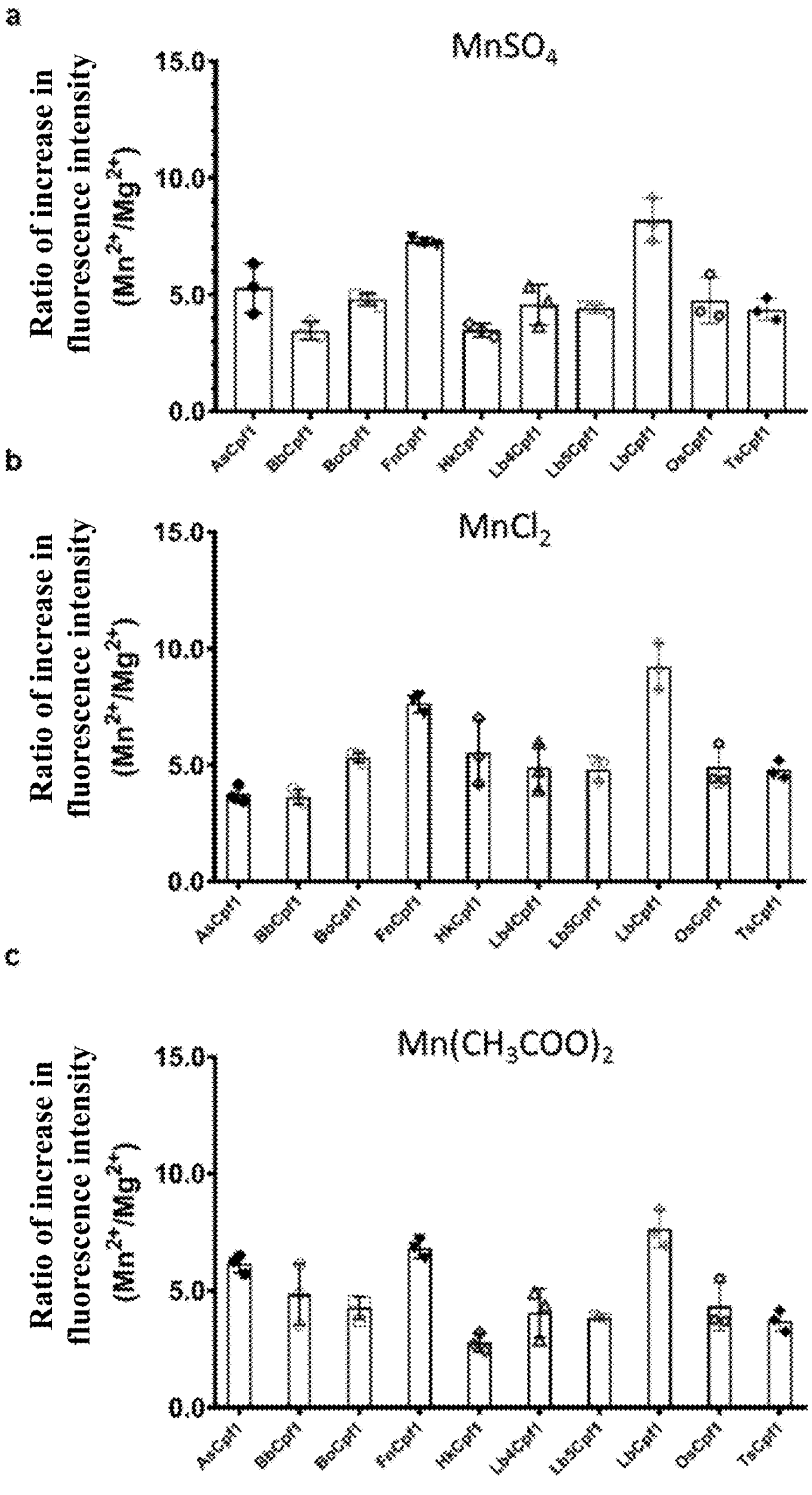
FIG. 4 shows the effect of different manganese salts on the fluorescence detection of different Cpf1 proteins.

The effects of $MnSO_4$, $MnCl_2$, and $Mn(CH_3COO)_2$ on the detected fluorescence intensities of different species of Cpf1 were detected sequentially. A Cpf1 detection system was added with each 1 μL of the different species of Cpf1, including AsCpf1, BbCpf1, BoCpf1, FnCpf1, HkCpf1, Lb4Cpf1, Lb5Cpf1, LbCpf1, OsCpf1, and TsCpf1, with the other components remaining the same (same as part 1), the mixture was blended homogeneously and reacted at 37° C. for 30 min, the aforementioned reaction products were subjected to subsequent detection and judgment of fluorescence intensity, and the results were as shown in FIG. 4. The results showed that different forms of manganese salts could increase the fluorescence signal intensity in the detection system of the present invention.

Example 2: Rapid and Sensitive Detection of Gene Fragments of SARS and MERS Viruses 2.1 Nucleic Acid Preparation In this example, the orf1ab gene of the SARS-CoV virus was referred to the AY278487 gene on NCBI, the upE gene fragment of the MERS virus was referred to the JX869059 gene on NCBI, the ORF1a gene fragment of the MERS virus was referred to the JX869059 gene on NCBI, and the E gene fragment, S gene fragment, M gene fragment, and N gene fragment of the SARS-CoV-2 virus were referred to the NC045512 genome on NCBI, which were all synthesized by GenScript (Nanjing) Biotech Corp., and named as SARS-ORF1ab, MERS-upE, MERS-ORF1a, SARS-CoV-2-E, SARS-CoV-2-S, SARS-CoV-2-M, SARS-CoV-2-N, with corresponding sequences as shown in SEQ ID NOs: 11-13, SEQ ID NO: 46, SEQ ID NOs: 79-81, respectively.

RNA nucleic acid samples corresponding to the orf1ab gene of the SARS-CoV virus, the upE gene fragment and ORF1a of the MERS virus, the E gene of the SARS-CoV-2 virus, the S gene of the SARS-CoV-2 virus, the M gene of the SARS-CoV-2 virus, and the N gene of the SARS-CoV-2 virus were prepared by in vitro transcription. The specific operation was as follows: the corresponding gene RNA samples pcRNA-SARS-orf1ab, pcRNA-MERS-upE and pcRNA-MERS-ORF1a, pcRNA-SARS-CoV-2-E, pcRNA-SARS-CoV-2-S, pcRNA-SARS-CoV-2-M, pcRNA-SARS-CoV-2-N were transcribed by using the MEGAshortscript T7 transcription kit (Thermo Fisher Scientific) with the aforementioned SARS-ORF1ab, MERS-upE, and ORF1a, SARS-CoV-2-E, SARS-CoV-2-S, SARS-CoV-2-M, SARS-CoV-2-N as templates, respectively. The transcribed RNA was purified by using the MEGAclear kit (Thermo Fisher Scientific) and recovered by an ethanol precipitation method. The resulting single-stranded RNA (ssRNA) after transcription was detected for mass and concentration, and stored at −80° C. until use.

2.2 Design and Preparation for Specific crRNA

Preparation for a specific crRNA was performed according to the following protocol: designing a 44 bp crRNA by searching for a targeting sequence containing the cpf1 recognition sequence Protospacer Adjacent Motif (PAM) TTTN against SARS-ORF1ab, MERS-upE gene, MERS-ORF1a gene, SARS-CoV-2-E gene, SARS-CoV-2-S gene, SARS-CoV-2-M gene, SARS-CoV-2-N. They were named as SARS-orf1ab-crRNA1 to SARS-orf1a-crRNA3 against the SARS-ORF1ab gene, MERS-upE-crRNA1 to MERS-upE-crRNA4 against the MERS-upE gene, MERS-ORF1a-crRNA1 to MERS-ORF1a-crRNA3 against the MERS-ORF1a gene, Cov2-E-crRNA1 to CoV2-E-crRNA7 against SARS-CoV2-E gene, Cov2-S-cr3 to CoV2-S-cr10 against SARS-CoV2-S gene, Cov2-M-cr1 to CoV2-M-cr5 against SARS-CoV2-M gene, and Cov2-N-cr1 to CoV2-N-cr4 against SARS-CoV2-N gene, respectively. After the design was complete, crRNA was prepared. The preparation of crRNA could be carried out by GenScript (Nanjing) Biotech Corp., in which an oligo could be synthesized and constructed into a vector pUC57-T7-crRNA, and the target crRNA could be obtained through in vitro transcription; or a RNA corresponding to the crRNA sequence could be synthesized directly by GenScript (Nanjing) Biotech Corp.

The crRNAs of the SARS-ORF1ab, MERS-upE gene, MERS-ORF1a gene and SARS-CoV-2-E gene, SARS-CoV-2-S gene, SARS-CoV-2-M gene, and SARS-CoV-2-N gene provided by the present invention included SEQ ID NO: 1 to SEQ ID NO: 10, SEQ ID NO: 47 to SEQ ID NO: 53, SEQ ID NO: 56 to SEQ ID NO: 72, and the specific information was as shown in Table 2-1 and Table 2-2:

TABLE 2-1 crRNA specific for nucleic acids of SARS and MERS viruses

| crRNA Sequence Number | Sequence Name | crRNA Sequence (5' to 3') |
|---|---|---|
| SEQ ID NO: 1 | SARS-O-Cr1 | UAAUUUCUACUAAGUGUAGAU UACAGGUUAGCUAACGAGUGU GC |
| SEQ ID NO: 2 | SARS-O-Cr2 | UAAUUUCUACUAAGUGUAGAU UCAAGCUGUUACAGCCAAUGU AA |
| SEQ ID NO: 3 | SARS-O-Cr3 | UAAUUUCUACUAAGUGUAGAU AACUGAUGGUAAUAAGAUAGC UG |
| SEQ ID NO: 4 | MC-E-crRNA1 | UAAUUUCUACUAAGUGUAGAU GACAUAUGGAAAACGAACUAU GU |
| SEQ ID NO: 5 | MC-E-crRNA2 | UAAUUUCUACUAAGUGUAGAU UCCAAGAACGAAUAGGGUUGU UC |

TABLE 2-1-continued crRNA specific for nucleic acids of SARS and MERS viruses

| crRNA Sequence Number | Sequence Name | crRNA Sequence (5' to 3') |
|---|---|---|
| SEQ ID NO: 6 | MC-E-crRNA3 | UAAUUUCUACUAAGUGUAGAU CUAUGAACAACCCUAUUCGUUC U |
| SEQ ID NO: 7 | MC-E-crRNA4 | UAAUUUCUACUAAGUGUAGAU CAUAUGUCCAAAGAGAGACUA AU |
| SEQ ID NO: 8 | MC-O-Cr1 | UAAUUUCUACUAAGUGUAGAU ACUUAUGCAAACAUAGUCUAC GA |
| SEQ ID NO: 9 | MC-O-Cr2 | UAAUUUCUACUAAGUGUAGAU GUCAGCGCUGAUUGCAGUUGC AA |
| SEQ ID NO: 10 | MC-O-Cr3 | UAAUUUCUACUAAGUGUAGAU CAACUGCAAUCAGCGCUGACGA A |
| SEQ ID NO: 47 | CoV2-E-Cr1 | UAAUUUCUACUAAGUGUAGAU ACAAGACUCACGUUAACAAUA UU |
| SEQ ID NO: 48 | CoV2-E-Cr2 | UAAUUUCUACUAAGUGUAGAU ACACGAGAGUAAACGUAAAAA GA |
| SEQ ID NO: 49 | CoV2-E-Cr3 | UAAUUUCUACUAAGUGUAGAU AACACGAGAGUAAACGUAAAA AG |
| SEQ ID NO: 50 | CoV2-E-Cr4 | UAAUUUCUACUAAGUGUAGAU UACGUUUACUCUCGUGUUAAA AA |
| SEQ ID NO: 51 | CoV2-E-Cr5 | UAAUUUCUACUAAGUGUAGAU UAACACGAGAGUAAACGUAAA AA |
| SEQ ID NO: 52 | CoV2-E-Cr6 | UAAUUUCUACUAAGUGUAGAU ACGUUUACUCUCGUGUUAAAA AU |
| SEQ ID NO: 53 | CoV2-E-Cr7 | UAAUUUCUACUAAGUGUAGAU CGUUUACUCUCGUGUUAAAAA UC |

TABLE 2-2 crRNA specific for SARS and MERS virus nucleic acids

| crRNA Sequence Number | Sequence Name | crRNA Sequence (5' to 3') |
|---|---|---|
| SEQ ID NO: 56 | CoV2-S-cr3 | UaaUUUcUacUaagUgUagaUACAAG ACUCACGUUAACAAUAUU |
| SEQ ID NO: 57 | CoV2-S-cr4 | UaaUUUcUacUaagUgUagaUACACG AGAGUAAACGUAAAAAGA |
| SEQ ID NO: 58 | CoV2-S-cr5 | UaaUUUcUacUaagUgUagaUAACAC GAGAGUAAACGUAAAAAG |
| SEQ ID NO: 59 | CoV2-S-cr6 | UaaUUUcUacUaagUgUagaUUACGU UUACUCUCGUGUUAAAAA |
| SEQ ID NO: 60 | CoV2-S-cr7 | UaaUUUcUacUaagUgUagaUUAACA CGAGAGUAAACGUAAAAA |

TABLE 2-2-continued crRNA specific for SARS and MERS virus nucleic acids

| crRNA Sequence Number | Sequence Name | crRNA Sequence (5' to 3') |
|---|---|---|
| SEQ ID NO: 61 | CoV2-S-cr8 | UaaUUUcUacUaagUgUagaUACGUU UACUCUCGUGUUAAAAAU |
| SEQ ID NO: 62 | CoV2-S-cr9 | UaaUUUcUacUaagUgUagaUCGUUU ACUCUCGUGUUAAAAAUC |
| SEQ ID NO: 63 | CoV2-S-cr10 | UaaUUUcUacUaagUgUagaUACuCCu GGuGAuuCuuCuuCAGG |
| SEQ ID NO: 64 | CoV2-M-cr1 | UaaUUUcUacUaagUgUagaUuAGAA GCGGuCuGGuCAGAAuAG |
| SEQ ID NO: 65 | CoV2-M-cr2 | UaaUUUcUacUaagUgUagaUGGCAG GuCCuuGAuGuCACAGCG |
| SEQ ID NO: 66 | CoV2-M-cr3 | UaaUUUcUacUaagUgUagaUuuuAGG CAGGuCCuuGAuGuCAC |
| SEQ ID NO: 67 | CoV2-M-cr4 | UaaUUUcUacUaagUgUagaUuAAuA AGAAAGCGuuCGuGAuGu |
| SEQ ID NO: 68 | CoV2-M-cr5 | UaaUUUcUacUaagUgUagaUuuAuuA CAAAuuGGGAGCuuCGC |
| SEQ ID NO: 69 | CoV2-N-cr1 | UaaUUUcUacUaagUgUagaUuuGAAC uGuuGCGACuACGuGAu |
| SEQ ID NO: 70 | CoV2-N-cr2 | UaaUUUcUacUaagUgUagaUCuGCuG CuuGACAGAuuGAACCA |
| SEQ ID NO: 71 | CoV2-N-cr3 | UaaUUUcUacUaagUgUagaUCuCuCA AGCuGGuuCAAuCuGuC |
| SEQ ID NO: 72 | CoV2-N-cr4 | UaaUUUcUacUaagUgUagaUGCCuuG uuGuuGuuGGCCuuuAC |

2.3 Reverse Transcription Isothermal Amplification Reaction

In this example, single-stranded RNA (ssRNA) viral nucleic acids prepared in 2.1 above were pre-amplified by using reverse transcription isothermal amplification (RT-RPA) for the cpf1 detection reaction. Amplification primers RT-RPA-F (forward primer) and RT-RPA-R (reverse primer) for Rt-RPA were designed and synthesized according to the requirements of isothermal amplification reaction (Table 3). According to the RT-RPA isothermal amplification procedure, a sample to be tested was amplified. The specific operation was as follows: isothermal amplification was performed in a 50 μL reaction system. x μL of RNA sample, (18.5-x) μL of ddH$_2$O, 2 μL of the respective RPA-F in Table 3, 2 μL of RPA-R, and 25 μL of reaction buffer were blended, and the mixture was added into the reaction tube to dissolve and blend homogeneously. Finally, 2.5 μL of magnesium acetate was added, the mixture was blended homogeneously and incubated at 39° C. for 30 min. RT-RPA product samples were detected in the next step.

TABLE 3

RT-RPA primer sequences specific for nucleic acid of coronavirus CoV

| SEQ Name | Primer Name | Primer Sequence |
|---|---|---|
| SEQ ID NO: 24 | SARS-orf1ab-RPA-F | CTAACATGCTTAGGATAATGGC CTCTCTTGTTC |
| SEQ ID NO: 25 | SARS-orf1ab-RPA-R | GTAAGCGTAAAACTCATCCACG AATTCATGATC |
| SEQ ID NO: 26 | MERS-upE-RPA-F | CTCGCTTATCGTTTAAGCAGCT CTGCGCTACTATG |
| SEQ ID NO: 27 | MERS-upE-RPA-R | CTCGCTTATCGTTTAAGCAGCT CTGCGCTACTATG |
| SEQ ID NO: 28 | MERS-Orf1-RPA-F | CTATTCCCACACAGTTGTTCCC ACTCTTAT |
| SEQ ID NO: 29 | MERS-Orf1-RPA-R | CTTGAGGCTTCTCCAATGCTAT AAGTGTAC |

TABLE 3-continued

| RT-RPA primer sequences specific for nucleic acid of coronavirus CoV | | |
|---|---|---|
| SEQ Name | Primer Name | Primer Sequence |
| SEQ ID NO: 44 | CoV2-E-RPA-F | TGTACTCATTCGTTTCGGAAGA GACAGGTACG |
| SEQ ID NO: 45 | Cov2-E-RPA-R | TAGACCAGAAGATCAGGAACT CTAGAAGAATTCAG |
| SEQ ID NO: 73 | CoV2-S-RPA-F | GGAAAGTGAGTTCAGAGTTTA TTCTAGTGCGA |
| SEQ ID NO: 74 | CoV2-S-RPA-R | CACAGTCTACAGCATCTGTAAT GGTTCCAT |
| SEQ ID NO: 75 | CoV2-M-RPA-F | CTACTTCATTGCTTCTTTCAGA CTGTTTGC |
| SEQ ID NO: 76 | CoV2-M-RPA-R | TTATAGTTGCCAATCCTGTAGC GACTGTAT |
| SEQ ID NO: 77 | CoV2-N-RPA-F | ATCGTGCTACAACTTCCTCAAG GAACAACA |
| SEQ ID NO: 78 | CoV2-N-RPA-R | GCAATTTGCGGCCAATGTTTGT AATCAGTT |

2.4 In this example, as shown in Table 4, the enhanced cpf1 detection was conducted in a 20 μL system, but not limited thereto, including the adjustment of a ratio of corresponding components:

TABLE 4

| Virus cpf1 detection system | |
|---|---|
| Components | Amount/Sample |
| 10× Buffer | 2 μL |
| Metal ion solution | 1 μL |
| Rnase Inhibitors (40 U/μL) | 1 μL |
| CRISPR-cpf1 (200 ng/μL) | 1 μL |
| ssDNA FQ reporter (25 pmol/μL) | 1 μL |
| crRNA (1 μM) | 1 μL |
| Sample | X μL |
| $H_2O$ (RNA-free) | Up to 20 μL |

2.5 Fluorescence Detection with a Full-Wavelength Microplate Reader

In a fluorescence detection by a microplate reader, 2 μL of 10× buffer, 1 μL of L Rnase Inhibitors, 1 μL of Cpf1, 1 μL of L ssDNA FQ reporter, 5 μL of the RT-RPA product sample obtained in 2.3 above, 1 μL of L crRNA, and 9 μL of $H_2O$ were added to a system for detecting a target gene by Cpf1 sequentially. The components were blended homogeneously and reacted at 37° C. for 30 min. In the above reaction system, the concentration of Rnase Inhibitors was 40 U/μL, the concentration of Cpf1 was 200 ng/μL, the concentration of ssDNA FQ reporter was 25 pM/μL, and the concentration of crRNA was 1 nM/μL.

Firstly, the detection efficiency of crRNA against the orf1ab gene of SARS-CoV, upE gene of MERS virus, ORF1a gene of MERS virus, E gene of SARS-CoV-2, S gene of SARS-CoV-2, M gene of SARS-CoV-2, and N gene of SARS-CoV-2 were detected sequentially. To a Cpf1 detection system was added 1 μL of crRNA respectively, with the other components remaining the same, the mixture was mixed homogeneously, and reacted at 37° C. for 30 min, and the above reaction products were subjected to subsequent results detection and judgment.

Figure 5:
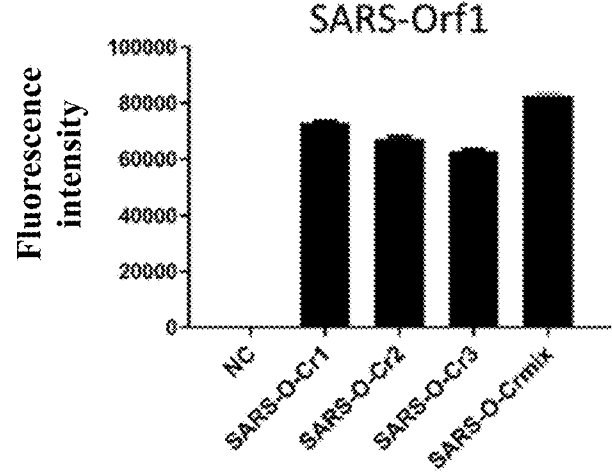
FIG. 5 shows the fluorescence detection effects of different crRNAs in detecting different genes of SARS and MERS viruses.
Figure 5:
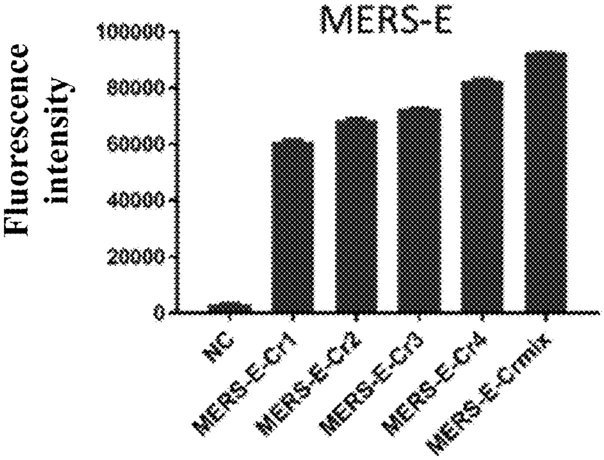
Figure 5:
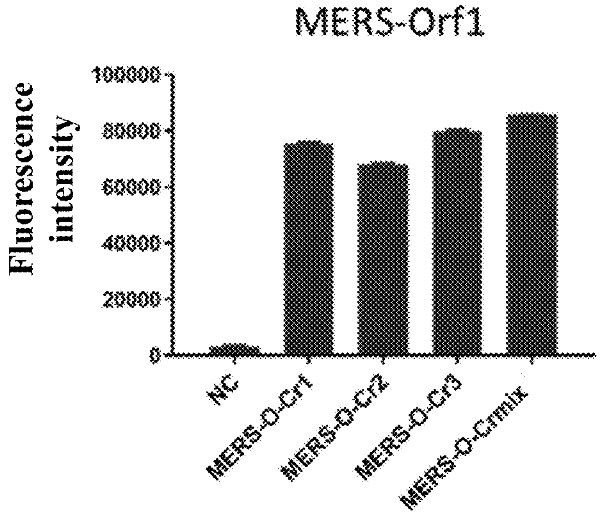
Figure 12:
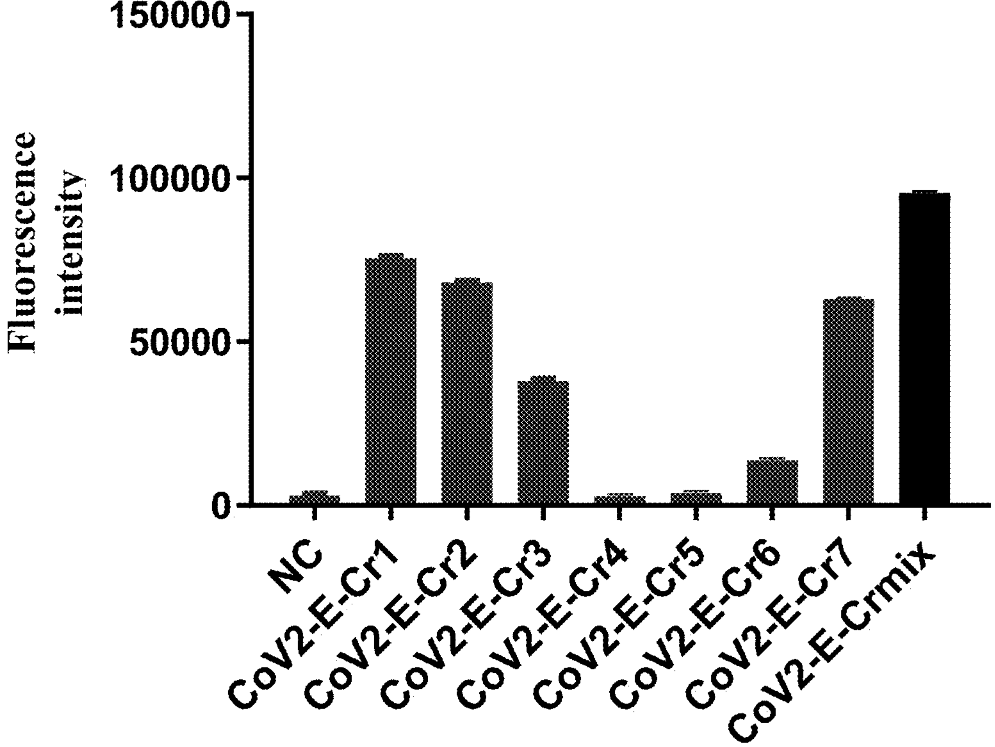
FIG. 12 shows the fluorescence detection effect of different crRNAs in detecting SARS-CoV-2 viral genes.
Figure 14:
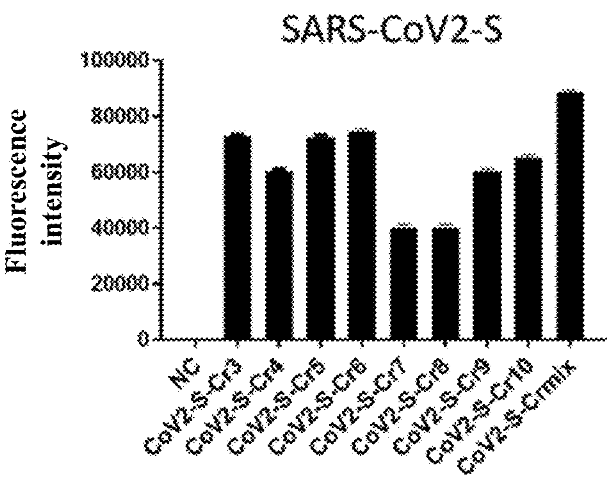
FIG. 14 shows detection results of a S gene, M gene, and N gene against SARS-CoV-2.
Figure 14:
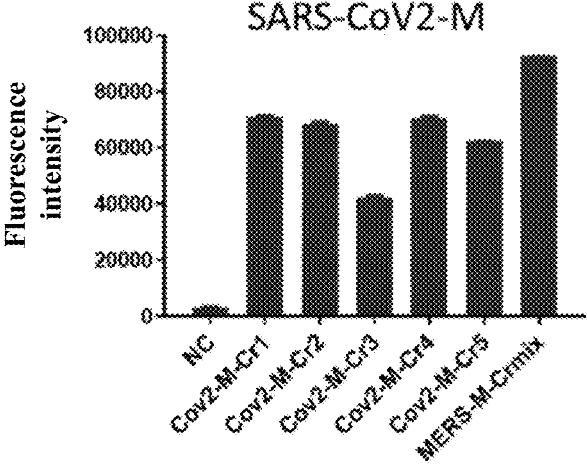
Figure 14:
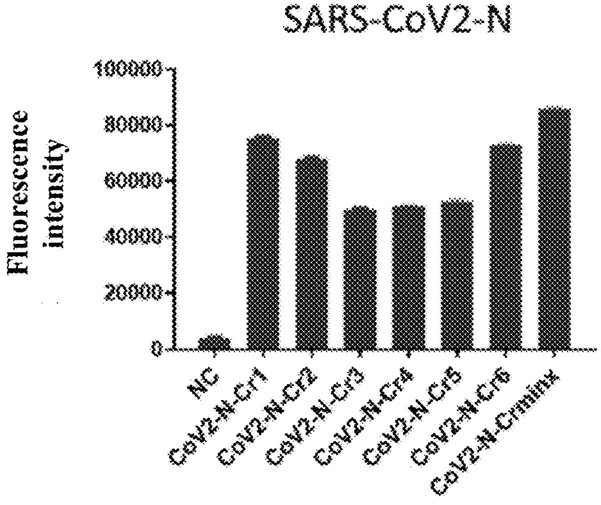
Figure 15:
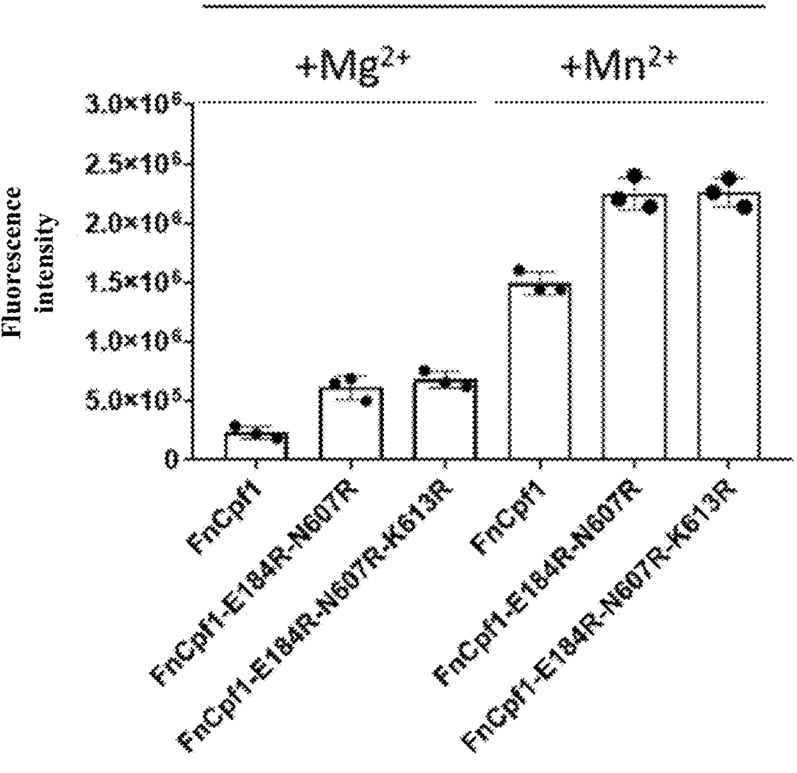
FIG. 15 is a graph showing the results of detecting a E gene of SARS-CoV2 in different cpf1 mutants by a microplate reader.
Figure 15:
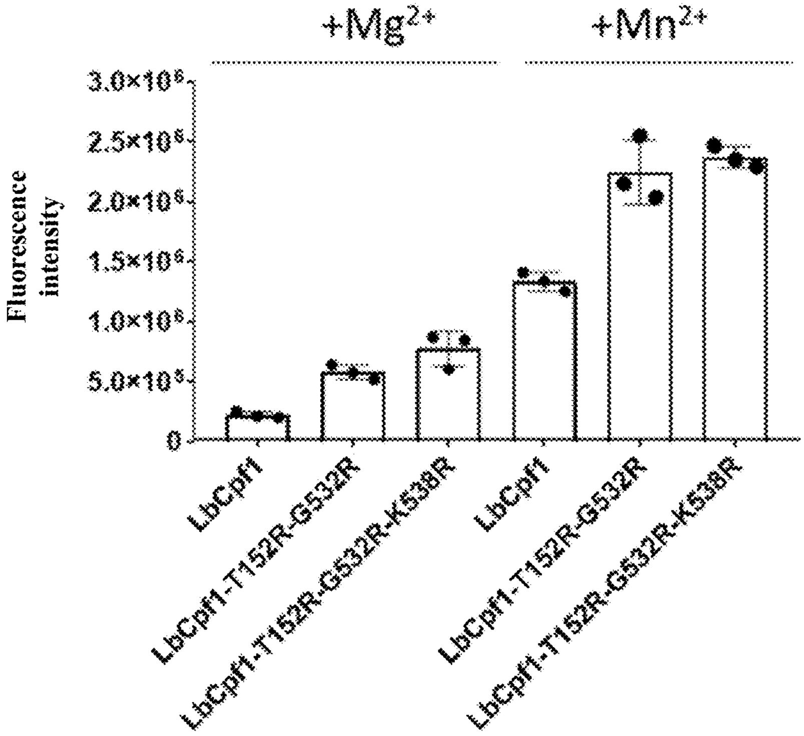
Figure 16:
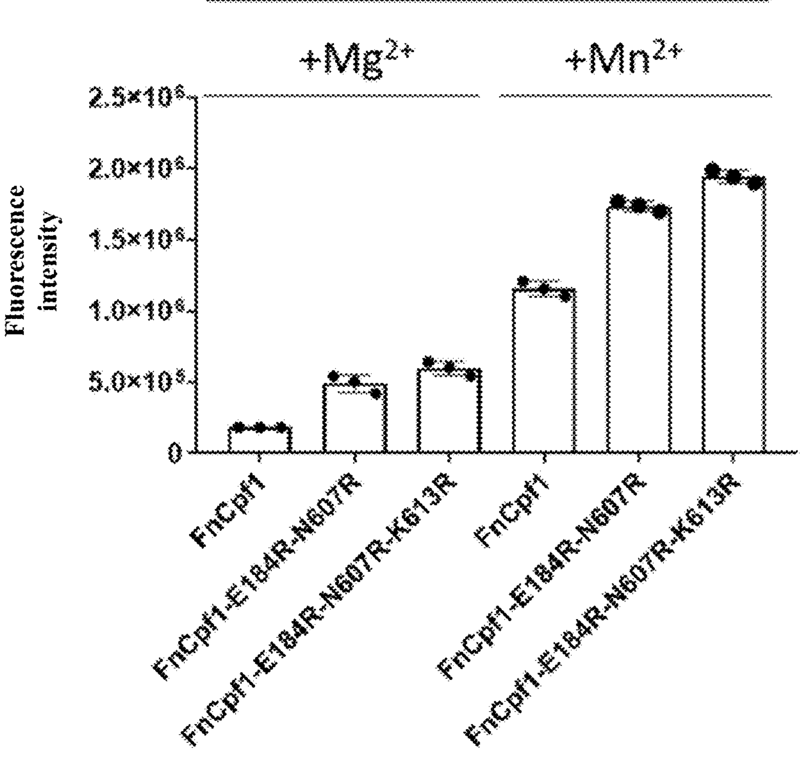
FIG. 16 is a graph showing the results of detecting a S gene of SARS-CoV2 in different cpf1 mutants by a microplate reader.
Figure 16:
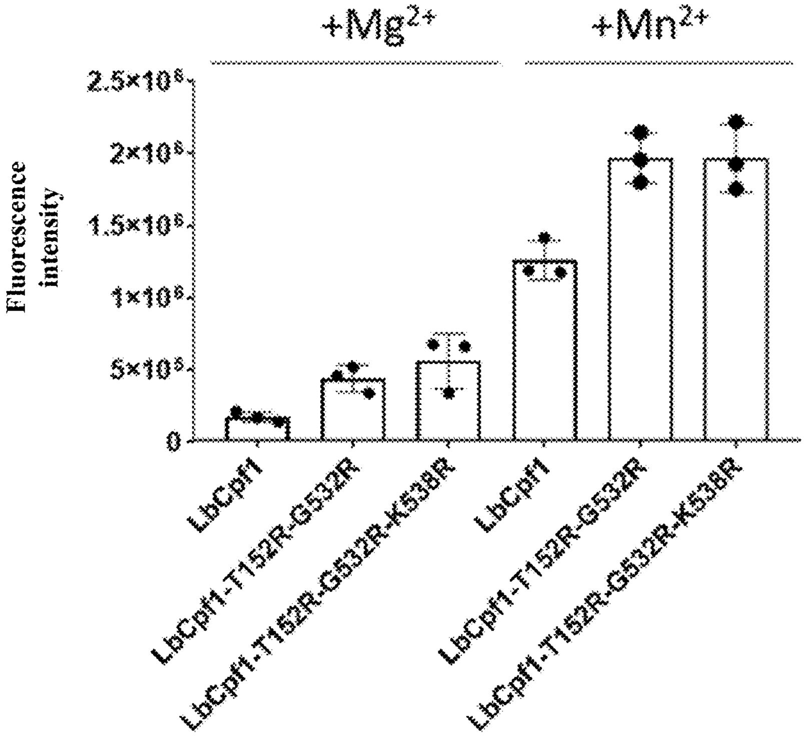
Figure 17:
FIG. 17 is a graph showing the results of detecting a M gene of SARS-CoV2 in different cpf1 mutants by a microplate reader.
Figure 17:
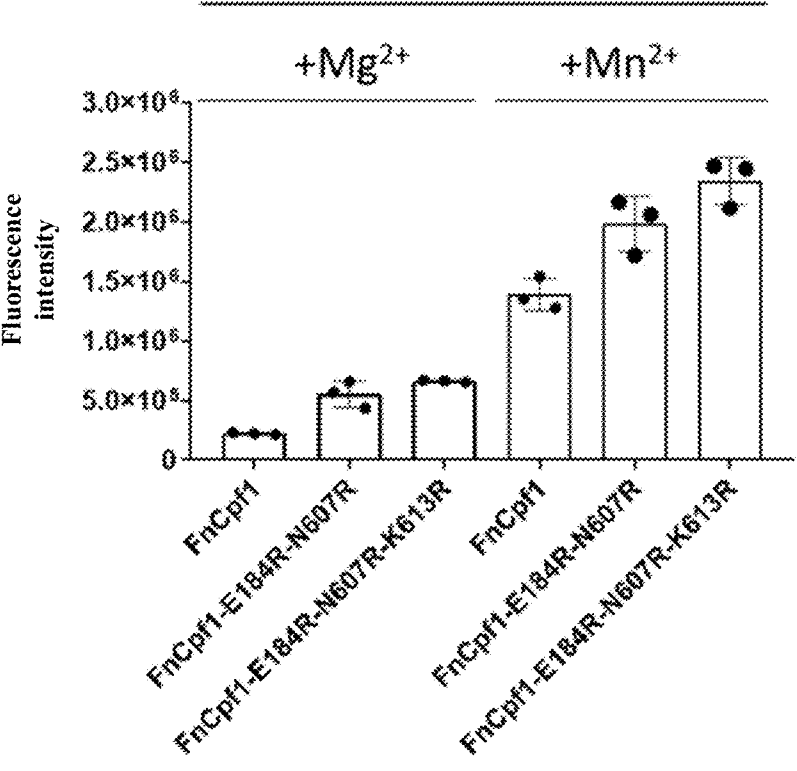
Figure 17:
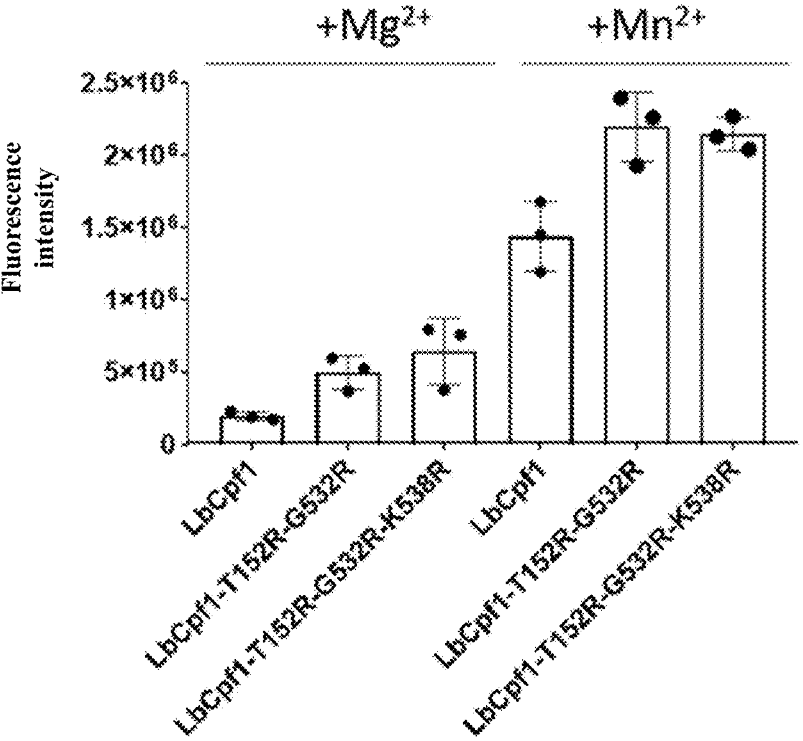
Figure 18:
FIG. 18 is a graph showing the results of detecting a N gene of SARS-CoV2 in different cpf1 mutants by a microplate reader.
Figure 18:
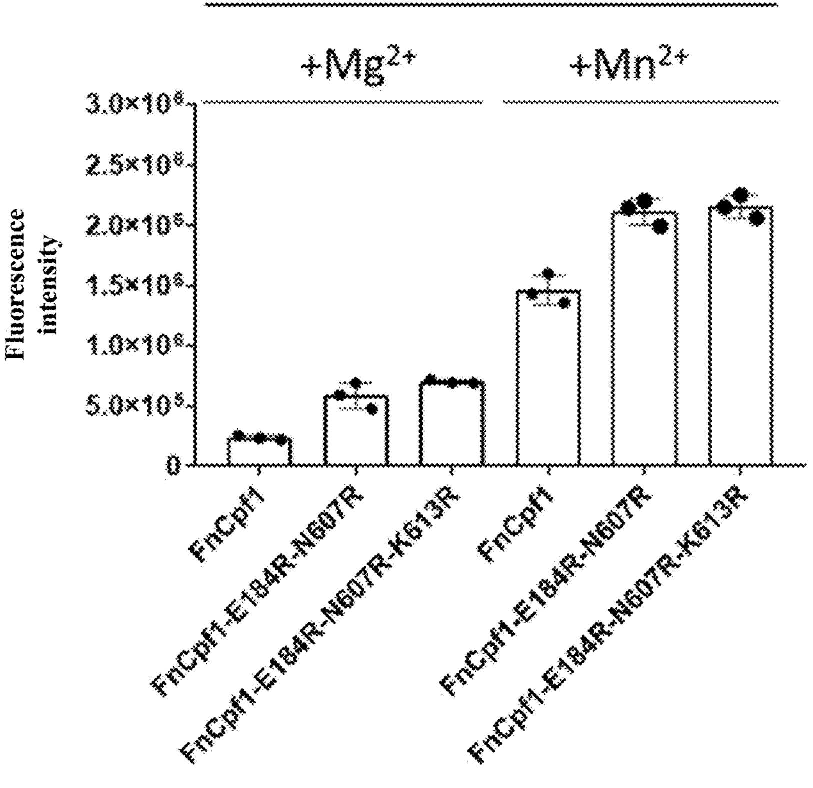
Figure 18:
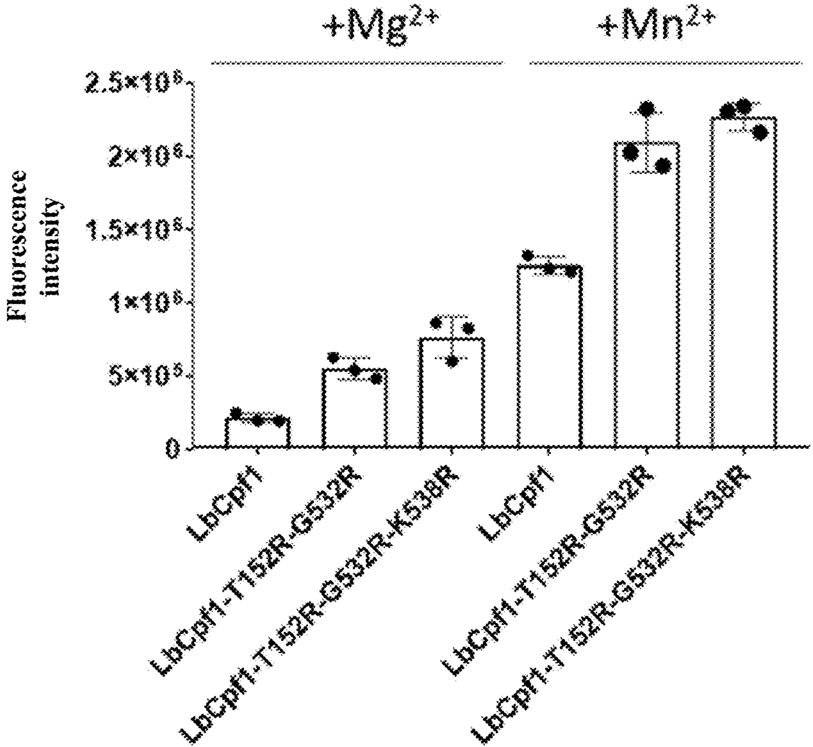

The activity of the Cpf1 detection system was determined with a fluorescence detection. The fluorescence of the detection reaction was measured by a full-wavelength microplate reader, with an excitation wavelength of 485 nm and an emission wavelength of 520 nm, and the detected fluorescence value at 30 min was read as the reaction value. The results for different crRNA against SARS-CoV and MERS virus were as shown in FIG. 5. The results showed that in the detection system of the present invention, crRNA against different gene fragments could effectively and specifically detect the corresponding gene fragments. The detection results of E gene against SARS-CoV-2 were as shown in FIG. 12, wherein CoV2-E-Cr4 and CoV2-E-Cr5 could not be detected, CoV2-E-Cr3 and CoV2-E-Cr6 had a low detection efficiency, and CoV2-E-Cr1, CoV2-E-Cr2, and CoV2-E-Cr7 had a high detection efficiency. In subsequent experiments, CoV2-E-Cr1, CoV2-E-Cr2, and CoV2-E-Cr7 were mixed to prepare SARS-CoV2-Crmix for a subsequent detection of SARS-CoV-2-E gene. The detection results of the S gene, M gene, and N gene against SARS-CoV-2 were as shown in FIG. 14, and crRNA against different gene fragments can efficiently and specifically detect the corresponding gene fragments. CoV2-S-Cr3, CoV2-S-Cr5, and CoV2-S-Cr6 had a higher detection efficiency for SARS-CoV-2-S gene, and these three crRNA were mixed to prepare CoV2-S-Crmix for subsequent monitoring of SARS-CoV-2-S gene; wherein CoV2-M-Cr1, CoV2-M-Cr2, and CoV2-M-Cr4 had a higher detection efficiency for SARS-CoV-2-M gene, and these three crRNA were mixed in subsequent experiments to prepare CoV2-M-Crmix for subsequent monitoring of SARS-CoV-2-M gene; wherein, CoV2-N-Cr1, CoV2-N-Cr2, and CoV2-N-Cr6 had a higher detection efficiency for SARS-CoV-2-N, and these three crRNA were mixed to prepare CoV2-N-Crmix for subsequent monitoring of SARS-CoV-2-N gene.

In view of the consistent detection effect of crRNA against SARS-orf1ab and MERS-upE genes in this example, SARS-O-crRNA1 to SARS-O-crRNA3 against the SARS-orf1ab gene were mixed in an equal proportion to obtain SARS-O-Crmix; MERS-E-crRNA1 to MERS-E-crRNA4 against the MERS-upE gene were mixed in an equal proportion to obtain MERS-E-Crmix; MERS-O-crRNA1 to MERS-O-crRNA3 against the MERS-Orf gene were mixed in an equal proportion to obtain MERS-O-Crmix. In the subsequent detection, the SARS-orf1ab gene was detected by SARS-O-Crmix, the MERS-upE gene was detected by MERS-E-Crmix, and the MERS-Orf gene was detected by MERS-O-Crmix.

Example 3: High-Sensitivity Detection of Viral Nucleic Acid Based on cpf1 Fluorescence Method In this example, to measure the effect of the cpf1 fluorescence method on the detection sensitivity, the following detection was performed.

(1) Firstly, according to the DNA sample corresponding to SARS-orf1ab, MERS-upE, and MERS-Orf1 gene fragments as described in 2.1 of Example 2, the molecular weight of the detection fragment was calculated, and gradient dilution was performed to obtain the detection sample containing 5E9, 1E9, 5E8, 1E8, 5E7, and 1E7 copies per microlitre (copy/μL).

The above diluted sample was subjected to a cpf1-specific reaction by the fluorescence method, and detection and interpretation of fluorescence results were performed according to the detection procedure in Example 2. The operation was briefly described as follows: 1 μL of gradient diluted samples were added into a 20 μL of cpf1 fluorescent nucleic acid detection system (wherein the added crRNA was SARS-O-Crmix for detecting SARS-orf1ab gene, MERS-E-Crmix for detecting MERS-upE gene, or MERS-O-Crmix for detecting MERS-Orf gene as described above), the mixture was blended homogeneously and reacted at 37° C. for 30 min to interpret the fluorescence results.

Figure 6:
FIG. 6 shows the sensitivity of the enhanced Cpf1 fluorescence detection for DNAs of the SARS and MERS viruses.
Figure 6:
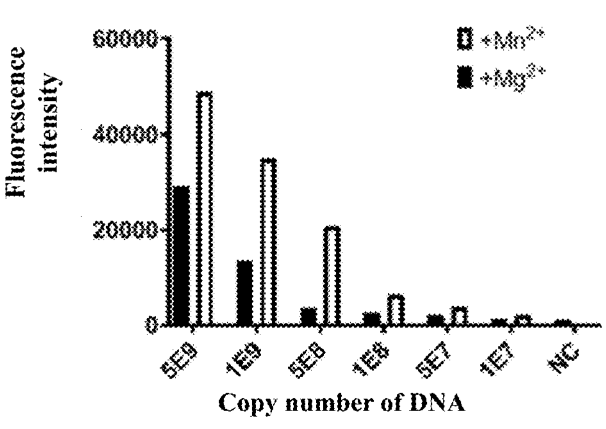
Figure 6:
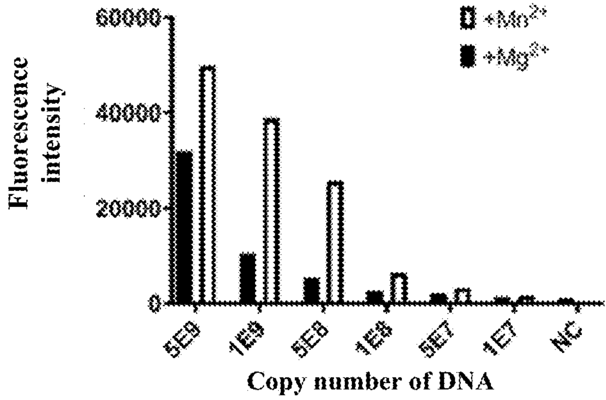
Figure 6:
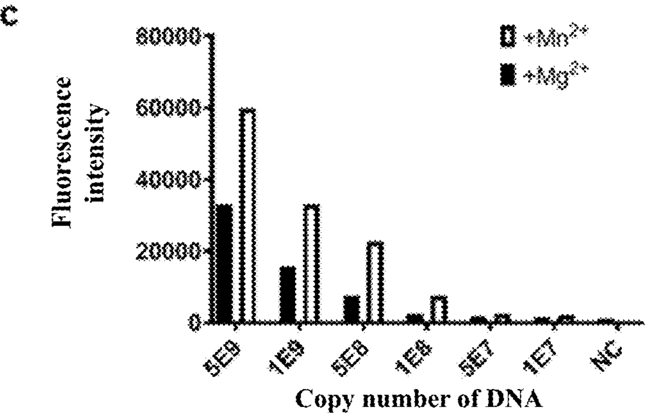

In this example, SARS and MERS viruses were detected with an enhanced cpf1 fluorescence method by a microplate reader, respectively (see FIG. 6 for the results), resulting in the high-sensitivity detection of 1E8 copies of viruses with high sensitivity.

(2) Secondly, according to the RNA samples corresponding to SARS-orf1ab, MERS-upE, and MERS-Orf1 gene fragments as described in 2.1 of Example 2, the molecular weight of the detection fragments was calculated, and gradient dilution was performed to obtain the detection samples containing 1000, 100, 10, and 5 copies per microliter (copy/μL).

The above diluted sample was subjected to a cpf1-specific reaction by the fluorescence method, and detection and interpretation of fluorescence results were performed according to the detection procedure in Example 2. The operation was briefly described as follows: 1 μL of gradient diluted samples were added to a 50 μL of RT-RPA isothermal amplification reaction system for amplification. 10 μL of isothermal amplification products were added into a 20 μL of cpf1 fluorescent nucleic acid detection system (wherein the added crRNA was SARS-O-Crmix for detecting SARS-orf1ab gene, MERS-E-Crmix for detecting MERS-upE gene, or MERS-O-Crmix for detecting MERS-Orf gene as described above), the mixture was blended homogeneously, and reacted at 37° C. for 25 min to interpret the fluorescence results.

Figure 7:
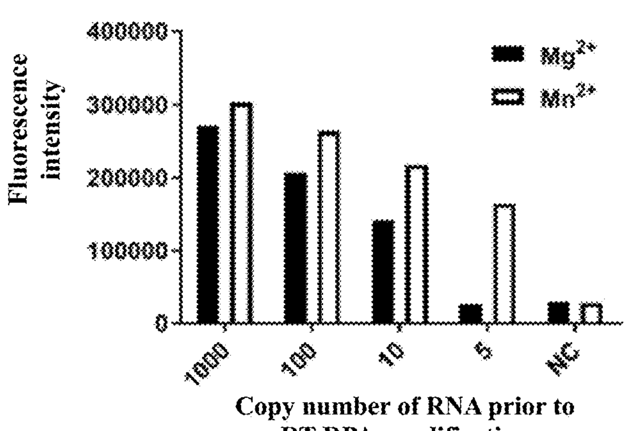
FIG. 7 shows the sensitivity of the enhanced Cpf1 fluorescence detection for the DNAs of the SARS and MERS viruses.
Figure 7:
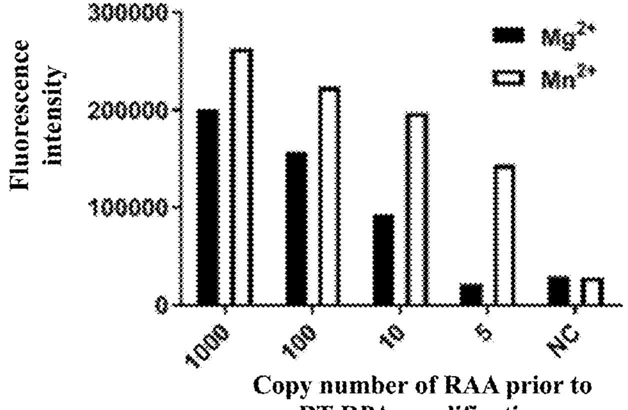
Figure 7:
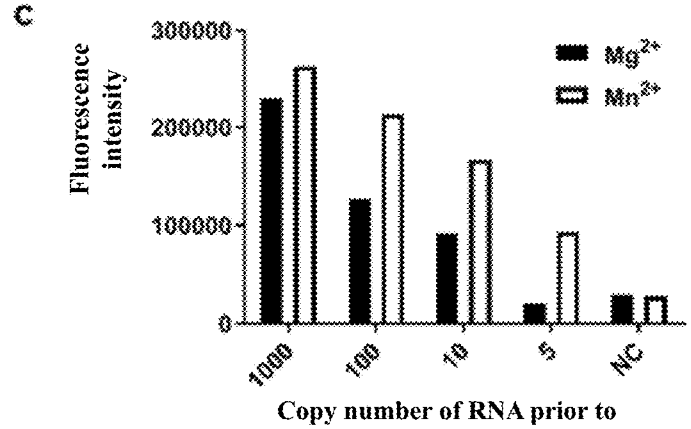

In this example, SARS and MERS virus RNA were detected with a cpf1 fluorescence method by a microplate reader, respectively (see FIG. 7 for the results), resulting in the high-sensitivity detection of 5 copies of viruses with high sensitivity.

Example 4: High-Specificity Detection of Nucleic Acid of Virus Based on cpf1 Fluorescence Method In this example, the following detection was carried out to examine whether the cpf1 fluorescence method can perform a highly specific reaction and effectively distinguish SARS-CoV from MERS virus.

(1) Firstly, the specificity of the viral DNA was detected.

According to the nucleic acid detection segments SARS-orf1ab and MERS-upE of SARS-CoV and MERS virus in the present invention, with reference to the method in Example 2, DNA samples corresponding to the gene sequence of MERS virus (SARS-ORF1ab, MERS-upE, and MERS-Orf1) were prepared.

Referring to Example 2, the above DNA samples were mixed, and to the enhanced Cpf1 detection system were sequentially added 2 μL Buffer, 1 μL Rnase Inhibitors, 1 μL Cpf1, 1 μL ssDNA FQ reporter, 1 μL crRNA (wherein the added crRNA was the above SARS-O-Crmix for detecting SARS-orf1ab gene, MERS-E-Crmix for detecting MERS-upE gene, or MERS-O-Crmix for detecting MERS-Orf gene) and 1 μL detection sample. The components were blended homogeneously and reacted at 37° C. for 30 min. In this assay system, Rnase Inhibitors had a concentration of 40 U/μL, Cpf1 had a concentration of 200 ng/μL, ssDNA DB reporter had a concentration of 25 pM/μL, and crRNA had a concentration of 1 nM/μL.

Figure 8:
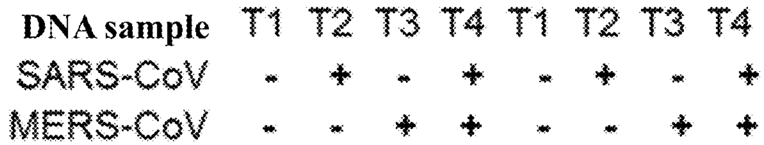
FIG. 8 shows the specificity of the Cpf1 rapid fluorescence detection of the DNAs of the SARS and MERS viruses.
Figure 8:
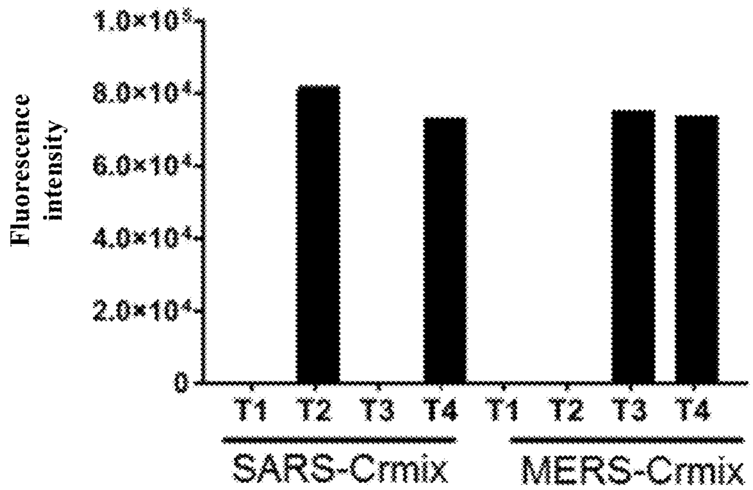
Figure 8:
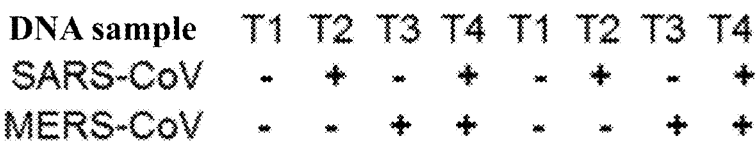
Figure 8:
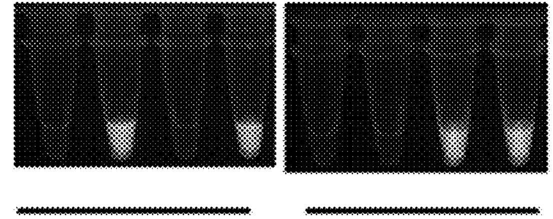

In this example, the activity of the Cpf1 detection system was determined with a fluorescence detection. The fluorescence of the detection reaction was measured by a full-wavelength microplate reader, with an excitation wavelength of 485 nm and an emission wavelength of 520 nm, and the detected fluorescence value at 30 min was read as the reaction value. The detection results were as shown in FIG. 8*a* (T1, T2, T3, and T4 in FIG. 8 are formulated samples, respectively, wherein T1 is DNA known to be free of SARS or MERS-upE genes, T2 is DNA known to contain the SARS gene; T3 is DNA known to contain the MERS-upE gene; T4 is DNA known to contain SARS and MERS-upE genes. Mers-Crmix in FIG. 8 refers to MERS-E-Crmix described above, and SARS-Crmix refers to SARS-O-Crmix described above). Meanwhile, the product after the cpf1 detection reaction for 30 min was placed under a 485 nm laser lamp, and the result could be directly interpreted with the naked eyes. When crRNA specifically recognized the target nucleic acid fragment, the color of the reaction product changed from colorless to fluorescent green; accordingly, if there was no corresponding target nucleic acid to be detected, the reaction product remained colorless. After thecpf1 detection reaction for 30 min, the results were interpreted with the naked eyes under fluorescence and recorded by photography. As shown in FIG. 8*b*, crRNA targeting different gene fragments could effectively and specifically detect the corresponding gene fragments with high specificity and accurate detection results.

(2) Secondly, the specificity of the virus RNA was detected.

According to the nucleic acid detection segments SARS-ORF1ab, MERS-upE, and MERS-Orf1 of SARS-CoV and MERS virus in the present invention, with reference to the method in Example 2, RNA samples corresponding to the gene sequence of MERS virus (SARS-ORF1ab, MERS-upE, and MERS-Orf1) were prepared.

Referring to Example 2, SARS-CoV and MERS virus detection samples were separately amplified by RT-RPA reaction. The RNA samples were mixed, and into the enhanced Cpf1 detection system were sequentially added 2

μL Buffer, 1 μL Rnase Inhibitors, 1 μL Cpf1, 1 μL ssDNA FQ reporter, 1 μL crRNA, and 10 μL detection samples. The components were blended homogeneously and reacted at 37° C. for 30 min. In this assay system, Rnase Inhibitors have a concentration of 40 U/μL, Cpf1 has a concentration of 200 ng/μL, ssDNA DB reporter has a concentration of 25 pM/μL, and crRNA has a concentration of 1 nM/μL.

Figure 9:
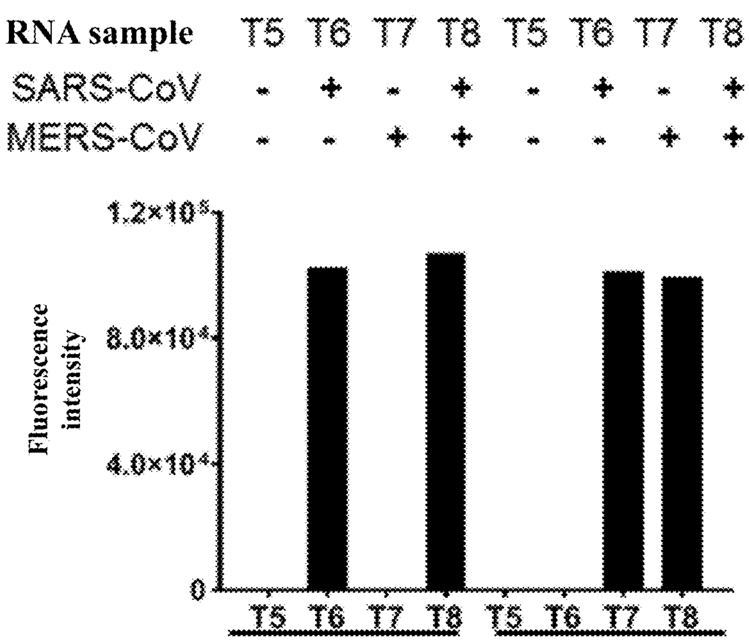
FIG. 9 shows the specificity of the Cpf1 rapid fluorescence detection of RNAs of the SARS and MERS viruses.
Figure 9:
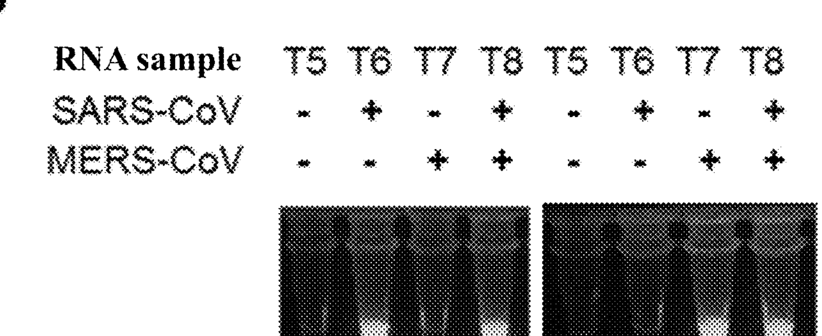

In this example, the activity of the Cpf1 detection system was determined with a fluorescence detection. The fluorescence of the detection reaction was measured by using a full-wavelength microplate reader, with an excitation wavelength of 485 nm and an emission wavelength of 520 nm, and the detected fluorescence value at 30 min was read as the reaction value. The detection results were as shown in FIG. 9*a* (T5, T6, T7, and T8 in FIG. 9 are formulated samples, respectively, wherein T5 is RNA known to be free of SARS or MERS-upE genes, T6 is RNA known to contain the SARS gene; T7 is RNA known to contain the MERS-upE gene; T8 is RNA known to contain SARS and MERS-upE genes. Mers-Crmix in FIG. 9 refers to MERS-E-Crmix, and SARS-Crmix refers to SARS-O-Crmix described above). Meanwhile, the product after the cpf1 detection reaction for 30 min was placed under a 485 nm laser lamp, and the result could be directly interpreted with the naked eyes. When crRNA specifically recognized the target nucleic acid fragment, the color of the reaction product changed from colorless to fluorescent green; accordingly, if there was no corresponding target nucleic acid to be detected, the reaction product remained colorless. After the cpf1 detection reaction for 30 min, the results were interpreted with the naked eyes under fluorescence and recorded by photography. As shown in FIG. 9*b*, crRNA targeting different gene fragments can effectively and specifically detect the corresponding gene fragments with high specificity and accurate detect results.

Example 5: Rapid Detection of Nucleic Acid of Clinical Virus by a Simulated cpf1 Fluorescence Method This example simulated the nucleic acid of clinical tissue samples for rapid detection. This detection did not involve any clinical SARS and MERS virus samples, and all operations were qualified according to relevant laws and regulations and relevant provisions.

In this example, an RNA sample corresponding to SARS-CoV nucleic acid (SARS-orf1ab) and an RNA sample corresponding to the MERS virus nucleic acid (MERS-orf1ab and MERS-upE) in Example 2 were first spotted onto a throat swab to simulate a clinical sample for detection.

(1) Firstly, the virus was inactivated and the viral nucleic acid was released. A rapid nucleic acid release agent purchased from Vazyme Biotech Co., Ltd. was used in this example to obtain pretreated nucleic acids. The steps were as follows: the throat swabs were added to 50 μL of PBS to simulate the dissolution of the virus into a liquid. 3 μL of the sample to be tested was taken, added with 20 μL of a nucleic acid lysis solution and a RNA enzyme inhibitor, allowed to stand at room temperature for 3 min, then added with 20 μL of a neutralization solution, and blended homogeneously for the next detection. In the Cpf1 detection, 5 μL of each sample to be tested was taken and subjected to RT-RPA pre-amplification with the steps same as those in Example 1 to obtain a Cpf1 detection sample.

To the Cpf1 detection system were sequentially added 2 μL Buffer, 1 μL Rnase Inhibitors, 1 μL Cpf1, 1 μL ssDNA FQ reporter, 10 μL RPA sample, and 1 μL crRNA. The components were blended homogeneously and reacted at 37° C. for 25 min.

Figure 10:
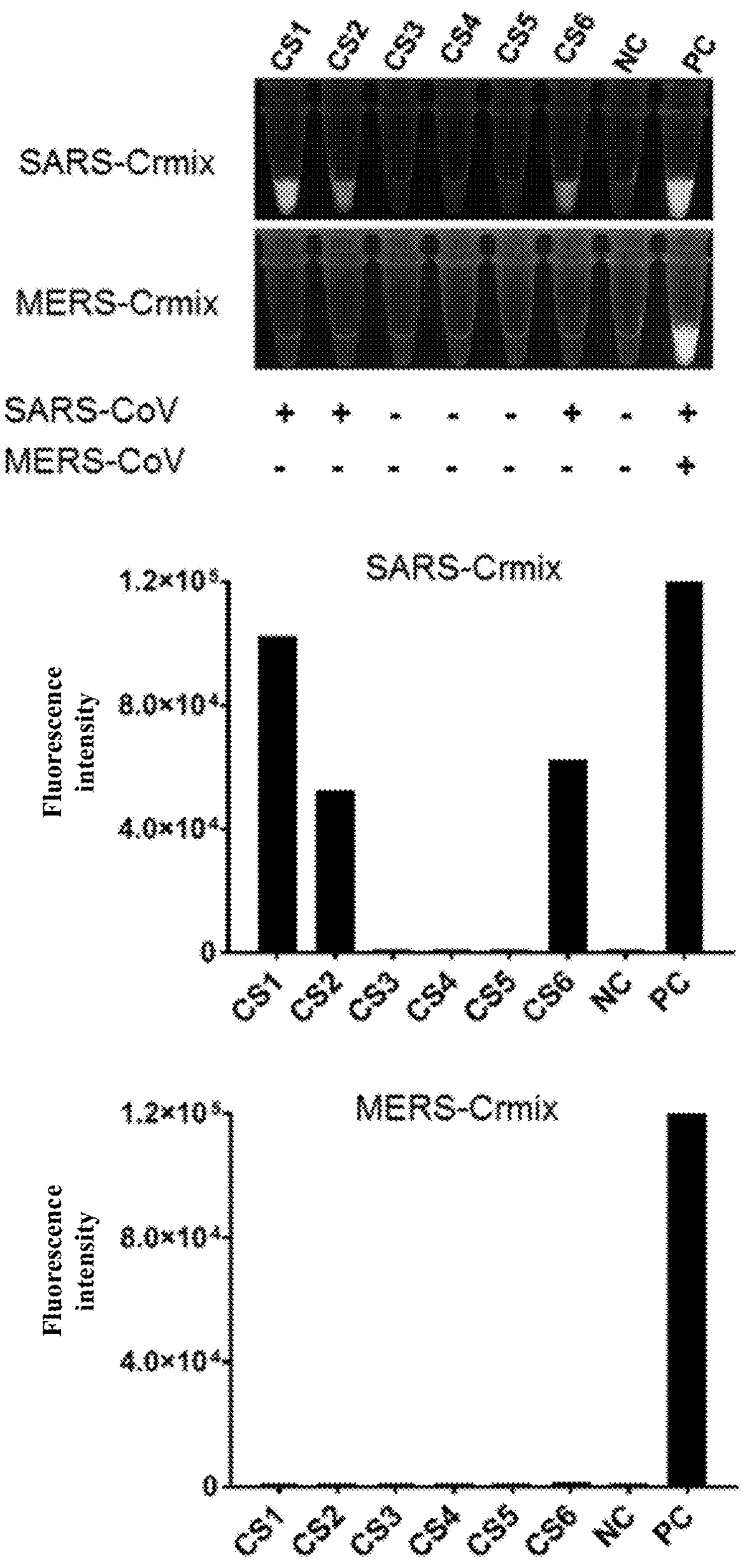
FIG. 10 shows the fluorescence results of a simulated detection of clinical nucleic acid samples.

In this example, the cpf1 detection results were observed with the naked eyes under a fluorescent lamp or directly determined by a microplate reader. As shown in FIG. 10, the simulated clinical negative and positive samples could be effectively determined and detected by a microplate reader with the cpf1 fluorescence method of the present invention. Similarly, under light, the simulated clinical negative and positive samples could be effectively determined with the naked eyes under a fluorescent lamp (FIG. 10, CS1-CS6 in the figure were formulated samples respectively, wherein CS1, CS2, and CS6 were samples known to be positive for SARS-CoV, and the rest were samples known to be negative for SARS and negative for MERS. Mers-Crmix in the figure referred to MERS-E-Crmix, and SARS-Crmix referred to the above-mentioned SARS-O-Crmix). It could be seen that the detection method in the present invention was fast, visual, low in cost, and simple in operation, while the accuracy of the results obtained was high.

Figure 13:
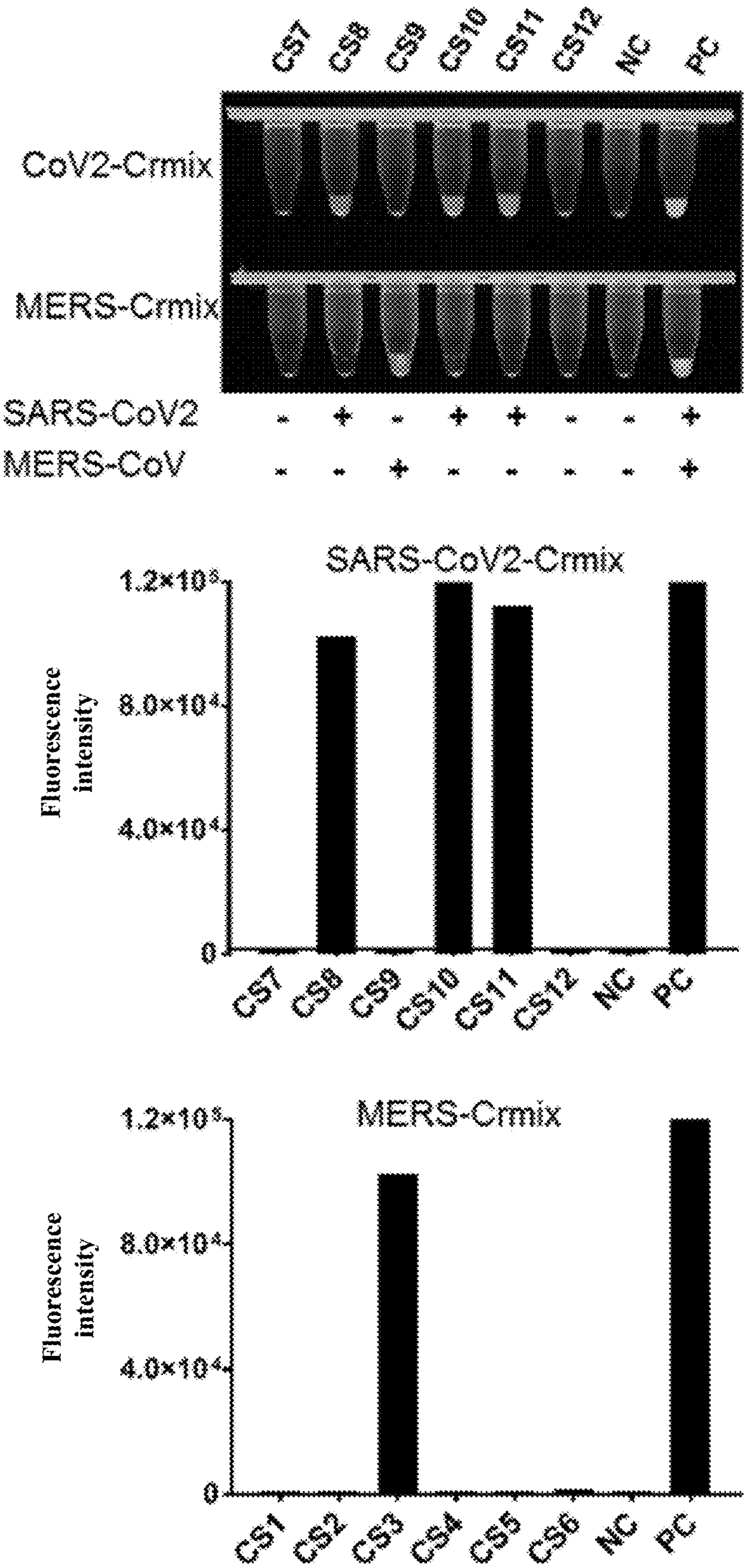
FIG. 13 shows the fluorescence results of a simulated detection of clinical nucleic acid samples.

(2) Similarly, samples of CS7 to CS12 were prepared in simulated clinical mode, in which CS8, CS10, and CS11 are samples known to be SARS-CoV-2 positive, CS9 is a sample known to be MERS-CoV positive, and the rest were samples known to be SARS-CoV-2 negative and MERS-CoV negative. The detection was performed by a method similar to that in (1) above, and then the cpf1 detection results were observed with the naked eyes under a fluorescent lamp or directly determined by a microplate reader. As shown in FIG. 13 (MERS-Crmix is MERS-E-Crmix in the figure), the simulated clinical negative and positive samples could be effectively determined and detected by a microplate reader with the cpf1 fluorescence method of the present invention. It could be seen that the detection method of the present invention is high in accuracy.

In addition, combining the results of the above examples, it could be further seen that when the ligand ion of Cpf1 in the reaction system was replaced with a manganese ion, the signal intensity of the detection could be significantly increased when detecting nucleic acids of different viruses (SARS-CoV, MERS-CoV, SARS-CoV-2, etc.), thus indicating that the manganese ion system had universality.

Example 6: Rapid Detection of Different Genes of Nucleic Acid of Clinical SARS-CoV-2 Virus by Simulated cpf1 Fluorescence Method This example simulated rapid detection of nucleic acids of clinical tissue samples. This detection did not involve any clinical SARS-CoV-2 sample, and all operations were qualified according to relevant laws and regulations and relevant provisions.

In this example, firstly, an RNA sample corresponding to the nucleic acid of the SARS-CoV-2 virus (CoV2-E-gene, CoV2-S-gene, CoV2-M-gene, and CoV2-N-gene) was spotted onto a throat swab to simulate a clinical sample for detection.

(1) Firstly, the virus was inactivated and the viral nucleic acid was released. A rapid nucleic acid release agent purchased from Vazyme Biotech Co., Ltd. was used in this example to obtain pretreated nucleic acids. The steps were as follows: the throat swab was added into 50 μL of PBS to simulate the dissolution of the virus into a liquid. 3 μL of the sample to be tested was taken, added with 20 μL of a nucleic acid lysis solution and an RNA enzyme inhibitor, allowed to stand at room temperature for 3 min, then added with 20 μL of a neutralization solution, and blended homogeneously for the next detection. In the Cpf1 detection, 5 μL of each sample to be tested was taken and subjected to RT-RPA pre-amplification with the steps same as those in Example 1 to obtain a Cpf1 detection sample.

To the Cpf1 detection system were sequentially added 2 μL Buffer, 1 μL Rnase Inhibitors, 1 μL Cpf1 or Cpf1 mutated protein, 1 μL ssDNA FQ reporter, 10 μL RPA sample, and 1 μL crRNA, 1 μL $Mn^{2+}$ or $Mg^{2+}$, the components were blended homogeneously and reacted at 37° C. for 25 min.

In this example, the detection results of cpf1 and mutation thereof could be directly determined by a microplate reader. As shown in FIGS. 15, 16, 17, and 18, different cpf1 mutants in the present invention could detect the S gene, M gene, N gene, and E gene of SARS-CoV2 by a microplate reader. Effective detection could be performed by adding $Mg^{2+}$ and $Mn^{2+}$ ions, but the addition of $Mn^{2+}$ enabled signals to be stronger, and the manganese ion system had universality.

REFERENCES

1. R, B., et al., CRISPR provides acquired resistance against viruses in prokaryotes. Science (New York, N.Y.), 2007. 315(5819): p. 1709-12.
2. L A, M. and S. E J, CRISPR interference limits horizontal gene transfer in staphylococci by targeting DNA. Science (New York, N.Y.), 2008. 322(5909): p. 1843-5.
3. B, Z., et al., Cpf1 is a single RNA-guided endonuclease of a class 2 CRISPR-Cas system. Cell, 2015. 163(3): p. 759-71.
4. I, F., et al., The CRISPR-associated DNA-cleaving enzyme Cpf1 also processes precursor CRISPR RNA. Nature, 2016. 532(7600): p. 517-21.
5. J S, C., et al., CRISPR-Cpf1 target binding unleashes indiscriminate single-stranded DNase activity. Science (New York, N.Y.), 2018. 360(6387): p. 436-439.
6. González, J M. et al., A comparative sequence analysis to revise the current taxonomy of the family Coronaviridae, Gomez-Puertas P, Cavanagh D, Gorbalenya A E, Enjuanes L. Arch Virol. 2003; 148(11): p. 2207-35.
7. Ksiazek, T G. et al., A novel coronavirus associated with severe acute respiratory syndrome. N Engl J Med, 2003, 348(20): p. 1953-1966
8. Zaki, A M. et al., Isolation Of A Novel Coronavirus From A Man With Pneumonia In Saudi Arabia. N Engl J Med, 2012, 367(19): p. 1814-20.

9 O, P., et al., DNA detection using recombination proteins. PLoS biology, 2006. 4(7): p. e204.

What is claimed is:

1. A nucleic acid detection kit, comprising a Cpf1 detection system comprising: a guide RNA, a mutated Cpf1 protein, a nucleic acid probe, and a manganese ion-containing solution;

wherein the mutated Cpf1 protein comprises the amino acid sequence of SEQ ID NO: 54 having one or more substitutions selected from the group consisting of T148R, T152R, G532R and K538R.

2. The nucleic acid detection kit of claim 1, wherein the nucleic acid probe is a single-stranded DNA probe.

3. The nucleic acid detection kit of claim 1, wherein the guide RNA is capable of guiding the mutated Cpf1 protein to specifically bind to a target nucleic acid.

4. The nucleic acid detection kit of claim 1, wherein:

(i) the manganese ion-containing solution has a concentration of manganese ions of 5-600 mM;

(ii) the nucleic acid probe has a concentration of 1-100 μmol/μL;

(iii) the Cpf1 protein has a concentration of 20-1,000 ng/μL;

(iv) the guide RNA has a concentration of 0.1-50 μM; or, (v) the manganese ion-containing solution is a manganese sulfate solution, a manganese chloride solution, or a manganese acetate solution;

optionally, the nucleic acid detection kit further comprises an RNase inhibitor and a buffer.

5. A method for detecting a nucleic acid, comprising:

(a) contacting a sample to be tested containing the nucleic acid with the Cpf1 detection system in the nucleic acid detection kit of claim 1; and, (b) detecting a signal indicative of the presence of the nucleic acid.

6. The nucleic acid detection kit of claim 1, wherein the mutated Cpf1 protein comprises the amino acid sequence of SEQ ID NO: 54 having one substitution selected from the group consisting of T148R, T152R, G532R and K538R.

7. The nucleic acid detection kit of claim 1, wherein the mutated Cpf1 protein comprises the amino acid sequence of SEQ ID NO: 54 having substitutions of T152R and G532R, or, the mutated Cpf1 protein comprises an amino acid sequence of SEQ ID NO: 54 having substitutions of T152R, G532R and K538R.

8. The nucleic acid detection kit of claim 1, wherein the mutated Cpf1 protein comprises the amino acid sequence of SEQ ID NO: 54 having substitutions of T148R, T152R, G532R and K538R.

9. The nucleic acid detection kit of claim 1, wherein the mutated Cpf1 protein is encoded by a nucleotide sequence selected from the group consisting of SEQ ID NO: 36, SEQ ID NO: 37, SEQ ID NO: 38, and SEQ ID NO: 39.

10. The nucleic acid detection kit of claim 1, wherein the mutated Cpf1 protein is encoded by a nucleotide sequence of SEQ ID NO: 40 or SEQ ID NO: 41.

11. The nucleic acid detection kit of claim 2, wherein the nucleic acid probe comprises a fluorescent label.

12. The nucleic acid detection kit of claim 11, wherein the nucleic acid probe comprises a fluorescent group and a fluorescence quenching group at its 5' and 3' terminals, respectively.

13. The nucleic acid detection kit of claim 12, wherein the fluorescent group is selected from the group consisting of 6-FAM, TET, CY3, CY5, and ROX; or, the fluorescence quenching group is selected from the group consisting of BHQ1, BHQ2, and BHQ3.

14. The nucleic acid detection kit of claim 3, wherein the guide RNA is a crRNA.

15. The nucleic acid detection kit of claim 14, wherein the crRNA is capable of detecting a viral nucleic acid.

16. The nucleic acid detection kit of claim 15, wherein the crRNA is capable of detecting a SARS-associated coronavirus or MERS-COV virus.

17. The nucleic acid detection kit of claim 16, wherein the SARS-associated coronavirus is a SARS-COV or SARS-COV-2 coronavirus.

18. The nucleic acid detection kit of claim 17, wherein the crRNA is capable of detecting a target selected from the group consisting of: an orf1ab gene of the SARS-CoV coronavirus, an orf1a gene of the MERS-COV virus, an upE gene of the MERS-COV virus, a E gene of the SARS-COV-2 coronavirus, an S gene of the SARS-COV-2 coronavirus, an M gene of the SARS-COV-2 coronavirus, and an N gene of the SARS-CoV-2 coronavirus;

wherein the nucleotide sequence of the orf1ab gene is set forth in SEQ ID NO: 11, the nucleotide sequence of the orf1a gene is set forth in SEQ ID NO: 12, the nucleotide sequence of the upE gene is set forth in SEQ ID NO: 13, and the nucleotide sequence of the E gene is set forth in SEQ ID NO: 46; the nucleotide sequence of the S gene of the SARS-COV-2 coronavirus is set forth in SEQ ID NO: 79; the nucleotide sequence of the M gene of the SARS-COV-2 coronavirus is set forth in SEQ ID NO: 80; and the nucleotide sequence of the N gene of the SARS-COV-2 coronavirus is set forth in SEQ ID NO: 81.

19. The nucleic acid detection kit of claim 18, wherein the nucleotide sequence of the crRNA is selected from the group consisting of SEQ ID NOs: 1-10, SEQ ID NO: 47, SEQ ID NO: 48, SEQ ID NO: 53, and SEQ ID NOs: 56-72.

20. The method of claim 5, wherein:

(i) the nucleic acid in the sample to be tested is released by using a nucleic acid rapid release reagent;

(ii) the nucleic acid is obtained by amplifying the nucleic acid in the sample to be tested;

(iii) a reaction temperature of the Cpf1 detection system is 37 ±5° C.; or, (iv) a reaction time of the Cpf1 detection system is 25 ±5 min;

optionally, the method further comprising: (c) reading a result.

* * * * *

SEQUENCE LISTING

```
<160> NUMBER OF SEQ ID NOS: 81

<210> SEQ ID NO 1
<211> LENGTH: 44
<212> TYPE: RNA
<213> ORGANISM: Artificial Sequence
<220> FEATURE:
<223> OTHER INFORMATION: SARS-O-Cr1

<400> SEQUENCE: 1

uaauuucuac uaaguguaga uuacagguua gcuaacgagu gugc                        44


<210> SEQ ID NO 2
<211> LENGTH: 44
<212> TYPE: RNA
<213> ORGANISM: Artificial Sequence
<220> FEATURE:
<223> OTHER INFORMATION: SARS-O-Cr2

<400> SEQUENCE: 2

uaauuucuac uaaguguaga uucaagcugu uacagccaau guaa                        44


<210> SEQ ID NO 3
<211> LENGTH: 44
<212> TYPE: RNA
<213> ORGANISM: Artificial Sequence
<220> FEATURE:
<223> OTHER INFORMATION: SARS-O-Cr3

<400> SEQUENCE: 3

uaauuucuac uaaguguaga uaacugaugg uaauaagaua gcug                        44


<210> SEQ ID NO 4
<211> LENGTH: 44
<212> TYPE: RNA
<213> ORGANISM: Artificial Sequence
<220> FEATURE:
<223> OTHER INFORMATION: MC-E-crRNA1
```

<400> SEQUENCE: 4
uaauuucuac uaaguguaga ugacauaugg aaaacgaacu augu 44

<210> SEQ ID NO 5
<211> LENGTH: 44
<212> TYPE: RNA
<213> ORGANISM: Artificial Sequence
<220> FEATURE:
<223> OTHER INFORMATION: MC-E-crRNA2

<400> SEQUENCE: 5
uaauuucuac uaaguguaga uuccaagaac gaauaggguu guuc 44

<210> SEQ ID NO 6
<211> LENGTH: 44
<212> TYPE: RNA
<213> ORGANISM: Artificial Sequence
<220> FEATURE:
<223> OTHER INFORMATION: MC-E-crRNA3

<400> SEQUENCE: 6
uaauuucuac uaaguguaga ucuaugaaca acccuauucg uucu 44

<210> SEQ ID NO 7
<211> LENGTH: 44
<212> TYPE: RNA
<213> ORGANISM: Artificial Sequence
<220> FEATURE:
<223> OTHER INFORMATION: MC-E-crRNA4

<400> SEQUENCE: 7
uaauuucuac uaaguguaga ucauaugucc aaagagagac uaau 44

<210> SEQ ID NO 8
<211> LENGTH: 44
<212> TYPE: RNA
<213> ORGANISM: Artificial Sequence
<220> FEATURE:
<223> OTHER INFORMATION: MC-O-Cr1

<400> SEQUENCE: 8
uaauuucuac uaaguguaga uacuuaugca aacauagucu acga 44

<210> SEQ ID NO 9
<211> LENGTH: 44
<212> TYPE: RNA
<213> ORGANISM: Artificial Sequence
<220> FEATURE:
<223> OTHER INFORMATION: MC-O-Cr2

<400> SEQUENCE: 9
uaauuucuac uaaguguaga ugucagcgcu gauugcaguu gcaa 44

<210> SEQ ID NO 10
<211> LENGTH: 44
<212> TYPE: RNA
<213> ORGANISM: Artificial Sequence
<220> FEATURE:
<223> OTHER INFORMATION: MC-O-Cr3

<400> SEQUENCE: 10
uaauuucuac uaaguguaga ucaacugcaa ucagcgcuga cgaa 44

<210> SEQ ID NO 11
<211> LENGTH: 444

<212> TYPE: DNA
<213> ORGANISM: Artificial Sequence
<220> FEATURE:
<223> OTHER INFORMATION: SARS-Orf1ab

<400> SEQUENCE: 11
taatacgact cactataggt ctagaaataa ttttgtttaa ctttaagaag gagatatacc 60
atgctaacat gcttaggata atggcctctc ttgttcttgc tcgcaaacat aacacttgct 120
gtaacttatc acaccgtttc tacaggttag ctaacgagtg tgcgcaagta ttaagtgaga 180
tggtcatgtg tggcggctca ctatatgtta aaccaggtgg aacatcatcc ggtgatgcta 240
caactgctta tgctaatagt gtctttaaca tttgtcaagc tgttacagcc aatgtaaatg 300
cacttctttc aactgatggt aataagatag ctgacaagta tgtccgcaat ctacaacaca 360
ggctctatga gtgtctctat agaaataggg atgttgatca tgaattcgtg gatgagtttt 420
acgcttacct gttttttga attc 444

<210> SEQ ID NO 12
<211> LENGTH: 345
<212> TYPE: DNA
<213> ORGANISM: Artificial Sequence
<220> FEATURE:
<223> OTHER INFORMATION: MERS-upE

<400> SEQUENCE: 12
taatacgact cactataggt ctagaaataa ttttgtttaa ctttaagaag gagatatacc 60
atgctgtttt cgtgcctgca acgcgcgatt cagttcctct tcacataatc gccccgagct 120
cgcttatcgt ttaagcagct ctgcgctact atgggtcccg tgtagaggct aatccattag 180
tctctctttg gacatatgga aaacgaacta tgttaccctt tgtccaagaa cgaatagggt 240
tgttcatagt aaactttttc atttttaccg tagtatgtgc tataacactc ttggtgtgta 300
tggctttcct tacggctact agattatgtg tgtttttttg aattc 345

<210> SEQ ID NO 13
<211> LENGTH: 449
<212> TYPE: DNA
<213> ORGANISM: Artificial Sequence
<220> FEATURE:
<223> OTHER INFORMATION: MERS-Orf1a

<400> SEQUENCE: 13
taatacgact cactataggg agatctagaa ataattttgt ttaactttaa gaaggagata 60
taccatgact attcccacac agttgttccc actcttattt gtgactatgg ccttcgttat 120
gttgttggtt aaacacaaac acaccttttt gacacttttc ttgttgcctg tggctatttg 180
tttgacttat gcaaacatag tctacgagcc cactactccc atttcgtcag cgctgattgc 240
agttgcaaat tggcttgccc ccactaatgc ttatatgcgc actacacata ctgatattgg 300
tgtctacatt agtatgtcac ttgtattagt cattgtagtg aagagattgt acaacccatc 360
actttctaac tttgcgttag cattgtgcag tggtgtaatg tggttgtaca cttatagcat 420
tggagaagcc tcaagctttt tttgaattc 449

<210> SEQ ID NO 14
<211> LENGTH: 3924
<212> TYPE: DNA
<213> ORGANISM: Artificial Sequence
<220> FEATURE:
<223> OTHER INFORMATION: AsCpf1

<400> SEQUENCE: 14

```
atgactcagt tcgaggggtt caccaatttg taccaggtct ctaagacact tcgctttgag     60
cttatccctc agggcaagac gctgaagcat atccaggagc aaggatttat cgaggaggac    120
aaggcacgta atgaccacta taaagagctg aaaccgatca ttgatcgcat ttacaagacc    180
tatgcagatc agtgtctgca gcttgtgcaa ttagattggg aaaatctgag cgccgcaatc    240
gactcctatc gtaaagagaa gactgaagaa acacgtaatg cattaattga agaacaggcc    300
acgtatcgca atgctatcca cgattatttt attgggcgca ccgacaattt aactgatgcc    360
atcaataagc gtcacgcaga gatctacaag ggacttttta aagccgaatt atttaatggc    420
aaggttttaa aacagcttgg tactgtaaca acaacagagc acgagaatgc ccttctgcgc    480
tcgttcgata agtttaccac gtacttctcg ggcttttacg aaaaccgcaa aaacgtgttc    540
tcggcggagg acatctctac agctatccca caccgtattg tacaagataa cttccccaaa    600
tttaaggaga attgtcacat tttcacgcgt ttgattactg cggtaccgtc tttacgtgag    660
catttcgaaa acgttaagaa ggcaattggc atttttgtca gcacgtctat tgaagaagtg    720
ttctcgtttc ccttctacaa tcagctgttg actcaaacgc agatcgactt atataaccag    780
ctgttgggtg gcatctcacg cgaggcaggc acagaaaaaa ttaaaggcct gaacgaggtc    840
ttgaatttgg ctatccagaa gaacgatgag accgcgcaca tcattgcttc cttacctcat    900
cgctttattc cgttgtttaa acaaattctt agtgatcgta atactttatc cttcatctta    960
gaggaattta aatccgacga ggaggttatt cagtccttct gcaaatataa aactctgtta   1020
cgcaacgaga acgtgcttga aaccgcggag gctttattca acgagctgaa ctcgattgac   1080
ttgacacata ttttcatctc acacaagaaa ctggaaacga tttcgtcagc cctttgcgac   1140
cactgggata ctctgcgtaa cgcattatat gaacgtcgca tttccgaatt gacaggaaaa   1200
atcactaaga gcgcaaagga gaaggtacag cgttcgctga aacatgaaga catcaacctt   1260
caggagatta tctctgcggc gggcaaagaa cttagtgaag catttaagca aaaaaccagt   1320
gagatcctta gccatgcgca cgctgctctt gaccaaccac ttccgacaac gctgaaaaaa   1380
caggaggaaa aggagattct gaagagccag ctggattctt tacttggact ttatcatttg   1440
ttggattggt ttgccgtgga cgaaagtaac gaagtagatc ccgaattttc ggcgcgcctt   1500
accggcatca agttggaaat ggaaccctca ctgtcgttct acaataaagc ccgcaactac   1560
gccactaaaa agccctattc ggtagaaaag tttaagttga actttcagat gccaactctt   1620
gcttcaggat gggatgtgaa caaagaaaag aataacggag ctattttgtt cgttaagaac   1680
ggtctgtatt atcttggaat catgccgaaa cagaagggac gttacaaagc gctttcgttc   1740
gaaccaacag aaaagacctc cgaggggttc gataagatgt attacgacta ttttccggac   1800
gcagcaaaaa tgatcccgaa gtgctcaacg cagctgaaag ctgtgactgc gcattttcaa   1860
actcacacga cccccatttt gttatccaat aatttcatcg aacctttgga aattacgaag   1920
gagatctatg acttaaacaa tcctgaaaaa gagccgaaaa aatttcaaac cgcgtacgcc   1980
aagaaaaccg gggaccaaaa agggtaccgc gaagctcttt gcaaatggat cgacttcact   2040
cgtgattttc tttctaagta tacgaaaact acgtcgattg acttatcgag tttacgccca   2100
tcctctcaat acaaggatct gggggaatat tatgccgaac tgaatcctct tttatatcac   2160
atcagcttcc aacgcatcgc cgaaaaagag attatggacg cggtcgagac gggaaagctt   2220
tacttatttc aaatctataa taaagatttc gccaaaggtc atcacgggaa acccaatctg   2280
cacacccttt attggacagg tctgttctct cccgaaaact tagcgaaaac atccattaag   2340
```

```
cttaacgggc aggcagagtt gttctatcgt cccaaatccc gtatgaagcg catggcacac   2400

cgtcttggag aaaaaatgct taacaaaaag cttaaagacc aaaaaactcc gatccctgat   2460

accctttacc aagagttata tgattatgtc aatcatcgct tatcacatga cttgtccgac   2520

gaggcacgcg cacttttacc aaacgtcatc acgaaggaag tcagtcacga aatcattaag   2580

gatcgtcgtt tcacatccga taaatttttt tttcacgtac caattacttt gaactatcag   2640

gctgccaata gtccgagcaa gttcaatcaa cgtgtaaacg cgtacttaaa ggagcacccc   2700

gaaacccccca ttatcgggat cgaccgcggc gaacgcaatc ttatctatat cacggttatc   2760

gattctactg gaaaaatttt agagcagcgt tccctgaaca ccattcaaca gtttgattat   2820

cagaagaaac ttgacaatcg cgaaaaagaa cgtgttgcgg cgcgtcaagc atggagcgtt   2880

gttggtacaa tcaaagacct taaacaaggt tacttatcgc aggtcatcca cgagatcgtt   2940

gacctgatga tccactacca agctgtcgtc gtacttgaaa atcttaattt cggcttcaag   3000

tccaaacgta caggaattgc ggaaaaggct gtataccaac aattcgaaaa aatgcttatc   3060

gataagctta actgccttgt gttgaaagat taccctgcgg aaaaagtcgg aggtgtatta   3120

aacccatatc aattgaccga tcaattcact tcatttgcca aaatgggcac gcagtcaggg   3180

tttttgttct atgtaccagc tccatatacc tctaagattg atccgttaac gggctttgtt   3240

gatcctttcg tctggaagac catcaaaaac catgaaagcc gcaaacactt ccttgagggc   3300

tttgactttc ttcactacga tgtaaagacc ggagatttca tcttacactt caaaatgaac   3360

cgcaatctgt ctttccaacg tggtttacct ggatttatgc ctgcgtggga catcgtattc   3420

gagaaaaatg aaactcagtt tgatgcaaaa ggcacgccgt ttatcgccgg aaagcgcatt   3480

gtaccagtta tcgagaacca ccgtttcaca gggcgttacc gcgacctgta ccccgcgaac   3540

gaattgatcg cgctgttaga agaaaaggga atcgttttcc gtgacgggtc caacatctta   3600

cccaagttac ttgaaaacga cgacagtcac gcaatcgaca caatggttgc tttaatccgc   3660

tccgttctgc aaatgcgtaa cagcaacgct gcgactggtg aggactacat taatagcccg   3720

gtccgcgacc ttaacggcgt atgtttcgac tcccgtttcc agaatcctga gtggcccatg   3780

gacgcagacg caaatggggc ctaccatatt gcgctgaaag gtcaattact tctgaatcac   3840

ttgaaggaat ctaaggacct taaactgcag aatgggatct caaaccaaga ctggttagcg   3900

tacattcagg aattacgtaa ctag                                         3924
```

```
<210> SEQ ID NO 15
<211> LENGTH: 3729
<212> TYPE: DNA
<213> ORGANISM: Artificial Sequence
<220> FEATURE:
<223> OTHER INFORMATION: BbCpf1

<400> SEQUENCE: 15

atgaaaaagt ttaccaatct gtatccggtt caaaaaacac ttcgttttga acttatcccg     60

caaggcaata cctctaaaca tctttgcaaa attattcagg aggacgagca gatcgcagag    120

gactcgcaag aagtgaaaaa attattagac cgttatcata aagagttcat cgcaattgct    180

ttaagcagct tccctacgtc tcctttagcg aaagaaatta tcccgaaact gaaagagttt    240

gctcaaatcc gtgctacagg ggatgcaaag cagatttcaa caattcaaga tgaacttcgt    300

gagctggtgg ttaaaggttt caagggggag ggggagcaag aacgtcgtta caaaatcttg    360

atcggagcaa aggggaatcc aaacgccgat gaactgttta acactgagtt gattaacttt    420
```

-continued

```
cttaaagatc cggctgagca agccctggta aaaaagtttc agaaacatac tggttatttc    480
ttgggattta acgaaaatcg caagaacatg tactcggcga aggctcagag tacggctatt    540
gcgtatcgct taattcatga gaacttgcca cgctttcttg acaatattac aacttacgaa    600
aaagtcaaga catacctgaa agaggagatc cctcagttgg agaaggaact ggtacgcgct    660
ggggcgagcc ttgtaagtca tgtcgacagt gtcttcacaa tcgacttttt tttagaggtg    720
tttacgcagt ccggcattga ccagtacaac gctcttattg gaaaaattgt caaccaggaa    780
caaggggagg tgaaaggatt aaatgagcgc atcaatttat acaatcaaca acataagcaa    840
gaggcgaagc tgccactttt taaacctttg tacaaacaga ttttaagcga tcgcgagcaa    900
ttgtcttggc ttgccgaagc atataattct gacaaagatt tattggactc gatccagaaa    960
tattatcaac tgttaatcga caaccaaatc tttgaacgta ttccgcgcct gatgcacacg   1020
ctggaaaagg caccgttaga taagatttgg atcacttacg atacgcaact gacaagtatc   1080
tcaaacacac tttacggctc ttggcgcgtc atcggtgagg ctctgggccg taacgctaag   1140
agtgagaagg agcgtaaatc atcgcaaaaa aaggcgttaa attactccct ggagtccatt   1200
aatcaggcca tcgccaagat gcccagcgat gaggagcttc cacctatcca gaaatacttt   1260
atcgcacttg ggagtaaccc gtccaaaaaa gacgctagct ccggtacgtt agtagataaa   1320
gtccgttcgt catataaagc ctgtcaagat attcttacaa atcctgatca tacgggcaag   1380
aaacttatcc aagacaaaaa gcaagttgat ctgttaaagc aattactgga tgacttattg   1440
atcttacagc gtttcatcaa acctttgctg tatagcaata acgagaatga gactcacaaa   1500
gatgaagttt tctatacaga attaacggat atcatggatt tgcttaatcc tattgtagga   1560
ctgtataaca aagtacgcaa ttatttgact caaaagccat attcgactga aaagtttaag   1620
atcaatttca aatcatcgtc cctgttggcg ggttgggacc gcaacaagga gaaagacaac   1680
ttaggggtaa tcttgaaacg cgaagataaa tactaccttg ctattatgga caaggcacac   1740
aacgccacat ttaaaaacaa gtcacttcct actcaaggcg aatgttacga gaaaatggaa   1800
tataagcttc tgccgggagc caataaaatg ctgccgaagg tatatatcac ctcgaaaaaa   1860
ggtatcgaat ccttccatcc atctgaagaa ttacaaaaaa agtacaaatt gggaacgcac   1920
aagaaaggcg cttcgttcaa cctgagcgac atgcgtgcat tgatcgatta cttcaaagaa   1980
tccttggaga agcacgagga gcattcacaa tttggattcc acttttcgga cacgagtacc   2040
tacgaagaca tttctggatt ttaccgtgaa gttgagcagc aggcttataa aattacgttc   2100
cgtaaagtat cggtcgaata catcgatcaa ttggttaacg aaggcaagct ttatctgttc   2160
cagatttata acaaagattt ttctccctat tctaaaggca cacctaattt acacactttg   2220
tactggaaga tgttgtttga tcccgcgaac ttacaggata ttgtttataa gttgaatggt   2280
gaggcggaag tatttttttcg caaaaagtcg ctgcagtacg accgtcctac acatccaaaa   2340
ggccaaccta tcaataagaa aagtttgctg aatgaggggg aaacatccct tttcgactat   2400
gaccttatca aggaccgccg ctttactgta gacaaatttc agtttcatgt ccctattacg   2460
atgaatttca aggccacgca aggtacaaag gtcaaccaaa tggtccagga ggaggtcaag   2520
aaatccaaag gattccactt gatcggcatc gatcgcggag aacgcaacct tttatacatc   2580
gtcgtgatca atgaacgcgg ggagatcatt gagcagtgtt cattaaacaa gattgtgaat   2640
acataccagg aaaaggaaca caccgttgat tataaagctc tgttagagaa acgctcacag   2700
tctcgtcttg aggagcgcaa gtcgtggcaa actatcgaaa atatcaagga gttaaagggc   2760
ggatacttat cacaagttgt gcacaaaatc gctcagttga tgatcaaata taacgcaatt   2820
```

```
gccgttctgg aggacttaaa cttcggtttc attcgtactc gcaagaagtt tgaattttcg   2880
gtgtatcagg agttcgagaa gaaactgatc gataaattgg gttacgtggt agacaagaaa   2940
gccccgattc agcaggaggg tggtttactt caagcttatc agttaaccgc cccattcaag   3000
tcattccgtg agatggggaa acagaacggt tttttgtttt acgtacccgc gtggaacaca   3060
agcgcaatcg atccgcgtac cggatttgtc aatttactgg acacacgcta tgaatcgatc   3120
gcaaaaacca aagagcttat taagaaattg aaagacattc gttacaatag ccaaaaggac   3180
tggttcgaaa tcgatcttga ctataatgcc tttgggaacc gtgcgaaggg ttctcgctcg   3240
aaatggcgct tatgtagcta cggcgaacgt attgagcaca ctcgtaaaca ggatagtaat   3300
ggtcaagagg agagcgattc gatggtagta ttgacggaag catttaaaga tgtctttacg   3360
aagtatcaga tcgattaccg cgagaatctg aaggaacagt tacttctgca gtcagataaa   3420
gctttttttg tggatttcct gagcctgtta cgtttgacgc tgcaactgcg taacagttta   3480
tccaactccc ttattgacta tattctttcg ccggtagccg acgagaatgg ggagtttttt   3540
gactcgcgta aagcccttag taatgagcca caggatgctg acgccaacgg tgcataccac   3600
attgctttaa agggtttgtg ggtattggat aaaatccgta aaacggagaa ggttacgcca   3660
gctaagttgg cgctttccaa ccaggaatgg ttgtcgtttg cccaagagaa gcccttttc    3720
aatgagtga                                                           3729
```

<210> SEQ ID NO 16
<211> LENGTH: 3789
<212> TYPE: DNA
<213> ORGANISM: Artificial Sequence
<220> FEATURE:
<223> OTHER INFORMATION: BoCpf1

<400> SEQUENCE: 16

```
atgcgcaagt tcaacgagtt cgtcggattg taccctattt ctaaaacctt acgttttgag     60
cttaagccga ttggtaagac gttggagcat attcagcgta ataaactttt ggagcatgac    120
gcggtacgcg ctgatgatta cgtaaaggtg aagaaaatta ttgacaaata tcacaaatgt    180
ttgattgacg aagcactgtc tggcttcacc tttgacacgg aagcagacgg tcgctcgaac    240
aatagtcttt ctgagtacta cctgtattac aatctgaaaa aacgcaacga acaggaacaa    300
aaaacgttta agacaattca aaacaatttg cgtaagcaga ttgtcaacaa acttactcaa    360
tcggagaagt acaaacgcat tgacaaaaaa gagttaatta cgactgactt accggacttt    420
ctgacaaacg agagcgagaa ggagcttgta gaaaaattta agaatttcac gacgtatttt    480
acagagttcc ataagaatcg taaaaatatg tactccaaag aagaaaaatc gaccgcaatt    540
gcatttcgct tgattaatga gaatttgccc aaattcgtag ataacattgc ggcgttcgag    600
aaagtcgtgt cttccccgct ggccgaaaaa atcaacgctc tttacgagga ctttaaggaa    660
tacctgaacg tagaggaaat cagtcgtgtg tttcgcttag actactatga tgaattgtta    720
actcaaaaac agattgatct ttacaatgct atcgtaggcg ggcgtacgga agaagacaat    780
aaaattcaga ttaaaggtct taaccaatac attaacgagt acaatcagca acagactgac    840
cgctccaatc gtttacctaa attgaagcct ctgtataagc aaattctgag cgatcgcgaa    900
agcgtaagct ggttgcctcc taaatttgac tctgacaaga atttgctgat caaaatcaag    960
gaatgctatg atgcactgtc tgagaaggag aaagttttcg acaagttaga gtctattctt   1020
aagagtttaa gcacttatga tttgagcaag atttacatta gtaatgacag tcaattgagt   1080
```

-continued

```
tacatctccc aaaagatgtt tggccgctgg gatatcattt ccaaggcaat ccgcgaggat   1140
tgtgcgaagc gtaaccctca gaaatctcgt gagtcactgg agaaatttgc agagcgcatt   1200
gataaaaaac ttaaaactat tgatagtatt tccatcgggg atgtagacga atgcttggcc   1260
cagttgggtg aaacttacgt aaaacgtgtc gaggattact ttgttgcgat gggagaatca   1320
gagatcgacg atgaacagac tgacacaacg tccttcaaaa agaacattga aggcgcctac   1380
gagagcgtta aggaacttct taacaatgca gacaatatca ccgacaacaa tcttatgcag   1440
gataaaggta atgtcgaaaa gatcaagaca ctgttggatg ctatcaagga tcttcaacgc   1500
tttattaagc cgttattagg gaaaggtgac gaagcggaca aagatggggt cttctatggt   1560
gaattcacga gcttgtggac caaattagac caagtgacac cgctttataa catggttcgc   1620
aactatttga ccagtaagcc ctatagtaca aaaaagatca agctgaattt cgagaattcc   1680
acccttatgg acgggtggga tttgaacaaa gagcctgata ataccactgt gatttttgt    1740
aaggacggtt tgtactattt gggtatcatg ggaaaaaagt ataatcgcgt ctttgtggat   1800
cgtgaagatt tgccgcacga tggagagtgt tatgataaaa tggaatataa actgcttcca   1860
ggagctaata agatgctgcc aaaagtattc ttctcggaaa ccgggattca acgttttctg   1920
ccttccgagg aacttttagg caagtacgag cgtggaacgc ataagaaggg tgccggcttt   1980
gaccttggag actgtcgcgc tttaatcgat tttttcaaga agtcgatcga acgccacgat   2040
gactggaaaa aattcgattt caagttttcg gacacttcta cctatcagga tatctccgag   2100
ttctaccgtg aggttgaaca acaaggctat aaaatgtcat ttcgcaaggt ctcagtggat   2160
tatatcaaat ctctggtaga ggaaggcaag ttgtatttat ttcaaatcta taataaagat   2220
ttttcggctc attccaaggg cacacccaat atgcacacat tgtactggaa gatgttgttt   2280
gacgaagaga acttaaaaga cgttgtttat aagcttaacg gagaggctga agtcttcttt   2340
cgtaagtcaa gtatcacagt ccaatcaccc acccatcccg caaattcccc aatcaagaat   2400
aagaataaag acaaccaaaa aaaagagagt aagtttgaat atgatttgat caaagatcgt   2460
cgttacaccg tcgataaatt tttgtttcac gttcctatca ccatgaactt caagagtgtg   2520
ggtggttcga atattaatca gttagttaag cgtcacattc gctcggcgac tgacttacac   2580
atcatcggca tcgatcgcgg tgagcgccat ctgctgtacc tgaccgtgat cgattcacgc   2640
ggcaatatta aagaacaatt ttctcttaac gagatcgtca atgaatacaa cggaaacacc   2700
taccgcaccg attaccacga actgcttgac acgcgcgaag gggagcgtac cgaagcacgt   2760
cgtaactggc aaacgattca gaatatccgc gaacttaagg aaggatattt gagccaggtg   2820
atccataaga tttccgaatt ggcaattaaa tacaacgcgg taattgtgct ggaagacctt   2880
aactttggct tcatgcgcag tcgtcagaag gtggaaaaac aggtatacca aaaatttgag   2940
aaaatgttga tcgacaagct taattatttg gtagacaaaa aaaagcctgt ggccgaaacg   3000
gggggattat tgcgcgccta tcaactgacg ggagaatttg agtcattcaa gactcttggc   3060
aagcaatctg gaatcttgtt ctacgtacca gcatggaata ctagcaagat tgaccctgtt   3120
acaggcttcg taaatctttt cgatacacat tacgagaata ttgagaaagc gaaggtgttc   3180
ttcgataagt ttaagtcgat tcgctacaat tcggacaaag attggtttga gttcgtcgtc   3240
gatgactaca ctcgtttttc tcccaaggct gagggaactc gtcgtgattg gacgatttgt   3300
actcagggta aacgtatcca gatttgtcgc aaccatcagc gcaacaatga atgggaaggg   3360
caagaaatcg accttacgaa agccttcaag gaacacttcg aggcgtatgg tgtagacatt   3420
tctaaggatt tacgtgagca aattaacaca cagaataaga aagaattttt tgaagaatta   3480
```

ttgcgtttac ttcgcttgac gctgcagatg cgcaattcaa tgccgtcctc ggatattgat 3540
taccttatct ctccagttgc taatgacact ggatgtttct ttgactctcg caaacaggcg 3600
gaattgaagg aaaatgccgt tttgccgatg aacgcggatg ctaatggagc gtacaacatc 3660
gctcgtaaag gacttttggc gattcgcaaa atgaaacagg aggagaacga ctccgcgaaa 3720
attagcttag ccattagtaa taaggagtgg ttgaagttcg cacagactaa accgtatctg 3780
gaagattga 3789

<210> SEQ ID NO 17
<211> LENGTH: 3903
<212> TYPE: DNA
<213> ORGANISM: Artificial Sequence
<220> FEATURE:
<223> OTHER INFORMATION: FnCpf1

<400> SEQUENCE: 17
atgtctatct accaggagtt tgtaaacaag tattctctta gtaaaacgtt gcgttttgaa 60
cttattccac agggtaaaac cctggagaat attaaggctc gtggcttaat tcttgatgac 120
gaaaagcgcg caaaggatta caaaaaggca aaacaaatta ttgataagta ccatcagttc 180
ttcattgaag agattttatc cagcgtttgt atctccgagg acctgttaca gaactacagc 240
gatgtatatt tcaaattgaa aaaatccgat gatgacaatc tgcaaaagga ttttaaatcg 300
gccaaggaca ctatcaagaa acaaatttct gagtacatca aagatagcga gaaattcaag 360
aatttattta accaaaatct gatcgacgcg aagaaggggc aggagtcaga cttgattttg 420
tggttgaaac agtcgaaaga taatggaatc gaactgttca aagccaactc tgacattaca 480
gatattgatg aagctctgga aattattaag agctttaagg ggtggaccac ctatttcaaa 540
gggttccacg agaaccgtaa aaacgtgtac tcttcgaatg atattcctac tagcattatt 600
tatcgtattg tagacgacaa ccttcctaaa ttcttggaga ataaagctaa atatgaatcg 660
ctgaaggata aggcgcccga agcaatcaat tacgaacaaa tcaaaaaaga tctggctgaa 720
gaactgacct ttgacattga ctataaaact tctgaagtaa accagcgcgt tttcagtctt 780
gacgaggttt ttgaaatcgc taattttaat aattatttaa atcaatccgg gattacaaaa 840
tttaacacga ttattggtgg caagttcgta aatggagaga acactaagcg taagggaatt 900
aacgagtaca ttaatttata ctcgcagcag attaacgaca aaacgctgaa aaaatataaa 960
atgagcgttt tatttaagca aattctgagc gataccgagt caaagtcctt cgtaattgac 1020
aagcttgagg atgactctga cgttgtcacg acgatgcagt cattctatga acagattgcg 1080
gcttttaaaa ccgtggaaga aaaatcaatc aaagagacct tgtcattatt atttgacgat 1140
ctgaaagctc aaaagttgga cttaagtaag atctacttta agaatgataa gagtctgacg 1200
gatttatccc aacaagtctt tgacgactac tctgtaattg gcacagccgt cttggaatac 1260
atcacccaac aaatcgctcc taaaaattta gacaatccga gtaaaaagga acaagagctg 1320
attgcaaaaa agaccgagaa agcgaaatat ttatcgttag aaactattaa attagcgctg 1380
gaagaattta ataaacaccg tgacattgac aagcaatgtc gtttcgaaga gattttagct 1440
aactttgcgg ccatcccgat gatctttgac gagattgcac aaaataaaga caatcttgcg 1500
cagatctcga ttaagtatca gaaccaaggt aagaaagacc tgttgcaggc ttccgcagag 1560
gatgacgtta aagcgatcaa agatctgtta gaccaaacca acaatttgct tcacaagtta 1620
aagatttttc acatttcaca gtcagaggat aaagcaaaca ttcttgataa agacgaacac 1680

```
ttttatttag ttttcgagga atgttatttt gagctggcga acattgttcc cctttataat   1740
aagatccgta attatatcac tcagaaacct tattctgacg agaaattcaa gttgaatttt   1800
gaaaactcca ctcttgcgaa cggctgggat aaaaataagg aacccgataa tactgccatt   1860
ctgtttatta aagacgacaa atattactta ggagttatga ataagaaaaa caataagatc   1920
tttgatgaca aagctattaa ggagaacaaa ggcgagggct acaaaaaaat tgtatacaaa   1980
cttctgcctg gagctaacaa gatgttgcca aaagtatttt tcagtgcaaa atcgattaag   2040
ttctacaacc catcggagga tattttacgt attcgcaacc attccaccca tacgaaaaat   2100
gggtcacccc aaaagggtta cgaaaagttt gagtttaata ttgaagattg ccgtaagttt   2160
attgattttt ataaacaatc tatctctaaa caccccgaat ggaaggattt cggattccgt   2220
ttctctgaca cacaacgcta caattcgatc gatgaattct atcgtgaggt tgagaaccaa   2280
ggatataagt tgacatttga aaacatttcc gaatcataca tcgattcggt cgtgaaccag   2340
ggtaagttat atttatttca gatctacaac aaggattttt ccgcctatag caaaggccgt   2400
ccgaacttac atacgttgta ctggaaggcc ctgtttgatg agcgcaatct gcaagatgtc   2460
gtatataagt taaatggcga agctgaactg ttttaccgca agcagtcgat cccgaagaag   2520
atcacacatc ctgctaagga ggcaattgct aacaagaata aagacaatcc aaagaaagaa   2580
agtgtcttcg agtatgactt aattaaagat aaacgtttta ctgaggacaa gtttttcttt   2640
cattgcccaa tcacaatcaa tttcaaatca agtggagcaa acaagtttaa cgacgaaatt   2700
aacttactgc tgaaggaaaa ggcgaatgac gtgcacattc tgtccattga tcgcggagaa   2760
cgtcacctgg cgtactatac gttggtcgac gggaagggaa acatcattaa acaggacacg   2820
tttaatatta tcggcaatga tcgcatgaag acaaattatc acgacaagct ggcggcaatt   2880
gagaaggatc gtgactcagc tcgcaaagac tggaagaaga ttaacaacat caaggagatg   2940
aaagagggtt atcttagcca agtcgtccat gagattgcaa aattggttat tgaatacaat   3000
gcgattgttg tcttcgaaga tcttaatttt gggttcaaac gtggtcgctt caaagtcgag   3060
aagcaggttt accaaaagct ggaaaagatg cttattgaga aattgaatta cttggttttc   3120
aaggacaatg aattcgataa gacaggcggt gtacttcgtg cgtatcaact tacggcaccc   3180
tttgaaacct tcaaaaaaat gggcaaacaa actgggatca tctactacgt gccggcgggg   3240
ttcaccagca aaatttgtcc tgtaactggg ttcgtgaacc agttgtaccc caaatacgaa   3300
tcagtcagta agtcccagga gtttttttct aagttcgata agatctgtta taatcttgac   3360
aaaggctact ttgagttttc tttcgattat aagaactttg gcgataaagc agccaaaggg   3420
aagtggacta ttgcgtcgtt cggctcacgt cttatcaact ttcgcaacag cgataagaac   3480
cataactggg atacacgtga agtttatcca acgaaggagc ttgagaagtt attaaaagat   3540
tacagtattg aatatggca cggggagtgc attaaagcag ctatctgtgg tgagtcggac   3600
aagaaattct tcgcaaaact gacgtctgtt cttaatacca tccttcaaat gcgtaattcc   3660
aagacgggta cggagctgga ttacctgatc agtcccgttg ccgatgttaa tggtaatttt   3720
ttcgactcgc gtcaggcccc gaagaacatg cctcaggacg ccgatgccaa cggtgcgtac   3780
catattggcc ttaagggctt aatgctgtta ggacgtatta agaacaacca ggagggtaaa   3840
aaactgaatc tggtcattaa aaacgaagaa tatttcgaat ttgtacagaa ccgcaataac   3900
tga                                                                 3903
```

<210> SEQ ID NO 18
<211> LENGTH: 3933

<212> TYPE: DNA
<213> ORGANISM: Artificial Sequence
<220> FEATURE:
<223> OTHER INFORMATION: HkCpf1

<400> SEQUENCE: 18
atgttcgaaa agcttagtaa catcgtaagt atttcgaaga cgatccgctt caaattgatt 60
ccagtaggta aaaccctgga gaatattgaa aagcttggca aactggaaaa ggactttgag 120
cgctcggact tttacccaat cctgaagaat atctcggatg actattaccg ccaatacatc 180
aaagaaaaat tgtccgattt aaacctggat tggcagaagc tttacgatgc tcatgagttg 240
ctggactcca gtaagaaaga gtcgcagaaa aaccttgaga tgatccaagc tcagtatcgc 300
aaagtccttt tcaacatttt atcgggcgag cttgataaga gcggagaaaa gaatagcaag 360
gacctgatta agaataataa agccttatac ggaaagttgt tcaaaaaaca atttattctg 420
gaggtcctgc ctgactttgt gaataataac gattcctatt ctgaagaaga tcttgaggga 480
cttaatcttt atagcaaatt tacaactcgc ttgaaaaact tctgggaaac acgtaaaaat 540
gtcttcactg ataaagacat tgtcacggcg attcccttcc gtgcggtgaa tgagaacttt 600
ggattttact acgataacat taaaattttt aacaaaaata ttgagtatct ggagaacaaa 660
atcccaaatt tggaaaatga gttgaaggag gccgatatcc ttgacgacaa tcgctctgtg 720
aaagattact ttacaccaaa cggattcaat tacgtcatca cccaagacgg tattgacgtc 780
taccaagcaa ttcgtggcgg gttcaccaaa gagaatggcg agaaggtcca gggtatcaac 840
gagattttga atcttacaca gcaacagctt cgccgcaagc cggaaactaa aaacgttaag 900
cttggagttt tgacgaagtt gcgtaaacaa atcctggagt atagcgagag cacaagtttt 960
ttgattgatc agattgaaga tgataatgat ttagtagacc gtattaataa gttcaacgta 1020
tcgttctttg aaagcacaga agttagcccc tcattattcg aacagatcga acgcttgtat 1080
aatgccctga agtctattaa aaaagaggaa gtatatattg acgctcgtaa tacacagaaa 1140
ttctcccaga tgcttttcgg tcaatgggac gttatccgcc gcggttacac ggtcaagatt 1200
actgaagggt ctaaggaaga aaagaagaag tacaaagagt atctggagtt agatgaaaca 1260
tctaaggcta agcgttatct taatattcgt gaaattgaag aattagtcaa cttagtagag 1320
gggtttgagg aggtagacgt cttctcagtc ttgctggaga agtttaaaat gaataatatt 1380
gagcgctcag agtttgaggc gccaatttat ggaagcccta ttaaattaga ggcgattaag 1440
gagtacttgg agaaacattt ggaggagtat cacaaatgga agctgttgct tattggaaat 1500
gacgaccttg ataccgacga gaccttctac cctctgctta atgaggtcat ttctgattac 1560
tatatcatcc cactttataa tcttacgcgc aactatttga cccgcaagca cagtgacaag 1620
gacaagatca aagtgaactt tgactttcct accctggctg acgggtggag cgaatcgaag 1680
atctctgaca accgctccat tatcttgcgt aagggggggct attattactt ggggatctta 1740
atcgataata agttattaat taataaaaaa aataagtcaa aaaagattta cgagatcctg 1800
atttacaatc agatccctga attctctaaa tcaattccaa attacccctt tacaaagaaa 1860
gttaaggaac acttcaaaaa caatgttagc gacttccagt taattgatgg ctatgttagc 1920
ccgcttatta ttactaagga aatctatgat attaaaaagg aaaagaagta caaaaaggac 1980
ttctataaag acaacaatac caacaagaac tacttgtata caatttacaa atggatcgaa 2040
ttctgtaagc agtttcttta taagtacaag ggacccaata aggaatccta caaggaaatg 2100
tatgattttt ccacgttaaa ggacacgtcg ttatacgtta acttgaatga cttctacgcc 2160

```
gatgttaact cttgtgctta tcgcgtcctg ttcaataaga tcgacgagaa tactattgac   2220
aacgcggttg aagatgggaa gctgctgtta tttcaaattt acaataaaga ctttagccct   2280
gaatcgaaag gcaaaaagaa tttgcacaca ctgtactggc ttagcatgtt cagcgaagag   2340
aaccttcgca cgcgtaaatt gaagctgaat ggccaggcag agatctttta ccgcaaaaag   2400
ctggagaaga aaccgattat ccataaggaa ggcagtatcc tgcttaacaa gatcgataaa   2460
gaagggaaca caatccccga aaacatttac catgagtgct accgttattt aaataaaaaa   2520
attggtcgcg aggatttgtc agatgaggcg attgcgcttt tcaataaaga cgtcttgaaa   2580
tataaggaag ctcgcttcga tattattaag gaccgccgtt actccgagtc tcaatttttc   2640
tttcatgtgc cgatcacgtt caactgggat atcaagacca acaaaaacgt taaccaaatc   2700
gtgcagggga tgattaaaga tggggaaatt aagcacatta tcgggattga ccgtggcgag   2760
cgtcatttgc tgtactattc cgtcatcgac ttagaaggta atatcgttga acaagggtct   2820
cttaatacct tggagcagaa tcgctttgat aactcgaccg taaaggtaga ttaccaaaac   2880
aaacttcgca cgcgtgaaga agatcgtgac cgtgctcgca aaaattggac gaatattaac   2940
aaaatcaaag aactgaaaga tggttacctg tcccatgtgg tccacaagtt aagtcgcttg   3000
atcattaaat atgaagcaat tgtaatcatg gaaaacttga accaaggttt taagcgcgga   3060
cgttttaagg tagagcgtca agtttaccaa aagttcgagt tggcacttat gaacaagttg   3120
tccgccttgt cgttcaaaga gaagtacgat gaacgcaaaa acttggagcc atcaggaatc   3180
cttaatccta tccaagcatg ttacccagta gatgcctatc aagagttgca aggtcagaac   3240
gggatcgtct tttacttgcc agccgcttat acctccgtta ttgacccggt gactggattt   3300
acaaatttat ttcgcctgaa aagtatcaac agctcgaaat atgaggaatt tattaaaaag   3360
tttaaaaaca tttactttga caatgaagaa gaggacttca aattcatttt taactacaag   3420
gatttcgcaa aggctaatct tgtgatttta aacaatatta agagcaaaga ctggaagatt   3480
agcacgcgcg gtgagcgcat tagctacaat tccaagaaaa aggagtattt ctatgttcaa   3540
cctactgagt tcttaatcaa taaacttaaa gaattaaata tcgattacga aaacattgac   3600
atcatcccat taattgataa tctggaggaa aaggccaaac gtaagattct taaggcgctt   3660
tttgatacct tcaagtactc cgttcaactt cgtaattatg actttgagaa cgattacatc   3720
atctctccga cagcagacga caatggcaat tattacaact caaatgaaat cgacatcgac   3780
aaaacgaatc tgcctaataa cggggacgct aacggtgctt ttaatatcgc tcgcaaaggg   3840
ttgctgctga aggaccgtat cgtcaactct aatgaatcta aggttgacct taaaatcaag   3900
aacgaagact ggatcaattt tatcattagc tga                                3933
```

```
<210> SEQ ID NO 19
<211> LENGTH: 3675
<212> TYPE: DNA
<213> ORGANISM: Artificial Sequence
<220> FEATURE:
<223> OTHER INFORMATION: Lb4Cpf1

<400> SEQUENCE: 19
```

```
atgggtttgt atgatggctt cgttaatcgt tatagtgtca gtaaaaccct gcgtttcgaa     60
cttattccac aagggcgcac tcgtgaatac atcgaaacca atggaatcct gtcagatgac    120
gaggagcgcg ccaaagacta caagacaatc aagcgtctga ttgacgagta ccacaaagac    180
tatatttccc gttgccttaa aaatgtaaac atctcttgtt tggaggagta ctatcacctg    240
tataactcct ctaaccgtga taagcgtcac gaggagctgg atgcattatc cgaccagatg    300
```

```
cgcggcgaga ttgcatcttt tttaactggg aacgacgagt ataaggaaca gaaaagtcgc    360
gacatcatta ttaatgaacg tattattaac tttgcgtcta cggacgaaga gttggcggca    420
gtcaagcgct tccgcaagtt cacaagttat tttactgggt ttttcactaa ccgcgagaac    480
atgtactcgg ccgagaaaaa atctacggcc atcgcacatc gtatcattga cgtgaatctt    540
ccaaagtacg tggataacat taaggcattt aacacggcta tcgaagcggg agtctttgat    600
atcgctgaat ttgaatcaaa tttcaaggcc attaccgatg agcacgaagt aagcgattta    660
cttgacatca ccaaatactc tcgctttatc cgtaatgagg acattatcat ttacaatact    720
cttctggggg gtattagcat gaaagacgaa aaaattcagg ggctgaatga gttaattaat    780
cttcataacc agaagcatcc tggtaagaaa gtgcctttac ttaaggtcct ttacaagcag    840
attttggggg attcacagac tcacagtttt gtcgacgatc agttcgagga cgaccaacag    900
gtcatcaacg ccgtgaaggc ggttacggac accttttcag agacgctgtt aggctctttg    960
aaaattatca ttaataacat tggtcattac gaccttgacc gtatttacat taaagcggga   1020
caggatatca ccacgctgag taaacgtgca ttaaatgatt ggcacattat caccgagtgc   1080
ttggagtcag aatacgatga taaattccct aagaacaaga aaagtgatac ttacgaggaa   1140
atgcgtaacc gctacgttaa gtcctttaag tcgtttagta ttgggcgcct taacagtctg   1200
gtaaccacat atacagaaca agcgtgcttc cttgagaact acttgggctc gtttgggggc   1260
gatactgata agaactgttt gacagatttt accaactcac ttatggaagt agaacatctg   1320
cttaattcag agtatcctgt gacaaatcgt cttatcacgg attacgaatc cgtgcgcatt   1380
cttaagcgcc tgttagattc agaaatggaa gttattcact tcttaaagcc gttgttaggg   1440
aatggaaacg aatcagataa agatcttgtt ttttacgggg aatttgaggc agaatatgag   1500
aaattgctgc ctgtcatcaa agtctataac cgcgtgcgta actatttaac tcgcaagccg   1560
ttttcaacgg agaagatcaa attaaacttt aactccccaa ctcttctgtg cggatggtct   1620
cagagtaaag agaaagaata catgggcgtg attttgcgta aagacggaca gtattacctt   1680
ggtatcatga ctccgagcaa taaaaagatt ttcagcgaag cgcccaagcc tgacgaagat   1740
tgttacgaaa aaatggtctt acgctacatt ccccacccct accagatgct gcctaaggtg   1800
ttcttctcca agtcgaacat tgcctttttt aacccttcgg atgaaatctt gcgcattaaa   1860
aagcaggagt catttaagaa agggaagagt tttaatcgcg atgactgcca caaattcatt   1920
gacttctata aagactcaat caaccgccac gaggagtggc gcaaatttaa cttcaaattt   1980
tctgatacag actcttatga agatatctcg cgtttttaca aagaggtaga gaaccaggct   2040
ttttccatga gctttactaa gatccccacc gtatatattg attcattagt ggacgaggga   2100
aagctttacc tgttcaaact gcacaacaag gattttagcg aacattctaa gggaaagccg   2160
aacttacata cggtttactg gaacgcttta ttctcagaat acaacttaca gaacacggtc   2220
tatcaattga acgggtctgc ggagatcttc ttccgcaaag cctcgattcc agaaaatgag   2280
cgcgtaattc acaagaaaaa tgttcctatt actcgcaaag tagcagaact taatggaaag   2340
aaggaagttt cggtctttcc ttatgatatc atcaaaaacc gccgctacac agtagacaag   2400
tttcaatttc acgtgccact gaaaatgaat ttcaaggccg atgaaaagaa gcgtattaac   2460
gacgacgtaa tcgaagccat ccgtagtaac aaggggattc acgtcatcgg catcgatcgt   2520
ggtgaacgca atcttctgta cttaagctta attaacgagg aagggcgtat catcgaacaa   2580
cgttcgttga atattatcga tagtggagag gggcacactc agaactaccg cgatctgtta   2640
```

```
gactcacgtg aaaaagatcg cgaaaaagct cgtgagaact ggcaggaaat ccaagaaatc   2700
aaagatttga agactggcta tttgtcccag gcgatccata caatcacgaa atggatgaag   2760
gagtacaatg caatcattgt tcttgaagat cttaatgacc gctttacaaa tggccgtaag   2820
aaagttgaaa agcaagtgta tcagaagttc gagaaaatgt taattgataa gcttaattat   2880
tacgtcgata aggacgagga gtttgaccgt atgggtggaa ctcaccgcgc ccttcaattg   2940
acggagaagt tcgagtcatt tcagaaactt ggccgccaga cggggtttat tttctatgtg   3000
cctgcatgga atacctcgaa gttagaccca acaactgggt ttgtagactt gctttatccg   3060
aaatataaat ctgtagatgc gaccaaggat tttatcaaga agtttgactt tatccgcttt   3120
aatagcgaga agaactactt tgagtttggc cttcattatt ccaactttac tgagcgcgct   3180
atcggttgtc gcgatgaatg gattttatgc tcttacggta accgcattgt taatttccgc   3240
aacgccgcaa agaataacag ttgggactac aaagaaatcg acattacgaa acagttactg   3300
gacctgtttg aaaaaaacgg aattgacgta aagcaagaaa atttgatcga cagcatctgt   3360
gaaatgaaag ataaaccttt tttcaagagc cttatcgcga acatcaaact tatcttacag   3420
atccgcaact ccgcgtcggg gactgatatc gactatatga tctctcccgc tatgaatgac   3480
cgcggggagt tctttgacac tcgtaaaggt ttgcagcaat tacctcttga cgccgatgcg   3540
aatggtgcat acaacatcgc gaagaaggga ttatggatcg ttgatcaaat ccgtaatacg   3600
actggcaaca atgtgaagat ggccatgtcc aaccgcgaat ggatgcactt tgcacaggaa   3660
agtcgtctgg cttga                                                   3675
```

```
<210> SEQ ID NO 20
<211> LENGTH: 3621
<212> TYPE: DNA
<213> ORGANISM: Artificial Sequence
<220> FEATURE:
<223> OTHER INFORMATION: Lb5Cpf1

<400> SEQUENCE: 20

atggagaatt attatgattc attgacgcgc caatatccgg ttactaagac cattcgccaa     60
gaacttaaac ccgtggggaa gactttagag aacattaaga atgcggaaat catcgaggcc    120
gacaagcaaa aaaaggaagc atacgtcaaa gtgaaagagc ttatggatga atttcataaa    180
agcatcattg agaaatcatt ggtgggtatc aagctggacg ggttgtcgga atttgaaaag    240
ctgtataaga ttaagacaaa gaccgacgag gacaagaatc gtattagcga gctgttctat    300
tacatgcgca aacagatcgc agacgcgctt aaaaacagcc gtgattacgg gtacgtagat    360
aataaagatc ttatcgaaaa gatcttacca gaacgcgtta aggatgaaaa ctccctgaat    420
gccttgtcct gttttaaggg atttacgact tatttcacgg attattataa aaaccgcaaa    480
aacatctata gtgatgaaga gaaacattcc acggtggggt atcgctgcat caacgagaac    540
ttattgattt tcatgtctaa tattgaggta tatcaaatct ataagaaggc gaacatcaag    600
aatgacaatt acgatgaaga gaccctggat aagaccttca tgatcgagtc gttcaacgag    660
tgcttaacgc agtctggagt tgaggcctat aattcggtag tcgcctctat caagacggcg    720
acaaatctgt atattcaaaa aaataacaag gaggaaaact tcgttcgcgt gcctaagatg    780
aaggtgttgt tcaaacaaat tctgtctgac cgtacgtcat tattcgacgg tctgattatc    840
gagtctgatg acgagttact ggacaaactt tgtagttttt ctgcggaggt agataagttc    900
ttgccgatca atattgatcg ctacatcaag accctgatgg acagcaacaa tggcacgggc    960
atttatgtaa agaacgatag cagtctgacg accttaagca actatttgac agactcgtgg   1020
```

```
tcgtcaattc gtaatgcatt taacgagaac tacgacgcta agtataccgg taaagtcaac   1080
gataagtacg aggaaaagcg tgagaaagca tataaatcca atgactcctt tgaacttaat   1140
tacatccaaa acttattagg aattaatgtg attgacaagt atattgagcg tatcaacttt   1200
gacatcaagg aaatctgtga ggcttataaa gagatgacca aaaattgctt cgaggatcat   1260
gataagacaa aaaaattgca gaagaatatt aaagctgtag cttccattaa gagttatctt   1320
gacagtctga agaacattga gcgtgatatc aagctgttaa acgggacagg attggagtcg   1380
cgcaatgaat ttttttatgg tgaacagagt acggtgttag aagaaatcac gaaagtagat   1440
gagttatata atattacccg caattacctt acgaaaaagc ccttttctac cgaaaaaatg   1500
aagttaaatt tcaacaatcc ccaactttta ggaggttggg acgttaacaa ggagcgtgat   1560
tgttacggtg tgattctgat taaagacaat aactattact tgggtatcat ggataaatcg   1620
gcgaataaga gttttcttaa tattaaggaa agcaaaaacg aaaatgcgta caagaaggtt   1680
aactgcaagc tgcttcctgg acccaacaag atgtttccaa aggtgttctt cgctaagtcg   1740
aacattgact actacgatcc gactcacgaa atcaagaagc tttacgacaa gggaactttt   1800
aaaaagggga attctttcaa tttagaagac tgccataagt tgattgattt ctataaggag   1860
tcgattaaaa agaatgacga ctggaaaaac tttaacttta atttcagtga taccaaggac   1920
tatgaggata tttcgggatt ctttcgtgag gttgaagcgc aaaattataa gattacatat   1980
accaacgtta gctgcgattt cattgagtca cttgttgacg agggtaagct ttatttattt   2040
caaatctaca acaaggattt ttcagagtac gctaccggca atttgaactt acatactctg   2100
tacttaaaaa tgcttttcga cgaacgcaac ttaaaagact tatgcatcaa gatgaacggc   2160
gaggccgagg tgttctaccg ccccgcgtca attttggatg aagacaaagt ggtgcacaaa   2220
gcaaatcaga aaattacgaa caagaacaca aactcgaaaa agaaagaaag tattttcagc   2280
tatgacattg taaaagacaa acgctacact gtcgataaat tttcattca tttgcccatt   2340
acgttgaact ataaggagca aaatgtatcg cgtttcaacg attacattcg tgaaatttta   2400
aaaaagtcta agaacattcg tgtgattggc attgatcgcg gagagcgtaa ccttctgtat   2460
gttgtggtct gtgactctga tgggtcaatt ttgtatcagc gttccattaa tgagatcgta   2520
agcggttccc acaaaacaga ttaccacaag cttttggaca acaaggaaaa agaacgtttg   2580
tccagccgtc gtgattggaa gactatcgaa aatattaaag atctgaaggc gggatatatg   2640
tcgcaagttg ttaatgaaat ttataatttg attttgaagt ataatgctat cgttgtctta   2700
gaagacctta acattggttt taagaatggc cgcaagaagg tggaaaaaca agtgtaccag   2760
aattttgaaa aagccctgat cgacaaactg aactacctgt gtatcgacaa gacgcgcgaa   2820
caattgtcac catcatcacc aggaggagtc ttaaatgcct atcaactgac tgccaagttc   2880
gagagttttg agaagattgg aaaacaaaca ggatgcatct tctacgtgcc agcctacctg   2940
acttcccaga tcgacccaac gacagggttt gtaaacttgt tctatcagaa agatacttcc   3000
aagcaaggcc ttcagctttt cttccgtaag tttaaaaaga tcaacttcga taaggtggcc   3060
agcaattttg aatttgtttt cgattacaat gactttacta ataaagctga gggtactaag   3120
acaaattgga ccatctcaac tcagggtacg cgtatcgcca aataccgctc agatgacgca   3180
aatggaaagt ggatctcgcg tactgtgcat ccgaccgaca ttatcaaaga agctctgaat   3240
cgtgagaaga ttaactataa tgatggccat gacttgattg atgagattgt aagtattgag   3300
aagagcgctg tgctgaagga gatttactac ggatttaagc tgaccctgca attacgtaat   3360
```

```
tcgactttgg ctaatgagga ggagcaggaa gattacatca tctccccagt aaaaaacagt   3420

tcgggaaact acttcgattc ccgcatcaca tcgaaggagt taccttgcga tgctgacgcc   3480

aatggcgctt acaacatcgc acgcaaaggt ttatgggctt tagaacaaat tcgcaacagt   3540

gagaacgtat caaaagtaaa attagcgatc tcgaacaagg agtggtttga gtacacgcaa   3600

aacaatatcc caagtttgtg a                                             3621
```

<210> SEQ ID NO 21
<211> LENGTH: 3687
<212> TYPE: DNA
<213> ORGANISM: Artificial Sequence
<220> FEATURE:
<223> OTHER INFORMATION: LbCpf1

<400> SEQUENCE: 21

```
atgtctaagc tggaaaaatt caccaactgc tacagtttaa gcaagacgtt acgcttcaag     60

gcgatcccgg ttgggaaaac acaagagaat attgacaaca aacgcctttt agttgaagat    120

gagaagcgtg cagaggacta taaaggagtt aagaagcttt tggaccgtta ctacttatcg    180

tttattaatg atgtgctgca ttccatcaaa ctgaagaatc tgaataatta cattagtctt    240

ttccgtaaga aaacacgtac tgagaaggaa aacaaggagc tggaaaatct tgagatcaat    300

ttgcgcaagg agattgctaa ggcattcaaa ggtaacgagg gatataagtc gttgtttaaa    360

aaagacatta ttgaaacgat ccttccggaa ttccttgacg ataaagacga gattgcactg    420

gtgaactcct tcaacgggtt cacgactgcc tttacgggtt tttttgacaa ccgcgagaat    480

atgttcagtg aagaagccaa atctacctct atcgctttcc gctgcattaa tgaaaacctg    540

actcgttata tctctaacat ggacatcttc gaaaaggtag acgcgatctt tgataaacac    600

gaagtgcagg agatcaagga gaaaattctt aatagcgact atgatgttga agatttcttt    660

gagggggaat tctttaactt tgtactgacg caagaaggga tcgacgtcta taacgctatt    720

atcggaggat tcgtaaccga gagtggagag aaaattaagg gtcttaatga gtacattaat    780

ttgtacaatc aaaaaacgaa acagaaattg cccaagttta aacctctgta taaacaagtg    840

ctgagtgatc gcgaaagttt gtcattctat ggagaggggt atactagcga cgaggaggtt    900

cttgaggtgt ttcgcaacac cttaaacaag aactctgaga ttttcagctc aatcaaaaaa    960

cttgagaaat tatttaaaaa tttcgacgaa tactcgtcag ccggcatttt cgtgaaaaat   1020

ggtccggcca tttccacaat ctctaaggac atctttggag aatggaacgt tatccgtgac   1080

aaatggaacg ctgaatatga tgacatccat ttgaaaaaga aggctgtcgt tacagaaaaa   1140

tatgaagatg atcgccgcaa gagcttcaaa aagatcggtt cgttctcgct tgagcagttg   1200

caagaatacg cagatgccga tctgtcagta gtagagaaat taaaggaaat cattattcaa   1260

aaagtggacg agatttacaa agtttacgga tcctctgaga agctttttga tgcagatttt   1320

gtgttggaga aatcgttaaa aaagaatgat gccgtcgtgg caattatgaa agacttatta   1380

gatagcgtga agtccttcga gaattatatt aaggcgttct ttggagaggg taaggagaca   1440

aaccgcgacg aatcgtttta cggcgatttc gtgttggcct acgacatctt gctgaaagtt   1500

gatcacattt acgacgccat ccgtaactat gtaactcaga aaccctacag taaggacaag   1560

tttaagttat actttcagaa tccgcagttc atgggtggat gggataagga caaagagaca   1620

gactaccgtg ctactatctt acgctacggg tcgaagtatt accttgcaat tatggataag   1680

aagtacgcaa aatgcttgca gaagatcgat aaagacgacg tcaacggaaa ttatgaaaag   1740

atcaattata aattattacc cgggcctaat aaaatgttgc ccaaagtatt tttctctaag   1800
```

```
aaatggatgg cctactacaa tccatcagaa gacattcaga agatctataa aaacggcaca   1860
ttcaaaaaag gcgatatgtt caacttgaac gattgccaca aactgattga tttctttaag   1920
gatagcatta gccgttaccc gaagtggtcc aacgcttatg actttaactt cagcgaaaca   1980
gagaagtata aagacattgc agggttctac cgtgaggtag aagaacaagg atataaagtt   2040
tctttcgaaa gtgcaagtaa gaaggaagta gataaattgg ttgaggaggg caaactgtat   2100
atgtttcaga tttacaataa ggatttctct gacaagtccc acggcacacc caatttgcat   2160
actatgtact tcaaacttct gtttgacgag aataaccatg ggcagatccg tcttagtggg   2220
ggagctgagt tatttatgcg ccgtgcgtct ttgaaaaagg aggagttagt tgttcacccg   2280
gcaaattcac ccattgccaa caaaaatcca gataacccca agaagacaac cactctttca   2340
tacgatgtgt acaaagataa gcgtttctct gaagatcaat acgaactgca tattccgatc   2400
gcaatcaaca agtgcccaaa gaacatcttt aaaatcaata cggaagttcg cgttcttctg   2460
aaacatgatg ataacccgta tgttattgga attgatcgtg gggagcgtaa cttgttgtat   2520
attgtcgtag tagatggaaa aggtaacatc gtcgaacagt actcgctgaa tgagattatt   2580
aacaacttca acgggattcg catcaagact gattaccact cacttcttga caaaaaggag   2640
aaggagcgct ttgaagcccg tcaaaattgg acatcaatcg aaaatattaa ggagctgaaa   2700
gccggataca tctctcaagt ggtccataaa atttgtgaac tggtcgagaa atatgatgcc   2760
gtgatcgcgc ttgaggacct gaatagtgga ttcaaaaact cgcgtgtgaa agttgagaaa   2820
caggtgtatc agaaatttga gaaaatgtta attgacaaat tgaactacat ggtagataaa   2880
aagagtaacc catgtgcgac gggcggtgca ttgaagggat accagatcac caataagttt   2940
gagtctttca aaagtatgtc tacgcagaat ggttttattt tctacatccc ggcttggctg   3000
acatctaaaa ttgacccttc gacgggtttt gtcaatctgc tgaaaacaaa gtatacaagt   3060
attgcggatt caaaaaaatt catctcatct ttcgatcgca tcatgtacgt cccagaagaa   3120
gacttatttg agtttgcact ggattataag aatttttccc gtactgacgc agactatatc   3180
aagaaatgga aattatattc atacgggaac cgcattcgta tcttccgtaa tcctaaaaag   3240
aacaacgttt tcgactggga agaagtatgc ttaaccagtg cttacaaaga attgttcaac   3300
aaatacggca ttaactacca gcagggcgac attcgcgcat tattatgcga acagtcagat   3360
aaagcgttct actccagctt tatggcgtta atgtcgctta tgttacagat gcgcaacagc   3420
attacaggcc gcaccgatgt cgattttctg atttcgccgg tgaaaaacag cgatggcatt   3480
ttttacgatt ctcgcaatta cgaggcgcag gaaaatgcaa ttcttccgaa gaacgcagac   3540
gcaaacggcg cttacaacat cgcacgtaaa gttctttggg cgatcggaca atttaaaaaa   3600
gccgaggatg aaaaattgga caaggttaaa attgctatct cgaataaaga gtggcttgag   3660
tacgcgcaaa cttctgttaa gcactga                                       3687
```

```
<210> SEQ ID NO 22
<211> LENGTH: 3669
<212> TYPE: DNA
<213> ORGANISM: Artificial Sequence
<220> FEATURE:
<223> OTHER INFORMATION: OsCpf1

<400> SEQUENCE: 22

atggagaccg aaattttaaa gtacgatttt tttgaacgcg aaggtaagta tatgtattat     60
gatggcctga caaaacagta cgctttaagt aagacaatcc gtaacgagct ggtgccgatt    120
```

-continued

```
ggtaaaactc ttgacaacat caagaaaaac cgtattttag aagcggatat caaacgcaaa    180
tctgattatg agcacgttaa aaagttgatg gatatgtatc ataaaaaaat cattaacgag    240
gcgcttgaca actttaaatt gtctgttctg gaagacgcgg cggacattta cttcaacaaa    300
cagaacgatg aacgtgatat tgatgctttc ttgaaaattc aggacaaact gcgcaaggaa    360
atcgtcgaac agttgaaggg ccatacggac tactccaaag tcggaaataa ggacttcttg    420
ggtctgctta aggccgctag tacagaagag gatcgtatct tgattgagag cttcgacaac    480
ttttacacat atttcacatc gtacaataag gttcgttcaa acctgtactc tgccgaagac    540
aagtcgtcga cagtagcgta tcgtctgatc aatgaaaatt taccaaagtt tttcgataat    600
atcaaagcct atcgcacggt tcgtaacgct ggggtaatct ccggtgacat gtccattgtc    660
gagcaagatg agctgtttga ggtagacacg tttaaccata ctctgacaca atatgggatc    720
gacacgtata accatatgat tggccagttg aacagtgcaa ttaatcttta caatcaaaag    780
atgcatggcg ctggttcttt taagaagtta cccaaaatga aggagttata caagcagctg    840
cttactgagc gtgaggagga attcatcgaa gaatataccg atgacgaagt gctgatcacg    900
agtgttcata attacgtttc atacttgatc gattacctga attccgacaa ggttgagtct    960
tttttgata ctttacgtaa gagcgacggt aaagaggtat ttatcaaaaa cgatgtaagt   1020
aaaactacga tgtctaacat tttatttgac aattggagca ccattgatga tttgattaac   1080
catgaatatg attcagctcc agaaaacgtt aagaaaacga aagatgacaa atatttcgag   1140
aaacgtcaaa aggatttaaa aaagaacaag tcgtactctt tgtcgaagat tgctgctctt   1200
tgtcgcgata caacgattct ggagaagtat atccgtcgtt tggtagacga cattgaaaag   1260
atttacacaa gtaacaatgt cttcagcgac attgttttat ccaaacatga tcgcagtaag   1320
aaattgagca agaatacgaa tgccgtacaa gccattaaga atatgcttga ttctatcaaa   1380
gactttgagc atgatgtcat gcttattaac ggttcaggac aggagatcaa gaaaaatctt   1440
aacgtttact cagaacagga agcattggcc ggcatcttac gccaggtcga ccacatctat   1500
aatcttacac gcaactactt gacaaaaaag cccttctcca cagaaaaaat caaactgaat   1560
tttaatcgcc cgacgttcct ggatgggtgg gacaaaaata aggaggaagc aaacctgggc   1620
atcttgttaa tcaaagataa tcgctactac ctggggatca tgaatacaag tagtaacaag   1680
gcttttgtaa accccccaaa agccattagc aatgatattt ataaaaaggt cgattacaaa   1740
cttttgcctg gccccaacaa gatgttgccc aaggtgtttt ttgcgacgaa gaacattgca   1800
tactatgccc ccagcgagga gttgctgtcg aaatatcgta aagggacgca caagaaagga   1860
gatagtttca gcatcgacga ttgtcgtaac ctgattgatt tttttaaatc gtcaattaac   1920
aaaaacactg attggtcgac gtttggattc aatttctctg atactaacag ttataacgat   1980
atctcggact tttatcgtga agtcgagaaa cagggctaca aattatcgtt cacggatatt   2040
gatgcttgtt acattaaaga cttggtcgat aataatgaat tgtatctgtt tcagatttac   2100
aacaaggact tttcccctta tagtaaaggt aaattaaatc tgcatacact gtacttcaaa   2160
atgttatttg atcaacgcaa ccttgacaac gtagtctata agctgaatgg tgaggcggaa   2220
gtattttacc gccctgcatc catcgagtca gacgagcaaa ttattcacaa gtcaggacaa   2280
aacattaaga ataagaatca gaaacgctca aattgcaaga agacgagcac tttcgactat   2340
gatattgtga aagatcgccg ttattgcaaa gataagttta tgcttcattt gcccatcact   2400
gttaatttcg gtacaaatga gagcggaaaa tttaatgaat tggttaacaa cgcgattcgc   2460
gctgataagg acgttaatgt gattgggatc gaccgtggtg aacgtaattt actttatgta   2520
```

```
gttgtcgttg acccctgcgg taagattatc gaacagatct cgcttaacac aattgtggat   2580
aaagagtatg acatcgagac ggattaccac caattattgg acgaaaaaga ggggtcccgt   2640
gataaggccc gcaaggattg gaatacgatt gagaacatca aagaattgaa ggagggctat   2700
ctgtcgcaag ttgtaaatat cattgccaag ttggtactga aatatgacgc catcatttgt   2760
ttagaagact taaactttgg atttaaacgc ggacgccaaa aagtagaaaa gcaggtgtac   2820
cagaaattcg aaaagatgct gatcgataag atgaattatt tagtgttgga taaatcgcgc   2880
aaacaggaat cccctcaaaa accaggcggc gcgttaaatg ccctgcagtt gactagtgcc   2940
tttaagtcgt ttaaggagtt gggtaaacag acaggtatca tctactatgt accagcgtat   3000
ttgacgagta aaatcgatcc caccaccgga ttcgcaaatc ttttttacat caagtatgaa   3060
tccgtcgata aagcccgtga cttcttcagc aaatttgatt ttatccgtta taaccaaatg   3120
gataactatt tcgaatttgg attcgactac aaatcgttca cagaacgcgc gtcagggtgt   3180
aagtccaaat ggattgcttg cacgaacggc gaacgtatcg tgaaatatcg caattctgat   3240
aaaaataact ctttcgatga taagacagtc atcttgaccg atgaatatcg ctcgctgttc   3300
gacaaatact tacaaaacta tattgatgag gacgatctta aggaccaaat cttgcagatt   3360
gattctgcag acttttacaa gaatcttatt aaactgttcc agttgaccct tcaaatgcgc   3420
aatagcagct ccgacggaaa gcgtgattat attatttccc ccgtgaagaa ttatcgcgag   3480
gagttctttt gcagtgagtt cagtgatgac accttccctc gtgacgccga cgcaaatgga   3540
gcatataaca tcgctcgcaa agggctgtgg gtcatcaagc agatccgtga gacaaaaagc   3600
ggcacgaaaa tcaacttggc gatgagcaat agcgagtggt tggaatacgc ccaatgcaat   3660
ttgctttga                                                           3669
```

<210> SEQ ID NO 23
<211> LENGTH: 3897
<212> TYPE: DNA
<213> ORGANISM: Artificial Sequence
<220> FEATURE:
<223> OTHER INFORMATION: TsCpf1

<400> SEQUENCE: 23

```
atgaccaaga ctttcgatag cgagttcttc aacctgtaca gcttgcaaaa aacggtccgt     60
tttgagttaa agccagtcgg tgaaactgca tcctttgtcg aggatttcaa aaatgaagga    120
ttaaagcgcg tagtgagcga ggacgaacgt cgcgcggtcg attaccagaa ggtgaaggaa    180
atcatcgatg attaccatcg cgatttcatc gaagaatccc ttaactattt tcctgagcaa    240
gtgagtaagg acgcccttga gcaggcgttt catttatatc agaagttgaa agccgctaag    300
gtagaagagc gcgagaaagc gttgaaggaa tgggaagccc tgcaaaaaaa attgcgtgaa    360
aaagtagtga agtgtttctc cgacagcaat aaagcgcgtt tctctcgtat cgataagaaa    420
gagctgatca aggaagatct tatcaactgg ttagtcgccc aaaatcgtga agacgacatt    480
cctactgtcg agacgttcaa taattttacg acgtacttca caggttttca tgaaaatcgt    540
aagaacattt attcaaaaga cgaccatgct accgctatca gtttccgctt gatccatgag    600
aacctgccaa agtttttcga caacgtcatt tcttttaaca agttaaaaga aggttttccc    660
gagcttaagt tcgataaggt gaaagaagat ttggaagtag attatgactt gaaacacgct    720
tttgaaattg agtactttgt taattttgtt acccaggccg gtatcgacca atacaattac    780
ttgttaggcg gaaagacgtt agaagatgga acaaagaaac aaggaatgaa tgagcaaatt    840
```

-continued

```
aacttattca agcagcaaca gacgcgcgac aaggcacgtc agattcccaa attgattcca    900
ctttttaaac aaatcctgtc tgagcgtaca gagtcccaga gtttcattcc aaaacagttt    960
gaatccgacc aagagctgtt tgattcgttg caaaaattac ataacaactg tcaggataag   1020
ttcacggttt tgcaacaagc catcttaggc ttagcagaag cggatcttaa aaaggtattc   1080
atcaaaacgt cagatttgaa cgcgctgagt aacaccattt tcggtaacta ttcggtattc   1140
tctgatgcgc tgaacctgta caaagaaagt cttaaaacta aaaaagccca agaggccttt   1200
gaaaaacttc ccgcacatag catccacgat ttaatccaat accttgaaca gtttaacagc   1260
tctctggacg cagagaaaca acaatcgacc gatacggtat tgaactattt cattaagact   1320
gacgaattgt atagccgctt tatcaagagc acatctgagg cctttacgca agtgcagcct   1380
ctttttgaat tggaggctct gtcgtcaaag cgccgcccac cagaatcaga agacgaagga   1440
gcgaagggtc aggaaggatt cgagcagatt aagcgtatta aagcttacct tgacaccctg   1500
atggaggccg tacacttcgc taagccgctt tacttggtca aaggccgtaa gatgatcgaa   1560
ggcttggaca aagaccaatc tttttacgaa gcattcgaga tggcatatca ggaattagaa   1620
agtcttatta ttcctattta caataaggct cgttcatatc ttagccgcaa accgtttaag   1680
gcggataaat tcaaaattaa ctttgacaac aacactctgt tatctggctg ggacgctaat   1740
aaagaaactg ctaatgcgtc gatcctgttt aaaaaagatg gactttatta cttagggatt   1800
atgcctaaag ggaaaacgtt tcttttttgat tatttcgttt cgagtgaaga ctcggaaaaa   1860
ctgaaacagc gccgccagaa aacggcagag gaagctttgg cacaagacgg ggagtcatat   1920
ttcgaaaaga ttcgctataa actgctgccc ggcgcaagca aaatgttgcc gaaggtattt   1980
ttttccaaca aaaatattgg gttctataac ccgtcagacg atatcttgcg tattcgcaat   2040
acagcgtcac acactaagaa tggcactccg cagaaagggc atagcaaggt ggaatttaac   2100
ttgaatgact gtcacaagat gatcgacttt tttaagtctt cgattcaaaa gcacccagag   2160
tgggggtcct ttggatttac tttctccgat actagcgact tcgaagatat gagtgcgttt   2220
tatcgtgaag tggagaacca gggatacgtt atttcattcg acaagatcaa ggaaacctac   2280
attcagagcc aagtcgaaca ggggaacctt tatctgtttc aaatctacaa caaggatttt   2340
agtccctact ctaagggcaa acccaactta cacaccttat actggaaggc tctttttgag   2400
gaagcaaacc ttaataatgt agttgcgaaa ttaaatggcg aggctgaaat ttttttccgc   2460
cgtcatagta tcaaagcctc tgacaaggtc gtacacccgg ccaaccaagc aatcgacaac   2520
aaaaatcccc atacagagaa aacgcaaagt acgtttgaat atgatcttgt gaaggacaag   2580
cgctatactc aagataagtt cttcttccac gtcccaatca gtctgaattt taaagcgcag   2640
ggtgtttcga aatttaacga taaagttaac gggttcctta aagggaaccc ggatgtaaat   2700
atcattggga tcgaccgtgg ggaacgtcat ttgttgtact ttacggtagt aaatcagaaa   2760
ggtgagattt tggtgcaaga gtcacttaat acactgatga gcgataaggg tcacgtgaac   2820
gattatcagc agaagttaga taagaaggag caggaacgtg acgccgcccg caaatcttgg   2880
acaactgtcg agaacattaa ggaactgaaa gaaggttatc tgtctcatgt ggttcacaag   2940
ttagcgcatc tgatcattaa atacaatgcg atcgtgtgtc tggaagactt aaatttcggt   3000
tttaagcgtg gacgctttaa agtcgaaaaa caggtctatc aaaagttcga aaaggcgctg   3060
atcgataagc tgaactattt agttttcaag gagaaggagt taggtgaggt cgggcactac   3120
ttaacagctt accaactgac agctccattc gagtccttta aaaagttagg caagcagagc   3180
ggaatccttt tttatgttcc cgctgactat acatcgaaga tcgacccgac cacgggcttt   3240
```

```
gttaacttcc ttgatctgcg ctatcaaagc gttgaaaagg caaagcaact tctttcagat   3300

tttaatgcca ttcgtttcaa ttctgtccaa aactactttg agttcgaaat cgactacaaa   3360

aaattgacac caaagcgtaa agttgggacc cagtcaaagt gggtgatctg cacgtatgga   3420

gatgtccgtt atcagaatcg tcgcaatcaa aaggggcact gggaaactga ggaggtaaat   3480

gtgactgaga aattaaaggc tttgttcgcg agcgactcta aaaccactac agtcattgat   3540

tacgcgaatg atgacaactt aatcgacgtt atcttagagc aggacaaagc atcgtttttt   3600

aaggaattat tgtggctgct gaagctgacg atgacgttac gtcatagcaa gatcaagtct   3660

gaagatgact ttatcttgag ccctgtcaag aacgagcagg gcgaatttta cgacagtcgc   3720

aaagcaggtg aagtctggcc gaaggatgcc gacgctaacg gtgcgtatca cattgcgctt   3780

aagggactgt ggaacctgca acagattaat cagtgggaaa aaggtaagac attgaatctg   3840

gcaattaaaa accaggattg gttttccttt atccaagaga agccatacca agagtga      3897
```

<210> SEQ ID NO 24
<211> LENGTH: 33
<212> TYPE: DNA
<213> ORGANISM: Artificial Sequence
<220> FEATURE:
<223> OTHER INFORMATION: SARS-Orf1ab-RPA-F

<400> SEQUENCE: 24

```
ctaacatgct taggataatg gcctctcttg ttc                                 33
```

<210> SEQ ID NO 25
<211> LENGTH: 33
<212> TYPE: DNA
<213> ORGANISM: Artificial Sequence
<220> FEATURE:
<223> OTHER INFORMATION: SARS-Orf1ab -RPA-R

<400> SEQUENCE: 25

```
gtaagcgtaa aactcatcca cgaattcatg atc                                 33
```

<210> SEQ ID NO 26
<211> LENGTH: 35
<212> TYPE: DNA
<213> ORGANISM: Artificial Sequence
<220> FEATURE:
<223> OTHER INFORMATION: MERS-upE-RPA-F

<400> SEQUENCE: 26

```
ctcgcttatc gtttaagcag ctctgcgcta ctatg                               35
```

<210> SEQ ID NO 27
<211> LENGTH: 35
<212> TYPE: DNA
<213> ORGANISM: Artificial Sequence
<220> FEATURE:
<223> OTHER INFORMATION: MERS-upE-RPA-F

<400> SEQUENCE: 27

```
ctcgcttatc gtttaagcag ctctgcgcta ctatg                               35
```

<210> SEQ ID NO 28
<211> LENGTH: 30
<212> TYPE: DNA
<213> ORGANISM: Artificial Sequence
<220> FEATURE:
<223> OTHER INFORMATION: MERS-Orf1-RPA-F

<400> SEQUENCE: 28
ctattcccac acagttgttc ccactcttat 30

<210> SEQ ID NO 29
<211> LENGTH: 30
<212> TYPE: DNA
<213> ORGANISM: Artificial Sequence
<220> FEATURE:
<223> OTHER INFORMATION: MERS-Orf1-RPA-R

<400> SEQUENCE: 29
cttgaggctt ctccaatgct ataagtgtac 30

<210> SEQ ID NO 30
<211> LENGTH: 3903
<212> TYPE: DNA
<213> ORGANISM: Artificial Sequence
<220> FEATURE:
<223> OTHER INFORMATION: FnCpf1-K180R

<400> SEQUENCE: 30
atgtctatct accaggagtt tgtaaacaag tattctctta gtaaaacgtt gcgttttgaa 60
cttattccac agggtaaaac cctggagaat attaaggctc gtggcttaat tcttgatgac 120
gaaaagcgcg caaaggatta caaaaaggca aaacaaatta ttgataagta ccatcagttc 180
ttcattgaag agattttatc cagcgtttgt atctccgagg acctgttaca gaactacagc 240
gatgtatatt tcaaattgaa aaaatccgat gatgacaatc tgcaaaagga ttttaaatcg 300
gccaaggaca ctatcaagaa acaaatttct gagtacatca aagatagcga gaaattcaag 360
aatttattta accaaaatct gatcgacgcg aagaaggggc aggagtcaga cttgattttg 420
tggttgaaac agtcgaaaga taatggaatc gaactgttca aagccaactc tgacattaca 480
gatattgatg aagctctgga aattattaag agctttaagg ggtggaccac ctatttccgt 540
gggttccacg agaaccgtaa aaacgtgtac tcttcgaatg atattcctac tagcattatt 600
tatcgtattg tagacgacaa ccttcctaaa ttcttggaga ataaagctaa atatgaatcg 660
ctgaaggata aggcgcccga agcaatcaat tacgaacaaa tcaaaaaaga tctggctgaa 720
gaactgacct ttgacattga ctataaaact tctgaagtaa accagcgcgt tttcagtctt 780
gacgaggttt ttgaaatcgc taattttaat aattatttaa atcaatccgg gattacaaaa 840
tttaacacga ttattggtgg caagttcgta aatggagaga acactaagcg taagggaatt 900
aacgagtaca ttaatttata ctcgcagcag attaacgaca aaacgctgaa aaaatataaa 960
atgagcgttt tatttaagca aattctgagc gataccgagt caaagtcctt cgtaattgac 1020
aagcttgagg atgactctga cgttgtcacg acgatgcagt cattctatga acagattgcg 1080
gcttttaaaa ccgtggaaga aaaatcaatc aaagagacct tgtcattatt atttgacgat 1140
ctgaaagctc aaaagttgga cttaagtaag atctacttta agaatgataa gagtctgacg 1200
gatttatccc aacaagtctt tgacgactac tctgtaattg gcacagccgt cttggaatac 1260
atcacccaac aaatcgctcc taaaaattta gacaatccga gtaaaaagga acaagagctg 1320
attgcaaaaa agaccgagaa agcgaaatat ttatcgttag aaactattaa attagcgctg 1380
gaagaattta ataaacaccg tgacattgac aagcaatgtc gtttcgaaga gattttagct 1440
aactttgcgg ccatcccgat gatctttgac gagattgcac aaaataaaga caatcttgcg 1500
cagatctcga ttaagtatca gaaccaaggt aagaaagacc tgttgcaggc ttccgcagag 1560
gatgacgtta aagcgatcaa agatctgtta gaccaaacca acaatttgct tcacaagtta 1620

```
aagatttttc acatttcaca gtcagaggat aaagcaaaca ttcttgataa agacgaacac   1680
ttttatttag ttttcgagga atgttatttt gagctggcga acattgttcc cctttataat   1740
aagatccgta attatatcac tcagaaacct tattctgacg agaaattcaa gttgaatttt   1800
gaaaactcca ctcttgcgaa cggctgggat aaaaataagg aacccgataa tactgccatt   1860
ctgtttatta aagacgacaa atattactta ggagttatga ataagaaaaa caataagatc   1920
tttgatgaca aagctattaa ggagaacaaa ggcgagggct acaaaaaaat tgtatacaaa   1980
cttctgcctg gagctaacaa gatgttgcca aaagtatttt tcagtgcaaa atcgattaag   2040
ttctacaacc catcggagga tattttacgt attcgcaacc attccaccca tacgaaaaat   2100
gggtcacccc aaaagggtta cgaaaagttt gagtttaata ttgaagattg ccgtaagttt   2160
attgattttt ataaacaatc tatctctaaa caccccgaat ggaaggattt cggattccgt   2220
ttctctgaca cacaacgcta caattcgatc gatgaattct atcgtgaggt tgagaaccaa   2280
ggatataagt tgacatttga aaacatttcc gaatcataca tcgattcggt cgtgaaccag   2340
ggtaagttat atttatttca gatctacaac aaggattttt ccgcctatag caaaggccgt   2400
ccgaacttac atacgttgta ctggaaggcc ctgtttgatg agcgcaatct gcaagatgtc   2460
gtatataagt taaatggcga agctgaactg ttttaccgca agcagtcgat cccgaagaag   2520
atcacacatc ctgctaagga ggcaattgct aacaagaata aagacaatcc aaagaaagaa   2580
agtgtcttcg agtatgactt aattaaagat aaacgtttta ctgaggacaa gtttttcttt   2640
cattgcccaa tcacaatcaa tttcaaatca agtggagcaa acaagtttaa cgacgaaatt   2700
aacttactgc tgaaggaaaa ggcgaatgac gtgcacattc tgtccattga tcgcggagaa   2760
cgtcacctgg cgtactatac gttggtcgac gggaagggaa acatcattaa acaggacacg   2820
tttaatatta tcggcaatga tcgcatgaag acaaattatc acgacaagct ggcggcaatt   2880
gagaaggatc gtgactcagc tcgcaaagac tggaagaaga ttaacaacat caaggagatg   2940
aaagagggtt atcttagcca agtcgtccat gagattgcaa aattggttat tgaatacaat   3000
gcgattgttg tcttcgaaga tcttaatttt gggttcaaac gtggtcgctt caaagtcgag   3060
aagcaggttt accaaaagct ggaaaagatg cttattgaga aattgaatta cttggttttc   3120
aaggacaatg aattcgataa gacaggcggt gtacttcgtg cgtatcaact tacggcaccc   3180
tttgaaacct tcaaaaaaat gggcaaacaa actgggatca tctactacgt gccggcgggg   3240
ttcaccagca aaatttgtcc tgtaactggg ttcgtgaacc agttgtaccc caaatacgaa   3300
tcagtcagta agtcccagga gttttttct aagttcgata agatctgtta taatcttgac    3360
aaaggctact ttgagttttc tttcgattat aagaactttg gcgataaagc agccaaaggg   3420
aagtggacta ttgcgtcgtt cggctcacgt cttatcaact ttcgcaacag cgataagaac   3480
cataactggg atacacgtga agtttatcca acgaaggagc ttgagaagtt attaaaagat   3540
tacagtattg aatatgggca cggggagtgc attaaagcag ctatctgtgg tgagtcggac   3600
aagaaattct tcgcaaaact gacgtctgtt cttaatacca tccttcaaat gcgtaattcc   3660
aagacgggta cggagctgga ttacctgatc agtcccgttg ccgatgttaa tggtaatttt   3720
ttcgactcgc gtcaggcccc gaagaacatg cctcaggacg ccgatgccaa cggtgcgtac   3780
catattggcc ttaagggctt aatgctgtta ggacgtatta agaacaacca ggagggtaaa   3840
aaactgaatc tggtcattaa aaacgaagaa tatttcgaat ttgtacagaa ccgcaataac   3900
tga                                                                 3903
```

<210> SEQ ID NO 31
<211> LENGTH: 3903
<212> TYPE: DNA
<213> ORGANISM: Artificial Sequence
<220> FEATURE:
<223> OTHER INFORMATION: FnCpf1-E184R

<400> SEQUENCE: 31

```
atgtctatct accaggagtt tgtaaacaag tattctctta gtaaaacgtt gcgttttgaa     60
cttattccac agggtaaaac cctggagaat attaaggctc gtggcttaat tcttgatgac    120
gaaaagcgcg caaaggatta caaaaaggca aaacaaatta ttgataagta ccatcagttc    180
ttcattgaag agattttatc cagcgtttgt atctccgagg acctgttaca gaactacagc    240
gatgtatatt tcaaattgaa aaaatccgat gatgacaatc tgcaaaagga ttttaaatcg    300
gccaaggaca ctatcaagaa acaaatttct gagtacatca aagatagcga gaaattcaag    360
aatttattta accaaaatct gatcgacgcg aagaaggggc aggagtcaga cttgattttg    420
tggttgaaac agtcgaaaga taatggaatc gaactgttca aagccaactc tgacattaca    480
gatattgatg aagctctgga aattattaag agctttaagg ggtggaccac ctatttcaaa    540
gggttccacc gtaaccgtaa aaacgtgtac tcttcgaatg atattcctac tagcattatt    600
tatcgtattg tagacgacaa ccttcctaaa ttcttggaga ataaagctaa atatgaatcg    660
ctgaaggata aggcgcccga agcaatcaat tacgaacaaa tcaaaaaaga tctggctgaa    720
gaactgacct ttgacattga ctataaaact tctgaagtaa accagcgcgt tttcagtctt    780
gacgaggttt ttgaaatcgc taattttaat aattatttaa atcaatccgg gattacaaaa    840
tttaacacga ttattggtgg caagttcgta aatggagaga acactaagcg taagggaatt    900
aacgagtaca ttaatttata ctcgcagcag attaacgaca aaacgctgaa aaaatataaa    960
atgagcgttt tatttaagca aattctgagc gataccgagt caaagtcctt cgtaattgac   1020
aagcttgagg atgactctga cgttgtcacg acgatgcagt cattctatga acagattgcg   1080
gcttttaaaa ccgtggaaga aaaatcaatc aaagagacct tgtcattatt atttgacgat   1140
ctgaaagctc aaaagttgga cttaagtaag atctacttta agaatgataa gagtctgacg   1200
gatttatccc aacaagtctt tgacgactac tctgtaattg gcacagccgt cttggaatac   1260
atcacccaac aaatcgctcc taaaaattta gacaatccga gtaaaaagga acaagagctg   1320
attgcaaaaa agaccgagaa agcgaaatat ttatcgttag aaactattaa attagcgctg   1380
gaagaattta ataaacaccg tgacattgac aagcaatgtc gtttcgaaga gattttagct   1440
aactttgcgg ccatcccgat gatctttgac gagattgcac aaaataaaga caatcttgcg   1500
cagatctcga ttaagtatca gaaccaaggt aagaaagacc tgttgcaggc ttccgcagag   1560
gatgacgtta aagcgatcaa agatctgtta gaccaaacca acaatttgct tcacaagtta   1620
aagattttcc acatttcaca gtcagaggat aaagcaaaca ttcttgataa agacgaacac   1680
ttttatttag ttttcgagga atgttatttt gagctggcga acattgttcc cctttataat   1740
aagatccgta attatatcac tcagaaacct tattctgacg agaaattcaa gttgaatttt   1800
gaaaactcca ctcttgcgaa cggctgggat aaaaataagg aacccgataa tactgccatt   1860
ctgtttatta aagacgacaa atattactta ggagttatga ataagaaaaa caataagatc   1920
tttgatgaca aagctattaa ggagaacaaa ggcgagggct acaaaaaaat tgtatacaaa   1980
cttctgcctg gagctaacaa gatgttgcca aaagtatttt tcagtgcaaa atcgattaag   2040
ttctacaacc catcggagga tattttacgt attcgcaacc attccaccca tacgaaaaat   2100
```

```
gggtcacccc aaaagggtta cgaaaagttt gagtttaata ttgaagattg ccgtaagttt   2160
attgattttt ataaacaatc tatctctaaa caccccgaat ggaaggattt cggattccgt   2220
ttctctgaca cacaacgcta caattcgatc gatgaattct atcgtgaggt tgagaaccaa   2280
ggatataagt tgacatttga aaacatttcc gaatcataca tcgattcggt cgtgaaccag   2340
ggtaagttat atttatttca gatctacaac aaggattttt ccgcctatag caaaggccgt   2400
ccgaacttac atacgttgta ctggaaggcc ctgtttgatg agcgcaatct gcaagatgtc   2460
gtatataagt taaatggcga agctgaactg ttttaccgca agcagtcgat cccgaagaag   2520
atcacacatc ctgctaagga ggcaattgct aacaagaata aagacaatcc aaagaaagaa   2580
agtgtcttcg agtatgactt aattaaagat aaacgtttta ctgaggacaa gtttttcttt   2640
cattgcccaa tcacaatcaa tttcaaatca agtggagcaa acaagtttaa cgacgaaatt   2700
aacttactgc tgaaggaaaa ggcgaatgac gtgcacattc tgtccattga tcgcggagaa   2760
cgtcacctgg cgtactatac gttggtcgac gggaagggaa acatcattaa acaggacacg   2820
tttaatatta tcggcaatga tcgcatgaag acaaattatc acgacaagct ggcggcaatt   2880
gagaaggatc gtgactcagc tcgcaaagac tggaagaaga ttaacaacat caaggagatg   2940
aaagagggtt atcttagcca agtcgtccat gagattgcaa aattggttat tgaatacaat   3000
gcgattgttg tcttcgaaga tcttaatttt gggttcaaac gtggtcgctt caaagtcgag   3060
aagcaggttt accaaaagct ggaaaagatg cttattgaga aattgaatta cttggttttc   3120
aaggacaatg aattcgataa gacaggcggt gtacttcgtg cgtatcaact tacggcaccc   3180
tttgaaacct tcaaaaaaat gggcaaacaa actgggatca tctactacgt gccggcgggg   3240
ttcaccagca aaatttgtcc tgtaactggg ttcgtgaacc agttgtaccc caaatacgaa   3300
tcagtcagta agtcccagga gtttttttct aagttcgata agatctgtta taatcttgac   3360
aaaggctact tgagttttc tttcgattat aagaactttg gcgataaagc agccaaaggg   3420
aagtggacta ttgcgtcgtt cggctcacgt cttatcaact ttcgcaacag cgataagaac   3480
cataactggg atacacgtga agtttatcca acgaaggagc ttgagaagtt attaaaagat   3540
tacagtattg aatatgggca cggggagtgc attaaagcag ctatctgtgg tgagtcggac   3600
aagaaattct tcgcaaaact gacgtctgtt cttaatacca tccttcaaat gcgtaattcc   3660
aagacgggta cggagctgga ttacctgatc agtcccgttg ccgatgttaa tggtaatttt   3720
ttcgactcgc gtcaggcccc gaagaacatg cctcaggacg ccgatgccaa cggtgcgtac   3780
catattggcc ttaagggctt aatgctgtta ggacgtatta agaacaacca ggagggtaaa   3840
aaactgaatc tggtcattaa aaacgaagaa tatttcgaat ttgtacagaa ccgcaataac   3900
tga                                                                 3903
```

<210> SEQ ID NO 32
<211> LENGTH: 3903
<212> TYPE: DNA
<213> ORGANISM: Artificial Sequence
<220> FEATURE:
<223> OTHER INFORMATION: FnCpf1-N607R

<400> SEQUENCE: 32

```
atgtctatct accaggagtt tgtaaacaag tattctctta gtaaaacgtt gcgttttgaa     60
cttattccac agggtaaaac cctggagaat attaaggctc gtggcttaat tcttgatgac    120
gaaaagcgcg caaaggatta caaaaaggca aaacaaatta ttgataagta ccatcagttc    180
```

```
ttcattgaag agattttatc cagcgtttgt atctccgagg acctgttaca gaactacagc    240
gatgtatatt tcaaattgaa aaaatccgat gatgacaatc tgcaaaagga ttttaaatcg    300
gccaaggaca ctatcaagaa acaaatttct gagtacatca aagatagcga gaaattcaag    360
aatttattta accaaaatct gatcgacgcg aagaaggggc aggagtcaga cttgattttg    420
tggttgaaac agtcgaaaga taatggaatc gaactgttca aagccaactc tgacattaca    480
gatattgatg aagctctgga aattattaag agctttaagg ggtggaccac ctatttcaaa    540
gggttccacg agaaccgtaa aaacgtgtac tcttcgaatg atattcctac tagcattatt    600
tatcgtattg tagacgacaa ccttcctaaa ttcttggaga ataaagctaa atatgaatcg    660
ctgaaggata aggcgcccga agcaatcaat tacgaacaaa tcaaaaaaga tctggctgaa    720
gaactgacct ttgacattga ctataaaact tctgaagtaa accagcgcgt tttcagtctt    780
gacgaggttt ttgaaatcgc taattttaat aattatttaa atcaatccgg gattacaaaa    840
tttaacacga ttattggtgg caagttcgta aatggagaga acactaagcg taagggaatt    900
aacgagtaca ttaatttata ctcgcagcag attaacgaca aaacgctgaa aaaatataaa    960
atgagcgttt tatttaagca aattctgagc gataccgagt caaagtcctt cgtaattgac   1020
aagcttgagg atgactctga cgttgtcacg acgatgcagt cattctatga acagattgcg   1080
gcttttaaaa ccgtggaaga aaaatcaatc aaagagacct tgtcattatt atttgacgat   1140
ctgaaagctc aaaagttgga cttaagtaag atctacttta agaatgataa gagtctgacg   1200
gatttatccc aacaagtctt tgacgactac tctgtaattg gcacagccgt cttggaatac   1260
atcacccaac aaatcgctcc taaaaattta gacaatccga gtaaaaagga acaagagctg   1320
attgcaaaaa agaccgagaa agcgaaatat ttatcgttag aaactattaa attagcgctg   1380
gaagaattta ataaacaccg tgacattgac aagcaatgtc gtttcgaaga gattttagct   1440
aactttgcgg ccatcccgat gatctttgac gagattgcac aaaataaaga caatcttgcg   1500
cagatctcga ttaagtatca gaaccaaggt aagaaagacc tgttgcaggc ttccgcagag   1560
gatgacgtta aagcgatcaa agatctgtta gaccaaacca acaatttgct tcacaagtta   1620
aagatttttc acatttcaca gtcagaggat aaagcaaaca ttcttgataa agacgaacac   1680
ttttatttag ttttcgagga atgttatttt gagctggcga acattgttcc cctttataat   1740
aagatccgta attatatcac tcagaaacct tattctgacg agaaattcaa gttgaatttt   1800
gaaaactcca ctcttgcgcg tggctgggat aaaaataagg aacccgataa tactgccatt   1860
ctgtttatta aagacgacaa atattactta ggagttatga ataagaaaaa caataagatc   1920
tttgatgaca aagctattaa ggagaacaaa ggcgagggct acaaaaaaat tgtatacaaa   1980
cttctgcctg gagctaacaa gatgttgcca aaagtatttt tcagtgcaaa atcgattaag   2040
ttctacaacc catcggagga tattttacgt attcgcaacc attccaccca tacgaaaaat   2100
gggtcacccc aaaagggtta cgaaaagttt gagtttaata ttgaagattg ccgtaagttt   2160
attgattttt ataaacaatc tatctctaaa caccccgaat ggaaggattt cggattccgt   2220
ttctctgaca cacaacgcta caattcgatc gatgaattct atcgtgaggt tgagaaccaa   2280
ggatataagt tgacatttga aaacatttcc gaatcataca tcgattcggt cgtgaaccag   2340
ggtaagttat atttatttca gatctacaac aaggattttt ccgcctatag caaaggccgt   2400
ccgaacttac atacgttgta ctggaaggcc ctgtttgatg agcgcaatct gcaagatgtc   2460
gtatataagt taaatggcga agctgaactg ttttaccgca agcagtcgat cccgaagaag   2520
atcacacatc ctgctaagga ggcaattgct aacaagaata aagacaatcc aaagaaagaa   2580
```

```
agtgtcttcg agtatgactt aattaaagat aaacgtttta ctgaggacaa gtttttcttt   2640
cattgcccaa tcacaatcaa tttcaaatca agtggagcaa acaagtttaa cgacgaaatt   2700
aacttactgc tgaaggaaaa ggcgaatgac gtgcacattc tgtccattga tcgcggagaa   2760
cgtcacctgg cgtactatac gttggtcgac gggaagggaa acatcattaa acaggacacg   2820
tttaatatta tcggcaatga tcgcatgaag acaaattatc acgacaagct ggcggcaatt   2880
gagaaggatc gtgactcagc tcgcaaagac tggaagaaga ttaacaacat caaggagatg   2940
aaagagggtt atcttagcca agtcgtccat gagattgcaa aattggttat tgaatacaat   3000
gcgattgttg tcttcgaaga tcttaatttt gggttcaaac gtggtcgctt caaagtcgag   3060
aagcaggttt accaaaagct ggaaaagatg cttattgaga aattgaatta cttggttttc   3120
aaggacaatg aattcgataa gacaggcggt gtacttcgtg cgtatcaact tacggcaccc   3180
tttgaaacct tcaaaaaaat gggcaaacaa actgggatca tctactacgt gccggcgggg   3240
ttcaccagca aaatttgtcc tgtaactggg ttcgtgaacc agttgtaccc caaatacgaa   3300
tcagtcagta agtcccagga gtttttttct aagttcgata agatctgtta taatcttgac   3360
aaaggctact ttgagttttc tttcgattat aagaactttg gcgataaagc agccaaaggg   3420
aagtggacta ttgcgtcgtt cggctcacgt cttatcaact ttcgcaacag cgataagaac   3480
cataactggg atacacgtga agtttatcca acgaaggagc ttgagaagtt attaaaagat   3540
tacagtattg aatatgggca cggggagtgc attaaagcag ctatctgtgg tgagtcggac   3600
aagaaattct tcgcaaaact gacgtctgtt cttaatacca tccttcaaat gcgtaattcc   3660
aagacgggta cggagctgga ttacctgatc agtcccgttg ccgatgttaa tggtaatttt   3720
ttcgactcgc gtcaggcccc gaagaacatg cctcaggacg ccgatgccaa cggtgcgtac   3780
catattggcc ttaagggctt aatgctgtta ggacgtatta agaacaacca ggagggtaaa   3840
aaactgaatc tggtcattaa aaacgaagaa tatttcgaat ttgtacagaa ccgcaataac   3900
tga                                                                 3903
```

```
<210> SEQ ID NO 33
<211> LENGTH: 3903
<212> TYPE: DNA
<213> ORGANISM: Artificial Sequence
<220> FEATURE:
<223> OTHER INFORMATION: FnCpf1-K613R

<400> SEQUENCE: 33

atgtctatct accaggagtt tgtaaacaag tattctctta gtaaaacgtt gcgttttgaa     60
cttattccac agggtaaaac cctggagaat attaaggctc gtggcttaat tcttgatgac    120
gaaaagcgcg caaaggatta caaaaaggca aaacaaatta ttgataagta ccatcagttc    180
ttcattgaag agattttatc cagcgtttgt atctccgagg acctgttaca gaactacagc    240
gatgtatatt tcaaattgaa aaaatccgat gatgacaatc tgcaaaagga ttttaaatcg    300
gccaaggaca ctatcaagaa acaaatttct gagtacatca aagatagcga gaaattcaag    360
aatttattta accaaaatct gatcgacgcg aagaaggggc aggagtcaga cttgattttg    420
tggttgaaac agtcgaaaga taatggaatc gaactgttca aagccaactc tgacattaca    480
gatattgatg aagctctgga aattattaag agctttaagg ggtggaccac ctatttcaaa    540
gggttccacg agaaccgtaa aaacgtgtac tcttcgaatg atattcctac tagcattatt    600
tatcgtattg tagacgacaa ccttcctaaa ttcttggaga ataaagctaa atatgaatcg    660
```

-continued

```
ctgaaggata aggcgcccga agcaatcaat tacgaacaaa tcaaaaaaga tctggctgaa    720
gaactgacct ttgacattga ctataaaact tctgaagtaa accagcgcgt tttcagtctt    780
gacgaggttt ttgaaatcgc taattttaat aattatttaa atcaatccgg gattacaaaa    840
tttaacacga ttattggtgg caagttcgta aatggagaga acactaagcg taagggaatt    900
aacgagtaca ttaatttata ctcgcagcag attaacgaca aaacgctgaa aaaatataaa    960
atgagcgttt tatttaagca aattctgagc gataccgagt caaagtcctt cgtaattgac   1020
aagcttgagg atgactctga cgttgtcacg acgatgcagt cattctatga acagattgcg   1080
gcttttaaaa ccgtggaaga aaaatcaatc aaagagacct tgtcattatt atttgacgat   1140
ctgaaagctc aaaagttgga cttaagtaag atctacttta agaatgataa gagtctgacg   1200
gatttatccc aacaagtctt tgacgactac tctgtaattg gcacagccgt cttggaatac   1260
atcacccaac aaatcgctcc taaaaattta gacaatccga gtaaaaagga acaagagctg   1320
attgcaaaaa agaccgagaa agcgaaatat ttatcgttag aaactattaa attagcgctg   1380
gaagaattta ataaacaccg tgacattgac aagcaatgtc gtttcgaaga gattttagct   1440
aactttgcgg ccatcccgat gatctttgac gagattgcac aaaataaaga caatcttgcg   1500
cagatctcga ttaagtatca gaaccaaggt aagaaagacc tgttgcaggc ttccgcagag   1560
gatgacgtta aagcgatcaa agatctgtta gaccaaacca acaatttgct tcacaagtta   1620
aagatttttc acatttcaca gtcagaggat aaagcaaaca ttcttgataa agacgaacac   1680
ttttatttag ttttcgagga atgttatttt gagctggcga acattgttcc cctttataat   1740
aagatccgta attatatcac tcagaaacct tattctgacg agaaattcaa gttgaatttt   1800
gaaaactcca ctcttgcgaa cggctgggat aaaaatcgtg aacccgataa tactgccatt   1860
ctgtttatta aagacgacaa atattactta ggagttatga ataagaaaaa caataagatc   1920
tttgatgaca aagctattaa ggagaacaaa ggcgagggct acaaaaaaat tgtatacaaa   1980
cttctgcctg gagctaacaa gatgttgcca aaagtatttt tcagtgcaaa atcgattaag   2040
ttctacaacc catcggagga tattttacgt attcgcaacc attccaccca tacgaaaaat   2100
gggtcacccc aaaagggtta cgaaaagttt gagtttaata ttgaagattg ccgtaagttt   2160
attgattttt ataaacaatc tatctctaaa caccccgaat ggaaggattt cggattccgt   2220
ttctctgaca cacaacgcta caattcgatc gatgaattct atcgtgaggt tgagaaccaa   2280
ggatataagt tgacatttga aaacatttcc gaatcataca tcgattcggt cgtgaaccag   2340
ggtaagttat atttatttca gatctacaac aaggattttt ccgcctatag caaaggccgt   2400
ccgaacttac atacgttgta ctggaaggcc ctgtttgatg agcgcaatct gcaagatgtc   2460
gtatataagt taaatggcga agctgaactg ttttaccgca agcagtcgat cccgaagaag   2520
atcacacatc ctgctaagga ggcaattgct aacaagaata aagacaatcc aaagaaagaa   2580
agtgtcttcg agtatgactt aattaaagat aaacgtttta ctgaggacaa gtttttcttt   2640
cattgcccaa tcacaatcaa tttcaaatca agtggagcaa acaagtttaa cgacgaaatt   2700
aacttactgc tgaaggaaaa ggcgaatgac gtgcacattc tgtccattga tcgcggagaa   2760
cgtcacctgg cgtactatac gttggtcgac gggaagggaa acatcattaa acaggacacg   2820
tttaatatta tcggcaatga tcgcatgaag acaaattatc acgacaagct ggcggcaatt   2880
gagaaggatc gtgactcagc tcgcaaagac tggaagaaga ttaacaacat caaggagatg   2940
aaagagggtt atcttagcca agtcgtccat gagattgcaa aattggttat tgaatacaat   3000
gcgattgttg tcttcgaaga tcttaatttt gggttcaaac gtggtcgctt caaagtcgag   3060
```

```
aagcaggttt accaaaagct ggaaaagatg cttattgaga aattgaatta cttggttttc   3120

aaggacaatg aattcgataa gacaggcggt gtacttcgtg cgtatcaact tacggcaccc   3180

tttgaaacct tcaaaaaaat gggcaaacaa actgggatca tctactacgt gccggcgggg   3240

ttcaccagca aaatttgtcc tgtaactggg ttcgtgaacc agttgtaccc caaatacgaa   3300

tcagtcagta agtcccagga gtttttttct aagttcgata agatctgtta taatcttgac   3360

aaaggctact ttgagttttc tttcgattat aagaactttg gcgataaagc agccaaaggg   3420

aagtggacta ttgcgtcgtt cggctcacgt cttatcaact ttcgcaacag cgataagaac   3480

cataactggg atacacgtga agtttatcca acgaaggagc ttgagaagtt attaaaagat   3540

tacagtattg aatatgggca cggggagtgc attaaagcag ctatctgtgg tgagtcggac   3600

aagaaattct tcgcaaaact gacgtctgtt cttaatacca tccttcaaat gcgtaattcc   3660

aagacgggta cggagctgga ttacctgatc agtcccgttg ccgatgttaa tggtaatttt   3720

ttcgactcgc gtcaggcccc gaagaacatg cctcaggacg ccgatgccaa cggtgcgtac   3780

catattggcc ttaagggctt aatgctgtta ggacgtatta agaacaacca ggagggtaaa   3840

aaactgaatc tggtcattaa aaacgaagaa tatttcgaat ttgtacagaa ccgcaataac   3900

tga                                                                 3903
```

```
<210> SEQ ID NO 34
<211> LENGTH: 3903
<212> TYPE: DNA
<213> ORGANISM: Artificial Sequence
<220> FEATURE:
<223> OTHER INFORMATION: FnCpf1-E184R-N607R

<400> SEQUENCE: 34
```

```
atgtctatct accaggagtt tgtaaacaag tattctctta gtaaaacgtt gcgttttgaa     60

cttattccac agggtaaaac cctggagaat attaaggctc gtggcttaat tcttgatgac    120

gaaaagcgcg caaaggatta caaaaaggca aaacaaatta ttgataagta ccatcagttc    180

ttcattgaag agattttatc cagcgtttgt atctccgagg acctgttaca gaactacagc    240

gatgtatatt tcaaattgaa aaaatccgat gatgacaatc tgcaaaagga ttttaaatcg    300

gccaaggaca ctatcaagaa acaaatttct gagtacatca aagatagcga gaaattcaag    360

aatttattta accaaaatct gatcgacgcg aagaaggggc aggagtcaga cttgattttg    420

tggttgaaac agtcgaaaga taatggaatc gaactgttca aagccaactc tgacattaca    480

gatattgatg aagctctgga aattattaag agctttaagg ggtggaccac ctatttcaaa    540

gggttccacc gtaaccgtaa aaacgtgtac tcttcgaatg atattcctac tagcattatt    600

tatcgtattg tagacgacaa ccttcctaaa ttcttggaga ataaagctaa atatgaatcg    660

ctgaaggata aggcgcccga agcaatcaat tacgaacaaa tcaaaaaaga tctggctgaa    720

gaactgacct ttgacattga ctataaaact tctgaagtaa accagcgcgt tttcagtctt    780

gacgaggttt ttgaaatcgc taattttaat aattatttaa atcaatccgg gattacaaaa    840

tttaacacga ttattggtgg caagttcgta aatggagaga acactaagcg taagggaatt    900

aacgagtaca ttaatttata ctcgcagcag attaacgaca aaacgctgaa aaaatataaa    960

atgagcgttt tatttaagca aattctgagc gataccgagt caaagtcctt cgtaattgac   1020

aagcttgagg atgactctga cgttgtcacg acgatgcagt cattctatga acagattgcg   1080

gcttttaaaa ccgtggaaga aaaatcaatc aaagagacct tgtcattatt atttgacgat   1140
```

-continued

```
ctgaaagctc aaaagttgga cttaagtaag atctacttta agaatgataa gagtctgacg   1200

gatttatccc aacaagtctt tgacgactac tctgtaattg gcacagccgt cttggaatac   1260

atcacccaac aaatcgctcc taaaaattta gacaatccga gtaaaaagga acaagagctg   1320

attgcaaaaa agaccgagaa agcgaaatat ttatcgttag aaactattaa attagcgctg   1380

gaagaattta ataaacaccg tgacattgac aagcaatgtc gtttcgaaga gattttagct   1440

aactttgcgg ccatcccgat gatctttgac gagattgcac aaaataaaga caatcttgcg   1500

cagatctcga ttaagtatca gaaccaaggt aagaaagacc tgttgcaggc ttccgcagag   1560

gatgacgtta aagcgatcaa agatctgtta gaccaaacca acaatttgct tcacaagtta   1620

aagatttttc acatttcaca gtcagaggat aaagcaaaca ttcttgataa agacgaacac   1680

ttttatttag ttttcgagga atgttatttt gagctggcga acattgttcc cctttataat   1740

aagatccgta attatatcac tcagaaacct tattctgacg agaaattcaa gttgaatttt   1800

gaaaactcca ctcttgcgcg tggctgggat aaaaataagg aacccgataa tactgccatt   1860

ctgtttatta aagacgacaa atattactta ggagttatga ataagaaaaa caataagatc   1920

tttgatgaca aagctattaa ggagaacaaa ggcgagggct acaaaaaaat tgtatacaaa   1980

cttctgcctg gagctaacaa gatgttgcca aaagtatttt tcagtgcaaa atcgattaag   2040

ttctacaacc catcggagga tattttacgt attcgcaacc attccaccca tacgaaaaat   2100

gggtcacccc aaaagggtta cgaaaagttt gagtttaata ttgaagattg ccgtaagttt   2160

attgattttt ataaacaatc tatctctaaa caccccgaat ggaaggattt cggattccgt   2220

ttctctgaca cacaacgcta caattcgatc gatgaattct atcgtgaggt tgagaaccaa   2280

ggatataagt tgacatttga aaacatttcc gaatcataca tcgattcggt cgtgaaccag   2340

ggtaagttat atttatttca gatctacaac aaggattttt ccgcctatag caaaggccgt   2400

ccgaacttac atacgttgta ctggaaggcc ctgtttgatg agcgcaatct gcaagatgtc   2460

gtatataagt taaatggcga agctgaactg ttttaccgca agcagtcgat cccgaagaag   2520

atcacacatc ctgctaagga ggcaattgct aacaagaata aagacaatcc aaagaaagaa   2580

agtgtcttcg agtatgactt aattaaagat aaacgtttta ctgaggacaa gtttttcttt   2640

cattgcccaa tcacaatcaa tttcaaatca agtggagcaa acaagtttaa cgacgaaatt   2700

aacttactgc tgaaggaaaa ggcgaatgac gtgcacattc tgtccattga tcgcggagaa   2760

cgtcacctgg cgtactatac gttggtcgac gggaagggaa acatcattaa acaggacacg   2820

tttaatatta tcggcaatga tcgcatgaag acaaattatc acgacaagct ggcggcaatt   2880

gagaaggatc gtgactcagc tcgcaaagac tggaagaaga ttaacaacat caaggagatg   2940

aaagagggtt atcttagcca agtcgtccat gagattgcaa aattggttat tgaatacaat   3000

gcgattgttg tcttcgaaga tcttaatttt gggttcaaac gtggtcgctt caaagtcgag   3060

aagcaggttt accaaaagct ggaaaagatg cttattgaga aattgaatta cttggttttc   3120

aaggacaatg aattcgataa gacaggcggt gtacttcgtg cgtatcaact tacggcaccc   3180

tttgaaacct tcaaaaaaat gggcaaacaa actgggatca tctactacgt gccggcgggg   3240

ttcaccagca aaatttgtcc tgtaactggg ttcgtgaacc agttgtaccc caaatacgaa   3300

tcagtcagta agtcccagga gtttttttct aagttcgata agatctgtta taatcttgac   3360

aaaggctact ttgagttttc tttcgattat aagaactttg gcgataaagc agccaaaggg   3420

aagtggacta ttgcgtcgtt cggctcacgt cttatcaact ttcgcaacag cgataagaac   3480

cataactggg atacacgtga agtttatcca acgaaggagc ttgagaagtt attaaaagat   3540
```

```
tacagtattg aatatgggca cggggagtgc attaaagcag ctatctgtgg tgagtcggac   3600

aagaaattct tcgcaaaact gacgtctgtt cttaatacca tccttcaaat gcgtaattcc   3660

aagacgggta cggagctgga ttacctgatc agtcccgttg ccgatgttaa tggtaatttt   3720

ttcgactcgc gtcaggcccc gaagaacatg cctcaggacg ccgatgccaa cggtgcgtac   3780

catattggcc ttaagggctt aatgctgtta ggacgtatta agaacaacca ggagggtaaa   3840

aaactgaatc tggtcattaa aaacgaagaa tatttcgaat ttgtacagaa ccgcaataac   3900

tga                                                                 3903
```

<210> SEQ ID NO 35
<211> LENGTH: 3903
<212> TYPE: DNA
<213> ORGANISM: Artificial Sequence
<220> FEATURE:
<223> OTHER INFORMATION: FnCpf1-E184R-N607R-K613R

<400> SEQUENCE: 35

```
atgtctatct accaggagtt tgtaaacaag tattctctta gtaaaacgtt gcgttttgaa     60

cttattccac agggtaaaac cctggagaat attaaggctc gtggcttaat tcttgatgac    120

gaaaagcgcg caaaggatta caaaaaggca aaacaaatta ttgataagta ccatcagttc    180

ttcattgaag agattttatc cagcgtttgt atctccgagg acctgttaca gaactacagc    240

gatgtatatt tcaaattgaa aaaatccgat gatgacaatc tgcaaaagga ttttaaatcg    300

gccaaggaca ctatcaagaa acaaatttct gagtacatca aagatagcga gaaattcaag    360

aatttattta accaaaatct gatcgacgcg aagaaggggc aggagtcaga cttgattttg    420

tggttgaaac agtcgaaaga taatggaatc gaactgttca aagccaactc tgacattaca    480

gatattgatg aagctctgga aattattaag agctttaagg ggtggaccac ctatttcaaa    540

gggttccacc gtaaccgtaa aaacgtgtac tcttcgaatg atattcctac tagcattatt    600

tatcgtattg tagacgacaa ccttcctaaa ttcttggaga ataaagctaa atatgaatcg    660

ctgaaggata aggcgcccga agcaatcaat tacgaacaaa tcaaaaaaga tctggctgaa    720

gaactgacct ttgacattga ctataaaact tctgaagtaa accagcgcgt tttcagtctt    780

gacgaggttt ttgaaatcgc taattttaat aattatttaa atcaatccgg gattacaaaa    840

tttaacacga ttattggtgg caagttcgta aatggagaga acactaagcg taagggaatt    900

aacgagtaca ttaatttata ctcgcagcag attaacgaca aaacgctgaa aaaatataaa    960

atgagcgttt tatttaagca aattctgagc gataccgagt caaagtcctt cgtaattgac   1020

aagcttgagg atgactctga cgttgtcacg acgatgcagt cattctatga acagattgcg   1080

gcttttaaaa ccgtggaaga aaaatcaatc aaagagacct tgtcattatt atttgacgat   1140

ctgaaagctc aaaagttgga cttaagtaag atctacttta agaatgataa gagtctgacg   1200

gatttatccc aacaagtctt tgacgactac tctgtaattg gcacagccgt cttggaatac   1260

atcacccaac aaatcgctcc taaaaattta gacaatccga gtaaaaagga acaagagctg   1320

attgcaaaaa agaccgagaa agcgaaatat ttatcgttag aaactattaa attagcgctg   1380

gaagaattta ataaacaccg tgacattgac aagcaatgtc gtttcgaaga gattttagct   1440

aactttgcgg ccatcccgat gatctttgac gagattgcac aaaataaaga caatcttgcg   1500

cagatctcga ttaagtatca gaaccaaggt aagaaagacc tgttgcaggc ttccgcagag   1560

gatgacgtta aagcgatcaa agatctgtta gaccaaacca acaatttgct tcacaagtta   1620
```

```
aagatttttc acatttcaca gtcagaggat aaagcaaaca ttcttgataa agacgaacac   1680
ttttatttag ttttcgagga atgttatttt gagctggcga acattgttcc cctttataat   1740
aagatccgta attatatcac tcagaaacct tattctgacg agaaattcaa gttgaatttt   1800
gaaaactcca ctcttgcgcg tggctgggat aaaaatcgtg aacccgataa tactgccatt   1860
ctgtttatta aagacgacaa atattactta ggagttatga ataagaaaaa caataagatc   1920
tttgatgaca aagctattaa ggagaacaaa ggcgagggct acaaaaaaat tgtatacaaa   1980
cttctgcctg gagctaacaa gatgttgcca aaagtatttt tcagtgcaaa atcgattaag   2040
ttctacaacc catcggagga tattttacgt attcgcaacc attccaccca tacgaaaaat   2100
gggtcacccc aaaagggtta cgaaaagttt gagtttaata ttgaagattg ccgtaagttt   2160
attgattttt ataaacaatc tatctctaaa caccccgaat ggaaggattt cggattccgt   2220
ttctctgaca cacaacgcta caattcgatc gatgaattct atcgtgaggt tgagaaccaa   2280
ggatataagt tgacatttga aaacatttcc gaatcataca tcgattcggt cgtgaaccag   2340
ggtaagttat atttatttca gatctacaac aaggattttt ccgcctatag caaaggccgt   2400
ccgaacttac atacgttgta ctggaaggcc ctgtttgatg agcgcaatct gcaagatgtc   2460
gtatataagt taaatggcga agctgaactg ttttaccgca agcagtcgat cccgaagaag   2520
atcacacatc ctgctaagga ggcaattgct aacaagaata aagacaatcc aaagaaagaa   2580
agtgtcttcg agtatgactt aattaaagat aaacgtttta ctgaggacaa gtttttcttt   2640
cattgcccaa tcacaatcaa tttcaaatca agtggagcaa acaagtttaa cgacgaaatt   2700
aacttactgc tgaaggaaaa ggcgaatgac gtgcacattc tgtccattga tcgcggagaa   2760
cgtcacctgg cgtactatac gttggtcgac gggaagggaa acatcattaa acaggacacg   2820
tttaatatta tcggcaatga tcgcatgaag acaaattatc acgacaagct ggcggcaatt   2880
gagaaggatc gtgactcagc tcgcaaagac tggaagaaga ttaacaacat caaggagatg   2940
aaagagggtt atcttagcca agtcgtccat gagattgcaa aattggttat tgaatacaat   3000
gcgattgttg tcttcgaaga tcttaatttt gggttcaaac gtggtcgctt caaagtcgag   3060
aagcaggttt accaaaagct ggaaaagatg cttattgaga aattgaatta cttggttttc   3120
aaggacaatg aattcgataa gacaggcggt gtacttcgtg cgtatcaact tacggcaccc   3180
tttgaaacct tcaaaaaaat gggcaaacaa actgggatca tctactacgt gccggcgggg   3240
ttcaccagca aaatttgtcc tgtaactggg ttcgtgaacc agttgtaccc caaatacgaa   3300
tcagtcagta agtcccagga gttttttct aagttcgata agatctgtta taatcttgac   3360
aaaggctact ttgagttttc tttcgattat aagaactttg gcgataaagc agccaaaggg   3420
aagtggacta ttgcgtcgtt cggctcacgt cttatcaact ttcgcaacag cgataagaac   3480
cataactggg atacacgtga agtttatcca acgaaggagc ttgagaagtt attaaaagat   3540
tacagtattg aatatgggca cggggagtgc attaaagcag ctatctgtgg tgagtcggac   3600
aagaaattct tcgcaaaact gacgtctgtt cttaatacca tccttcaaat gcgtaattcc   3660
aagacgggta cggagctgga ttacctgatc agtcccgttg ccgatgttaa tggtaatttt   3720
ttcgactcgc gtcaggcccc gaagaacatg cctcaggacg ccgatgccaa cggtgcgtac   3780
catattggcc ttaagggctt aatgctgtta ggacgtatta agaacaacca ggagggtaaa   3840
aaactgaatc tggtcattaa aaacgaagaa tatttcgaat ttgtacagaa ccgcaataac   3900
tga                                                                  3903
```

<210> SEQ ID NO 36
<211> LENGTH: 3687
<212> TYPE: DNA
<213> ORGANISM: Artificial Sequence
<220> FEATURE:
<223> OTHER INFORMATION: LbCpf1-T148R

<400> SEQUENCE: 36

```
atgtctaagc tggaaaaatt caccaactgc tacagtttaa gcaagacgtt acgcttcaag     60
gcgatcccgg ttgggaaaac acaagagaat attgacaaca aacgcctttt agttgaagat    120
gagaagcgtg cagaggacta taaaggagtt aagaagcttt tggaccgtta ctacttatcg    180
tttattaatg atgtgctgca ttccatcaaa ctgaagaatc tgaataatta cattagtctt    240
ttccgtaaga aaacacgtac tgagaaggaa aacaaggagc tggaaaatct tgagatcaat    300
ttgcgcaagg agattgctaa ggcattcaaa ggtaacgagg gatataagtc gttgtttaaa    360
aaagacatta ttgaaacgat ccttccggaa ttccttgacg ataaagacga gattgcactg    420
gtgaactcct tcaacgggtt ccgtactgcc tttacgggtt tttttgacaa ccgcgagaat    480
atgttcagtg aagaagccaa atctacctct atcgctttcc gctgcattaa tgaaaacctg    540
actcgttata tctctaacat ggacatcttc gaaaaggtag acgcgatctt tgataaacac    600
gaagtgcagg agatcaagga gaaaattctt aatagcgact atgatgttga agatttcttt    660
gagggggaat tctttaactt tgtactgacg caagaaggga tcgacgtcta taacgctatt    720
atcggaggat tcgtaaccga gagtggagag aaaattaagg gtcttaatga gtacattaat    780
ttgtacaatc aaaaaacgaa acagaaattg cccaagttta aacctctgta taaacaagtg    840
ctgagtgatc gcgaaagttt gtcattctat ggagaggggt atactagcga cgaggaggtt    900
cttgaggtgt ttcgcaacac cttaaacaag aactctgaga ttttcagctc aatcaaaaaa    960
cttgagaaat tatttaaaaa tttcgacgaa tactcgtcag ccggcatttt cgtgaaaaat   1020
ggtccggcca tttccacaat ctctaaggac atctttggag aatggaacgt tatccgtgac   1080
aaatggaacg ctgaatatga tgacatccat ttgaaaaaga aggctgtcgt tacagaaaaa   1140
tatgaagatg atcgccgcaa gagcttcaaa aagatcggtt cgttctcgct tgagcagttg   1200
caagaatacg cagatgccga tctgtcagta gtagagaaat taaaggaaat cattattcaa   1260
aaagtggacg agatttacaa agtttacgga tcctctgaga agctttttga tgcagatttt   1320
gtgttggaga aatcgttaaa aaagaatgat gccgtcgtgg caattatgaa agacttatta   1380
gatagcgtga agtccttcga gaattatatt aaggcgttct ttggagaggg taaggagaca   1440
aaccgcgacg aatcgtttta cggcgatttc gtgttggcct acgacatctt gctgaaagtt   1500
gatcacattt acgacgccat ccgtaactat gtaactcaga aaccctacag taaggacaag   1560
tttaagttat actttcagaa tccgcagttc atgggtggat gggataagga caaagagaca   1620
gactaccgtg ctactatctt acgctacggg tcgaagtatt accttgcaat tatggataag   1680
aagtacgcaa aatgcttgca gaagatcgat aaagacgacg tcaacggaaa ttatgaaaag   1740
atcaattata aattattacc cgggcctaat aaaatgttgc ccaaagtatt tttctctaag   1800
aaatggatgg cctactacaa tccatcagaa gacattcaga agatctataa aaacggcaca   1860
ttcaaaaaag gcgatatgtt caacttgaac gattgccaca aactgattga tttctttaag   1920
gatagcatta gccgttaccc gaagtggtcc aacgcttatg actttaactt cagcgaaaca   1980
gagaagtata aagacattgc agggttctac cgtgaggtag aagaacaagg atataaagtt   2040
tctttcgaaa gtgcaagtaa gaaggaagta gataaattgg ttgaggaggg caaactgtat   2100
```

```
atgtttcaga tttacaataa ggatttctct gacaagtccc acggcacacc caatttgcat   2160

actatgtact tcaaacttct gtttgacgag aataaccatg ggcagatccg tcttagtggg   2220

ggagctgagt tatttatgcg ccgtgcgtct ttgaaaaagg aggagttagt tgttcacccg   2280

gcaaattcac ccattgccaa caaaaatcca gataacccca agaagacaac cactctttca   2340

tacgatgtgt acaaagataa gcgtttctct gaagatcaat acgaactgca tattccgatc   2400

gcaatcaaca agtgcccaaa gaacatcttt aaaatcaata cggaagttcg cgttcttctg   2460

aaacatgatg ataacccgta tgttattgga attgatcgtg gggagcgtaa cttgttgtat   2520

attgtcgtag tagatggaaa aggtaacatc gtcgaacagt actcgctgaa tgagattatt   2580

aacaacttca acgggattcg catcaagact gattaccact cacttcttga caaaaaggag   2640

aaggagcgct ttgaagcccg tcaaaattgg acatcaatcg aaaatattaa ggagctgaaa   2700

gccggataca tctctcaagt ggtccataaa atttgtgaac tggtcgagaa atatgatgcc   2760

gtgatcgcgc ttgaggacct gaatagtgga ttcaaaaact cgcgtgtgaa agttgagaaa   2820

caggtgtatc agaaatttga gaaaatgtta attgacaaat tgaactacat ggtagataaa   2880

aagagtaacc catgtgcgac gggcggtgca ttgaagggat accagatcac caataagttt   2940

gagtctttca aagtatgtc tacgcagaat ggttttattt tctacatccc ggcttggctg   3000

acatctaaaa ttgacccttc gacgggtttt gtcaatctgc tgaaaacaaa gtatacaagt   3060

attgcggatt caaaaaaatt catctcatct ttcgatcgca tcatgtacgt cccagaagaa   3120

gacttatttg agtttgcact ggattataag aatttttccc gtactgacgc agactatatc   3180

aagaaatgga aattatattc atacgggaac cgcattcgta tcttccgtaa tcctaaaaag   3240

aacaacgttt tcgactggga agaagtatgc ttaaccagtg cttacaaaga attgttcaac   3300

aaatacggca ttaactacca gcagggcgac attcgcgcat tattatgcga acagtcagat   3360

aaagcgttct actccagctt tatggcgtta atgtcgctta tgttacagat gcgcaacagc   3420

attacaggcc gcaccgatgt cgattttctg atttcgccgg tgaaaaacag cgatggcatt   3480

ttttacgatt ctcgcaatta cgaggcgcag gaaaatgcaa ttcttccgaa gaacgcagac   3540

gcaaacggcg cttacaacat cgcacgtaaa gttctttggg cgatcggaca atttaaaaaa   3600

gccgaggatg aaaaattgga caaggttaaa attgctatct cgaataaaga gtggcttgag   3660

tacgcgcaaa cttctgttaa gcactga                                     3687
```

<210> SEQ ID NO 37
<211> LENGTH: 3687
<212> TYPE: DNA
<213> ORGANISM: Artificial Sequence
<220> FEATURE:
<223> OTHER INFORMATION: LbCpf1-T152R

<400> SEQUENCE: 37

```
atgtctaagc tggaaaaatt caccaactgc tacagtttaa gcaagacgtt acgcttcaag     60

gcgatcccgg ttgggaaaac acaagagaat attgacaaca aacgcctttt agttgaagat    120

gagaagcgtg cagaggacta taaaggagtt aagaagcttt tggaccgtta ctacttatcg    180

tttattaatg atgtgctgca ttccatcaaa ctgaagaatc tgaataatta cattagtctt    240

ttccgtaaga aaacacgtac tgagaaggaa aacaaggagc tggaaaatct tgagatcaat    300

ttgcgcaagg agattgctaa ggcattcaaa ggtaacgagg gatataagtc gttgtttaaa    360

aaagacatta ttgaaacgat ccttccggaa ttccttgacg ataaagacga gattgcactg    420

gtgaactcct tcaacgggtt cacgactgcc tttcgtggtt tttttgacaa ccgcgagaat    480
```

```
atgttcagtg aagaagccaa atctacctct atcgctttcc gctgcattaa tgaaaacctg    540

actcgttata tctctaacat ggacatcttc gaaaaggtag acgcgatctt tgataaacac    600

gaagtgcagg agatcaagga gaaaattctt aatagcgact atgatgttga agatttcttt    660

gagggggaat tctttaactt tgtactgacg caagaaggga tcgacgtcta taacgctatt    720

atcggaggat tcgtaaccga gagtggagag aaaattaagg gtcttaatga gtacattaat    780

ttgtacaatc aaaaaacgaa acagaaattg cccaagttta aacctctgta taaacaagtg    840

ctgagtgatc gcgaaagttt gtcattctat ggagaggggt atactagcga cgaggaggtt    900

cttgaggtgt ttcgcaacac cttaaacaag aactctgaga ttttcagctc aatcaaaaaa    960

cttgagaaat tatttaaaaa tttcgacgaa tactcgtcag ccggcatttt cgtgaaaaat   1020

ggtccggcca tttccacaat ctctaaggac atctttggag aatggaacgt tatccgtgac   1080

aaatggaacg ctgaatatga tgacatccat ttgaaaaaga aggctgtcgt tacagaaaaa   1140

tatgaagatg atcgccgcaa gagcttcaaa aagatcggtt cgttctcgct tgagcagttg   1200

caagaatacg cagatgccga tctgtcagta gtagagaaat taaaggaaat cattattcaa   1260

aaagtggacg agatttacaa agtttacgga tcctctgaga agctttttga tgcagatttt   1320

gtgttggaga aatcgttaaa aaagaatgat gccgtcgtgg caattatgaa agacttatta   1380

gatagcgtga agtccttcga gaattatatt aaggcgttct ttggagaggg taaggagaca   1440

aaccgcgacg aatcgtttta cggcgatttc gtgttggcct acgacatctt gctgaaagtt   1500

gatcacattt acgacgccat ccgtaactat gtaactcaga aaccctacag taaggacaag   1560

tttaagttat actttcagaa tccgcagttc atgggtggat gggataagga caaagagaca   1620

gactaccgtg ctactatctt acgctacggg tcgaagtatt accttgcaat tatggataag   1680

aagtacgcaa aatgcttgca gaagatcgat aaagacgacg tcaacggaaa ttatgaaaag   1740

atcaattata aattattacc cgggcctaat aaaatgttgc ccaaagtatt tttctctaag   1800

aaatggatgg cctactacaa tccatcagaa gacattcaga agatctataa aaacggcaca   1860

ttcaaaaaag gcgatatgtt caacttgaac gattgccaca aactgattga tttctttaag   1920

gatagcatta gccgttaccc gaagtggtcc aacgcttatg actttaactt cagcgaaaca   1980

gagaagtata aagacattgc agggttctac cgtgaggtag aagaacaagg atataaagtt   2040

tctttcgaaa gtgcaagtaa gaaggaagta gataaattgg ttgaggaggg caaactgtat   2100

atgtttcaga tttacaataa ggatttctct gacaagtccc acggcacacc caatttgcat   2160

actatgtact tcaaacttct gtttgacgag aataaccatg ggcagatccg tcttagtggg   2220

ggagctgagt tatttatgcg ccgtgcgtct ttgaaaaagg aggagttagt tgttcacccg   2280

gcaaattcac ccattgccaa caaaaatcca gataacccca agaagacaac cactctttca   2340

tacgatgtgt acaaagataa gcgtttctct gaagatcaat acgaactgca tattccgatc   2400

gcaatcaaca agtgcccaaa gaacatcttt aaaatcaata cggaagttcg cgttcttctg   2460

aaacatgatg ataacccgta tgttattgga attgatcgtg gggagcgtaa cttgttgtat   2520

attgtcgtag tagatggaaa aggtaacatc gtcgaacagt actcgctgaa tgagattatt   2580

aacaacttca acgggattcg catcaagact gattaccact cacttcttga caaaaaggag   2640

aaggagcgct ttgaagcccg tcaaaattgg acatcaatcg aaaatattaa ggagctgaaa   2700

gccggataca tctctcaagt ggtccataaa atttgtgaac tggtcgagaa atatgatgcc   2760

gtgatcgcgc ttgaggacct gaatagtgga ttcaaaaact cgcgtgtgaa agttgagaaa   2820
```

```
caggtgtatc agaaatttga gaaaatgtta attgacaaat tgaactacat ggtagataaa   2880

aagagtaacc catgtgcgac gggcggtgca ttgaagggat accagatcac caataagttt   2940

gagtctttca aaagtatgtc tacgcagaat ggttttattt tctacatccc ggcttggctg   3000

acatctaaaa ttgacccttc gacgggtttt gtcaatctgc tgaaaacaaa gtatacaagt   3060

attgcggatt caaaaaaatt catctcatct ttcgatcgca tcatgtacgt cccagaagaa   3120

gacttatttg agtttgcact ggattataag aatttttccc gtactgacgc agactatatc   3180

aagaaatgga aattatattc atacgggaac cgcattcgta tcttccgtaa tcctaaaaag   3240

aacaacgttt tcgactggga agaagtatgc ttaaccagtg cttacaaaga attgttcaac   3300

aaatacggca ttaactacca gcagggcgac attcgcgcat tattatgcga acagtcagat   3360

aaagcgttct actccagctt tatggcgtta atgtcgctta tgttacagat gcgcaacagc   3420

attacaggcc gcaccgatgt cgattttctg atttcgccgg tgaaaaacag cgatggcatt   3480

ttttacgatt ctcgcaatta cgaggcgcag gaaaatgcaa ttcttccgaa gaacgcagac   3540

gcaaacggcg cttacaacat cgcacgtaaa gttctttggg cgatcggaca atttaaaaaa   3600

gccgaggatg aaaaattgga caaggttaaa attgctatct cgaataaaga gtggcttgag   3660

tacgcgcaaa cttctgttaa gcactga                                      3687
```

<210> SEQ ID NO 38
<211> LENGTH: 3687
<212> TYPE: DNA
<213> ORGANISM: Artificial Sequence
<220> FEATURE:
<223> OTHER INFORMATION: LbCpf1-G532R

<400> SEQUENCE: 38

```
atgtctaagc tggaaaaatt caccaactgc tacagtttaa gcaagacgtt acgcttcaag     60

gcgatcccgg ttgggaaaac acaagagaat attgacaaca aacgcctttt agttgaagat    120

gagaagcgtg cagaggacta taaaggagtt aagaagcttt tggaccgtta ctacttatcg    180

tttattaatg atgtgctgca ttccatcaaa ctgaagaatc tgaataatta cattagtctt    240

ttccgtaaga aaacacgtac tgagaaggaa aacaaggagc tggaaaatct tgagatcaat    300

ttgcgcaagg agattgctaa ggcattcaaa ggtaacgagg gatataagtc gttgtttaaa    360

aaagacatta ttgaaacgat ccttccggaa ttccttgacg ataaagacga gattgcactg    420

gtgaactcct tcaacgggtt cacgactgcc tttacgggtt tttttgacaa ccgcgagaat    480

atgttcagtg aagaagccaa atctacctct atcgctttcc gctgcattaa tgaaaacctg    540

actcgttata tctctaacat ggacatcttc gaaaaggtag acgcgatctt tgataaacac    600

gaagtgcagg agatcaagga gaaaattctt aatagcgact atgatgttga agatttcttt    660

gagggggaat tctttaactt tgtactgacg caagaaggga tcgacgtcta taacgctatt    720

atcggaggat tcgtaaccga gagtggagag aaaattaagg gtcttaatga gtacattaat    780

ttgtacaatc aaaaaacgaa acagaaattg cccaagttta aacctctgta taaacaagtg    840

ctgagtgatc gcgaaagttt gtcattctat ggagaggggt atactagcga cgaggaggtt    900

cttgaggtgt ttcgcaacac cttaaacaag aactctgaga ttttcagctc aatcaaaaaa    960

cttgagaaat tatttaaaaa tttcgacgaa tactcgtcag ccggcatttt cgtgaaaaat   1020

ggtccggcca tttccacaat ctctaaggac atctttggag aatggaacgt tatccgtgac   1080

aaatggaacg ctgaatatga tgacatccat ttgaaaaaga aggctgtcgt tacagaaaaa   1140

tatgaagatg atcgccgcaa gagcttcaaa aagatcggtt cgttctcgct tgagcagttg   1200
```

```
caagaatacg cagatgccga tctgtcagta gtagagaaat taaaggaaat cattattcaa   1260
aaagtggacg agatttacaa agtttacgga tcctctgaga agctttttga tgcagatttt   1320
gtgttggaga aatcgttaaa aaagaatgat gccgtcgtgg caattatgaa agacttatta   1380
gatagcgtga agtccttcga gaattatatt aaggcgttct ttggagaggg taaggagaca   1440
aaccgcgacg aatcgtttta cggcgatttc gtgttggcct acgacatctt gctgaaagtt   1500
gatcacattt acgacgccat ccgtaactat gtaactcaga aaccctacag taaggacaag   1560
tttaagttat actttcagaa tccgcagttc atgcgtggat gggataagga caaagagaca   1620
gactaccgtg ctactatctt acgctacggg tcgaagtatt accttgcaat tatggataag   1680
aagtacgcaa aatgcttgca gaagatcgat aaagacgacg tcaacggaaa ttatgaaaag   1740
atcaattata aattattacc cgggcctaat aaaatgttgc ccaaagtatt tttctctaag   1800
aaatggatgg cctactacaa tccatcagaa gacattcaga agatctataa aaacggcaca   1860
ttcaaaaaag gcgatatgtt caacttgaac gattgccaca aactgattga tttctttaag   1920
gatagcatta gccgttaccc gaagtggtcc aacgcttatg actttaactt cagcgaaaca   1980
gagaagtata aagacattgc agggttctac cgtgaggtag aagaacaagg atataaagtt   2040
tctttcgaaa gtgcaagtaa gaaggaagta gataaattgg ttgaggaggg caaactgtat   2100
atgtttcaga tttacaataa ggatttctct gacaagtccc acggcacacc caatttgcat   2160
actatgtact tcaaacttct gtttgacgag aataaccatg ggcagatccg tcttagtggg   2220
ggagctgagt tatttatgcg ccgtgcgtct ttgaaaaagg aggagttagt tgttcacccg   2280
gcaaattcac ccattgccaa caaaaatcca gataacccca agaagacaac cactctttca   2340
tacgatgtgt acaaagataa gcgtttctct gaagatcaat acgaactgca tattccgatc   2400
gcaatcaaca agtgcccaaa gaacatcttt aaaatcaata cggaagttcg cgttcttctg   2460
aaacatgatg ataacccgta tgttattgga attgatcgtg gggagcgtaa cttgttgtat   2520
attgtcgtag tagatggaaa aggtaacatc gtcgaacagt actcgctgaa tgagattatt   2580
aacaacttca acgggattcg catcaagact gattaccact cacttcttga caaaaaggag   2640
aaggagcgct ttgaagcccg tcaaaattgg acatcaatcg aaaatattaa ggagctgaaa   2700
gccggataca tctctcaagt ggtccataaa atttgtgaac tggtcgagaa atatgatgcc   2760
gtgatcgcgc ttgaggacct gaatagtgga ttcaaaaact cgcgtgtgaa agttgagaaa   2820
caggtgtatc agaaatttga gaaaatgtta attgacaaat tgaactacat ggtagataaa   2880
aagagtaacc catgtgcgac gggcggtgca ttgaagggat accagatcac caataagttt   2940
gagtctttca aaagtatgtc tacgcagaat ggttttattt tctacatccc ggcttggctg   3000
acatctaaaa ttgacccttc gacgggtttt gtcaatctgc tgaaaacaaa gtatacaagt   3060
attgcggatt caaaaaaatt catctcatct ttcgatcgca tcatgtacgt cccagaagaa   3120
gacttatttg agtttgcact ggattataag aatttttccc gtactgacgc agactatatc   3180
aagaaatgga aattatattc atacgggaac cgcattcgta tcttccgtaa tcctaaaaag   3240
aacaacgttt tcgactggga agaagtatgc ttaaccagtg cttacaaaga attgttcaac   3300
aaatacggca ttaactacca gcagggcgac attcgcgcat tattatgcga acagtcagat   3360
aaagcgttct actccagctt tatggcgtta atgtcgctta tgttacagat gcgcaacagc   3420
attacaggcc gcaccgatgt cgattttctg atttcgccgg tgaaaaacag cgatggcatt   3480
ttttacgatt ctcgcaatta cgaggcgcag gaaaatgcaa ttcttccgaa gaacgcagac   3540
```

```
gcaaacggcg cttacaacat cgcacgtaaa gttctttggg cgatcggaca atttaaaaaa   3600

gccgaggatg aaaaattgga caaggttaaa attgctatct cgaataaaga gtggcttgag   3660

tacgcgcaaa cttctgttaa gcactga                                       3687
```

```
<210> SEQ ID NO 39
<211> LENGTH: 3687
<212> TYPE: DNA
<213> ORGANISM: Artificial Sequence
<220> FEATURE:
<223> OTHER INFORMATION: LbCpf1-K538R

<400> SEQUENCE: 39

atgtctaagc tggaaaaatt caccaactgc tacagtttaa gcaagacgtt acgcttcaag     60

gcgatcccgg ttgggaaaac acaagagaat attgacaaca aacgcctttt agttgaagat    120

gagaagcgtg cagaggacta taaaggagtt aagaagcttt tggaccgtta ctacttatcg    180

tttattaatg atgtgctgca ttccatcaaa ctgaagaatc tgaataatta cattagtctt    240

ttccgtaaga aaacacgtac tgagaaggaa aacaaggagc tggaaaatct tgagatcaat    300

ttgcgcaagg agattgctaa ggcattcaaa ggtaacgagg gatataagtc gttgtttaaa    360

aaagacatta ttgaaacgat ccttccggaa ttccttgacg ataaagacga gattgcactg    420

gtgaactcct tcaacgggtt cacgactgcc tttacgggtt tttttgacaa ccgcgagaat    480

atgttcagtg aagaagccaa atctacctct atcgctttcc gctgcattaa tgaaaacctg    540

actcgttata tctctaacat ggacatcttc gaaaaggtag acgcgatctt tgataaacac    600

gaagtgcagg agatcaagga gaaaattctt aatagcgact atgatgttga agatttcttt    660

gagggggaat tctttaactt tgtactgacg caagaaggga tcgacgtcta taacgctatt    720

atcggaggat tcgtaaccga gagtggagag aaaattaagg gtcttaatga gtacattaat    780

ttgtacaatc aaaaaacgaa acagaaattg cccaagttta aacctctgta taaacaagtg    840

ctgagtgatc gcgaaagttt gtcattctat ggagaggggt atactagcga cgaggaggtt    900

cttgaggtgt ttcgcaacac cttaaacaag aactctgaga ttttcagctc aatcaaaaaa    960

cttgagaaat tatttaaaaa tttcgacgaa tactcgtcag ccggcatttt cgtgaaaaat   1020

ggtccggcca tttccacaat ctctaaggac atctttggag aatggaacgt tatccgtgac   1080

aaatggaacg ctgaatatga tgacatccat ttgaaaaaga aggctgtcgt tacagaaaaa   1140

tatgaagatg atcgccgcaa gagcttcaaa aagatcggtt cgttctcgct tgagcagttg   1200

caagaatacg cagatgccga tctgtcagta gtagagaaat taaaggaaat cattattcaa   1260

aaagtggacg agatttacaa agtttacgga tcctctgaga agctttttga tgcagatttt   1320

gtgttggaga aatcgttaaa aaagaatgat gccgtcgtgg caattatgaa agacttatta   1380

gatagcgtga agtccttcga gaattatatt aaggcgttct ttggagaggg taaggagaca   1440

aaccgcgacg aatcgtttta cggcgatttc gtgttggcct acgacatctt gctgaaagtt   1500

gatcacattt acgacgccat ccgtaactat gtaactcaga aaccctacag taaggacaag   1560

tttaagttat actttcagaa tccgcagttc atgggtggat gggataagga ccgtgagaca   1620

gactaccgtg ctactatctt acgctacggg tcgaagtatt accttgcaat tatggataag   1680

aagtacgcaa aatgcttgca gaagatcgat aaagacgacg tcaacggaaa ttatgaaaag   1740

atcaattata aattattacc cgggcctaat aaaatgttgc ccaaagtatt tttctctaag   1800

aaatggatgg cctactacaa tccatcagaa gacattcaga agatctataa aaacggcaca   1860

ttcaaaaaag gcgatatgtt caacttgaac gattgccaca aactgattga tttctttaag   1920
```

```
gatagcatta gccgttaccc gaagtggtcc aacgcttatg actttaactt cagcgaaaca   1980

gagaagtata aagacattgc agggttctac cgtgaggtag aagaacaagg atataaagtt   2040

tctttcgaaa gtgcaagtaa gaaggaagta gataaattgg ttgaggaggg caaactgtat   2100

atgtttcaga tttacaataa ggatttctct gacaagtccc acggcacacc caatttgcat   2160

actatgtact tcaaacttct gtttgacgag aataaccatg ggcagatccg tcttagtggg   2220

ggagctgagt tatttatgcg ccgtgcgtct ttgaaaaagg aggagttagt tgttcacccg   2280

gcaaattcac ccattgccaa caaaaatcca gataacccca agaagacaac cactctttca   2340

tacgatgtgt acaaagataa gcgtttctct gaagatcaat acgaactgca tattccgatc   2400

gcaatcaaca agtgcccaaa gaacatcttt aaaatcaata cggaagttcg cgttcttctg   2460

aaacatgatg ataacccgta tgttattgga attgatcgtg gggagcgtaa cttgttgtat   2520

attgtcgtag tagatggaaa aggtaacatc gtcgaacagt actcgctgaa tgagattatt   2580

aacaacttca acgggattcg catcaagact gattaccact cacttcttga caaaaaggag   2640

aaggagcgct ttgaagcccg tcaaaattgg acatcaatcg aaaatattaa ggagctgaaa   2700

gccggataca tctctcaagt ggtccataaa atttgtgaac tggtcgagaa atatgatgcc   2760

gtgatcgcgc ttgaggacct gaatagtgga ttcaaaaact cgcgtgtgaa agttgagaaa   2820

caggtgtatc agaaatttga gaaaatgtta attgacaaat tgaactacat ggtagataaa   2880

aagagtaacc catgtgcgac gggcggtgca ttgaagggat accagatcac caataagttt   2940

gagtctttca aaagtatgtc tacgcagaat ggttttattt tctacatccc ggcttggctg   3000

acatctaaaa ttgacccttc gacgggtttt gtcaatctgc tgaaaacaaa gtatacaagt   3060

attgcggatt caaaaaaatt catctcatct ttcgatcgca tcatgtacgt cccagaagaa   3120

gacttatttg agtttgcact ggattataag aatttttccc gtactgacgc agactatatc   3180

aagaaatgga aattatattc atacgggaac cgcattcgta tcttccgtaa tcctaaaaag   3240

aacaacgttt tcgactggga agaagtatgc ttaaccagtg cttacaaaga attgttcaac   3300

aaatacggca ttaactacca gcagggcgac attcgcgcat tattatgcga acagtcagat   3360

aaagcgttct actccagctt tatggcgtta atgtcgctta tgttacagat gcgcaacagc   3420

attacaggcc gcaccgatgt cgattttctg atttcgccgg tgaaaaacag cgatggcatt   3480

ttttacgatt ctcgcaatta cgaggcgcag gaaaatgcaa ttcttccgaa gaacgcagac   3540

gcaaacggcg cttacaacat cgcacgtaaa gttctttggg cgatcggaca atttaaaaaa   3600

gccgaggatg aaaaattgga caaggttaaa attgctatct cgaataaaga gtggcttgag   3660

tacgcgcaaa cttctgttaa gcactga                                       3687
```

<210> SEQ ID NO 40
<211> LENGTH: 3687
<212> TYPE: DNA
<213> ORGANISM: Artificial Sequence
<220> FEATURE:
<223> OTHER INFORMATION: LbCpf1-T152R-G532R

<400> SEQUENCE: 40

```
atgtctaagc tggaaaaatt caccaactgc tacagtttaa gcaagacgtt acgcttcaag     60

gcgatcccgg ttgggaaaac acaagagaat attgacaaca aacgcctttt agttgaagat    120

gagaagcgtg cagaggacta taaaggagtt aagaagcttt tggaccgtta ctacttatcg    180

tttattaatg atgtgctgca ttccatcaaa ctgaagaatc tgaataatta cattagtctt    240
```

```
ttccgtaaga aaacacgtac tgagaaggaa aacaaggagc tggaaaatct tgagatcaat    300
ttgcgcaagg agattgctaa ggcattcaaa ggtaacgagg gatataagtc gttgtttaaa    360
aaagacatta ttgaaacgat ccttccggaa ttccttgacg ataaagacga gattgcactg    420
gtgaactcct tcaacgggtt cacgactgcc tttcgtggtt tttttgacaa ccgcgagaat    480
atgttcagtg aagaagccaa atctacctct atcgctttcc gctgcattaa tgaaaacctg    540
actcgttata tctctaacat ggacatcttc gaaaaggtag acgcgatctt tgataaacac    600
gaagtgcagg agatcaagga gaaaattctt aatagcgact atgatgttga agatttcttt    660
gagggggaat tctttaactt tgtactgacg caagaaggga tcgacgtcta taacgctatt    720
atcggaggat tcgtaaccga gagtggagag aaaattaagg gtcttaatga gtacattaat    780
ttgtacaatc aaaaaacgaa acagaaattg cccaagttta aacctctgta taaacaagtg    840
ctgagtgatc gcgaaagttt gtcattctat ggagaggggt atactagcga cgaggaggtt    900
cttgaggtgt ttcgcaacac cttaaacaag aactctgaga ttttcagctc aatcaaaaaa    960
cttgagaaat tatttaaaaa tttcgacgaa tactcgtcag ccggcatttt cgtgaaaaat   1020
ggtccggcca tttccacaat ctctaaggac atctttggag aatggaacgt tatccgtgac   1080
aaatggaacg ctgaatatga tgacatccat ttgaaaaaga aggctgtcgt tacagaaaaa   1140
tatgaagatg atcgccgcaa gagcttcaaa aagatcggtt cgttctcgct tgagcagttg   1200
caagaatacg cagatgccga tctgtcagta gtagagaaat taaaggaaat cattattcaa   1260
aaagtggacg agatttacaa agtttacgga tcctctgaga agctttttga tgcagatttt   1320
gtgttggaga aatcgttaaa aaagaatgat gccgtcgtgg caattatgaa agacttatta   1380
gatagcgtga agtccttcga gaattatatt aaggcgttct ttggagaggg taaggagaca   1440
aaccgcgacg aatcgtttta cggcgatttc gtgttggcct acgacatctt gctgaaagtt   1500
gatcacattt acgacgccat ccgtaactat gtaactcaga aaccctacag taaggacaag   1560
tttaagttat actttcagaa tccgcagttc atgcgtggat gggataagga caaagagaca   1620
gactaccgtg ctactatctt acgctacggg tcgaagtatt accttgcaat tatggataag   1680
aagtacgcaa aatgcttgca gaagatcgat aaagacgacg tcaacggaaa ttatgaaaag   1740
atcaattata aattattacc cgggcctaat aaaatgttgc ccaaagtatt tttctctaag   1800
aaatggatgg cctactacaa tccatcagaa gacattcaga agatctataa aaacggcaca   1860
ttcaaaaaag gcgatatgtt caacttgaac gattgccaca aactgattga tttctttaag   1920
gatagcatta gccgttaccc gaagtggtcc aacgcttatg actttaactt cagcgaaaca   1980
gagaagtata aagacattgc agggttctac cgtgaggtag aagaacaagg atataaagtt   2040
tctttcgaaa gtgcaagtaa gaaggaagta gataaattgg ttgaggaggg caaactgtat   2100
atgtttcaga tttacaataa ggatttctct gacaagtccc acggcacacc caatttgcat   2160
actatgtact tcaaacttct gtttgacgag aataaccatg ggcagatccg tcttagtggg   2220
ggagctgagt tatttatgcg ccgtgcgtct ttgaaaaagg aggagttagt tgttcacccg   2280
gcaaattcac ccattgccaa caaaaatcca gataacccca agaagacaac cactctttca   2340
tacgatgtgt acaaagataa gcgtttctct gaagatcaat acgaactgca tattccgatc   2400
gcaatcaaca agtgcccaaa gaacatcttt aaaatcaata cggaagttcg cgttcttctg   2460
aaacatgatg ataacccgta tgttattgga attgatcgtg gggagcgtaa cttgttgtat   2520
attgtcgtag tagatggaaa aggtaacatc gtcgaacagt actcgctgaa tgagattatt   2580
aacaacttca acgggattcg catcaagact gattaccact cacttcttga caaaaaggag   2640
```

```
aaggagcgct ttgaagcccg tcaaaattgg acatcaatcg aaaatattaa ggagctgaaa   2700

gccggataca tctctcaagt ggtccataaa atttgtgaac tggtcgagaa atatgatgcc   2760

gtgatcgcgc ttgaggacct gaatagtgga ttcaaaaact cgcgtgtgaa agttgagaaa   2820

caggtgtatc agaaatttga gaaaatgtta attgacaaat tgaactacat ggtagataaa   2880

aagagtaacc catgtgcgac gggcggtgca ttgaagggat accagatcac caataagttt   2940

gagtctttca aaagtatgtc tacgcagaat ggttttattt tctacatccc ggcttggctg   3000

acatctaaaa ttgacccttc gacgggtttt gtcaatctgc tgaaaacaaa gtatacaagt   3060

attgcggatt caaaaaaatt catctcatct ttcgatcgca tcatgtacgt cccagaagaa   3120

gacttatttg agtttgcact ggattataag aatttttccc gtactgacgc agactatatc   3180

aagaaatgga aattatattc atacgggaac cgcattcgta tcttccgtaa tcctaaaaag   3240

aacaacgttt tcgactggga agaagtatgc ttaaccagtg cttacaaaga attgttcaac   3300

aaatacggca ttaactacca gcagggcgac attcgcgcat tattatgcga acagtcagat   3360

aaagcgttct actccagctt tatggcgtta atgtcgctta tgttacagat gcgcaacagc   3420

attacaggcc gcaccgatgt cgattttctg atttcgccgg tgaaaaacag cgatggcatt   3480

ttttacgatt ctcgcaatta cgaggcgcag gaaaatgcaa ttcttccgaa gaacgcagac   3540

gcaaacggcg cttacaacat cgcacgtaaa gttctttggg cgatcggaca atttaaaaaa   3600

gccgaggatg aaaaattgga caaggttaaa attgctatct cgaataaaga gtggcttgag   3660

tacgcgcaaa cttctgttaa gcactga                                        3687
```

<210> SEQ ID NO 41
<211> LENGTH: 3687
<212> TYPE: DNA
<213> ORGANISM: Artificial Sequence
<220> FEATURE:
<223> OTHER INFORMATION: LbCpf1-T152R-G532R-K538R

<400> SEQUENCE: 41

```
atgtctaagc tggaaaaatt caccaactgc tacagtttaa gcaagacgtt acgcttcaag     60

gcgatcccgg ttgggaaaac acaagagaat attgacaaca aacgcctttt agttgaagat    120

gagaagcgtg cagaggacta taaaggagtt aagaagcttt tggaccgtta ctacttatcg    180

tttattaatg atgtgctgca ttccatcaaa ctgaagaatc tgaataatta cattagtctt    240

ttccgtaaga aaacacgtac tgagaaggaa aacaaggagc tggaaaatct tgagatcaat    300

ttgcgcaagg agattgctaa ggcattcaaa ggtaacgagg gatataagtc gttgtttaaa    360

aaagacatta ttgaaacgat ccttccggaa ttccttgacg ataaagacga gattgcactg    420

gtgaactcct tcaacgggtt cacgactgcc tttcgtggtt tttttgacaa ccgcgagaat    480

atgttcagtg aagaagccaa atctacctct atcgctttcc gctgcattaa tgaaaacctg    540

actcgttata tctctaacat ggacatcttc gaaaaggtag acgcgatctt tgataaacac    600

gaagtgcagg agatcaagga gaaaattctt aatagcgact atgatgttga agatttcttt    660

gagggggaat tctttaactt tgtactgacg caagaaggga tcgacgtcta taacgctatt    720

atcggaggat tcgtaaccga gagtggagag aaaattaagg gtcttaatga gtacattaat    780

ttgtacaatc aaaaaacgaa acagaaattg cccaagttta aacctctgta taaacaagtg    840

ctgagtgatc gcgaaagttt gtcattctat ggagaggggt atactagcga cgaggaggtt    900

cttgaggtgt ttcgcaacac cttaaacaag aactctgaga ttttcagctc aatcaaaaaa    960
```

```
cttgagaaat tatttaaaaa tttcgacgaa tactcgtcag ccggcatttt cgtgaaaaat   1020
ggtccggcca tttccacaat ctctaaggac atctttggag aatggaacgt tatccgtgac   1080
aaatggaacg ctgaatatga tgacatccat ttgaaaaaga aggctgtcgt tacagaaaaa   1140
tatgaagatg atcgccgcaa gagcttcaaa aagatcggtt cgttctcgct tgagcagttg   1200
caagaatacg cagatgccga tctgtcagta gtagagaaat taaaggaaat cattattcaa   1260
aaagtggacg agatttacaa agtttacgga tcctctgaga agcttttga tgcagatttt    1320
gtgttggaga aatcgttaaa aaagaatgat gccgtcgtgg caattatgaa agacttatta   1380
gatagcgtga agtccttcga gaattatatt aaggcgttct ttggagaggg taaggagaca   1440
aaccgcgacg aatcgtttta cggcgatttc gtgttggcct acgacatctt gctgaaagtt   1500
gatcacattt acgacgccat ccgtaactat gtaactcaga aaccctacag taaggacaag   1560
tttaagttat actttcagaa tccgcagttc atgcgtggat gggataagga ccgtgagaca   1620
gactaccgtg ctactatctt acgctacggg tcgaagtatt accttgcaat tatggataag   1680
aagtacgcaa aatgcttgca gaagatcgat aaagacgacg tcaacggaaa ttatgaaaag   1740
atcaattata aattattacc cgggcctaat aaaatgttgc ccaaagtatt tttctctaag   1800
aaatggatgg cctactacaa tccatcagaa gacattcaga agatctataa aaacggcaca   1860
ttcaaaaaag gcgatatgtt caacttgaac gattgccaca aactgattga tttctttaag   1920
gatagcatta gccgttaccc gaagtggtcc aacgcttatg actttaactt cagcgaaaca   1980
gagaagtata aagacattgc agggttctac cgtgaggtag aagaacaagg atataaagtt   2040
tctttcgaaa gtgcaagtaa gaaggaagta gataaattgg ttgaggaggg caaactgtat   2100
atgtttcaga tttacaataa ggatttctct gacaagtccc acggcacacc caatttgcat   2160
actatgtact tcaaacttct gtttgacgag aataaccatg ggcagatccg tcttagtggg   2220
ggagctgagt tatttatgcg ccgtgcgtct ttgaaaaagg aggagttagt tgttcacccg   2280
gcaaattcac ccattgccaa caaaaatcca gataacccca agaagacaac cactctttca   2340
tacgatgtgt acaaagataa gcgtttctct gaagatcaat acgaactgca tattccgatc   2400
gcaatcaaca agtgcccaaa gaacatcttt aaaatcaata cggaagttcg cgttcttctg   2460
aaacatgatg ataacccgta tgttattgga attgatcgtg gggagcgtaa cttgttgtat   2520
attgtcgtag tagatggaaa aggtaacatc gtcgaacagt actcgctgaa tgagattatt   2580
aacaacttca acgggattcg catcaagact gattaccact cacttcttga caaaaaggag   2640
aaggagcgct ttgaagcccg tcaaaattgg acatcaatcg aaaatattaa ggagctgaaa   2700
gccggataca tctctcaagt ggtccataaa atttgtgaac tggtcgagaa atatgatgcc   2760
gtgatcgcgc ttgaggacct gaatagtgga ttcaaaaact cgcgtgtgaa agttgagaaa   2820
caggtgtatc agaaatttga gaaaatgtta attgacaaat tgaactacat ggtagataaa   2880
aagagtaacc catgtgcgac gggcggtgca ttgaagggat accagatcac caataagttt   2940
gagtctttca aaagtatgtc tacgcagaat ggttttattt tctacatccc ggcttggctg   3000
acatctaaaa ttgacccttc gacgggtttt gtcaatctgc tgaaaacaaa gtatacaagt   3060
attgcggatt caaaaaaatt catctcatct ttcgatcgca tcatgtacgt cccagaagaa   3120
gacttatttg agtttgcact ggattataag aatttttccc gtactgacgc agactatatc   3180
aagaaatgga aattatattc atacgggaac cgcattcgta tcttccgtaa tcctaaaaag   3240
aacaacgttt tcgactggga agaagtatgc ttaaccagtg cttacaaaga attgttcaac   3300
aaatacggca ttaactacca gcagggcgac attcgcgcat tattatgcga acagtcagat   3360
```

```
aaagcgttct actccagctt tatggcgtta atgtcgctta tgttacagat gcgcaacagc   3420

attacaggcc gcaccgatgt cgattttctg atttcgccgg tgaaaaacag cgatggcatt   3480

ttttacgatt ctcgcaatta cgaggcgcag gaaaatgcaa ttcttccgaa gaacgcagac   3540

gcaaacggcg cttacaacat cgcacgtaaa gttctttggg cgatcggaca atttaaaaaa   3600

gccgaggatg aaaaattgga caaggttaaa attgctatct cgaataaaga gtggcttgag   3660

tacgcgcaaa cttctgttaa gcactga                                        3687
```

```
<210> SEQ ID NO 42
<211> LENGTH: 3687
<212> TYPE: DNA
<213> ORGANISM: Artificial Sequence
<220> FEATURE:
<223> OTHER INFORMATION: LbCpf1-K536R

<400> SEQUENCE: 42

atgtctaagc tggaaaaatt caccaactgc tacagtttaa gcaagacgtt acgcttcaag     60

gcgatcccgg ttgggaaaac acaagagaat attgacaaca aacgcctttt agttgaagat    120

gagaagcgtg cagaggacta taaaggagtt aagaagcttt tggaccgtta ctacttatcg    180

tttattaatg atgtgctgca ttccatcaaa ctgaagaatc tgaataatta cattagtctt    240

ttccgtaaga aaacacgtac tgagaaggaa aacaaggagc tggaaaatct tgagatcaat    300

ttgcgcaagg agattgctaa ggcattcaaa ggtaacgagg gatataagtc gttgtttaaa    360

aaagacatta ttgaaacgat ccttccggaa ttccttgacg ataaagacga gattgcactg    420

gtgaactcct tcaacgggtt cacgactgcc tttacgggtt tttttgacaa ccgcgagaat    480

atgttcagtg aagaagccaa atctacctct atcgctttcc gctgcattaa tgaaaacctg    540

actcgttata tctctaacat ggacatcttc gaaaaggtag acgcgatctt tgataaacac    600

gaagtgcagg agatcaagga gaaaattctt aatagcgact atgatgttga agatttcttt    660

gagggggaat tctttaactt tgtactgacg caagaaggga tcgacgtcta taacgctatt    720

atcggaggat tcgtaaccga gagtggagag aaaattaagg gtcttaatga gtacattaat    780

ttgtacaatc aaaaaacgaa acagaaattg cccaagttta aacctctgta taaacaagtg    840

ctgagtgatc gcgaaagttt gtcattctat ggagaggggt atactagcga cgaggaggtt    900

cttgaggtgt ttcgcaacac cttaaacaag aactctgaga ttttcagctc aatcaaaaaa    960

cttgagaaat tatttaaaaa tttcgacgaa tactcgtcag ccggcatttt cgtgaaaaat   1020

ggtccggcca tttccacaat ctctaaggac atctttggag aatggaacgt tatccgtgac   1080

aaatggaacg ctgaatatga tgacatccat ttgaaaaaga aggctgtcgt tacagaaaaa   1140

tatgaagatg atcgccgcaa gagcttcaaa aagatcggtt cgttctcgct tgagcagttg   1200

caagaatacg cagatgccga tctgtcagta gtagagaaat taaaggaaat cattattcaa   1260

aaagtggacg agatttacaa agtttacgga tcctctgaga agctttttga tgcagatttt   1320

gtgttggaga aatcgttaaa aaagaatgat gccgtcgtgg caattatgaa agacttatta   1380

gatagcgtga agtccttcga gaattatatt aaggcgttct ttggagaggg taaggagaca   1440

aaccgcgacg aatcgtttta cggcgatttc gtgttggcct acgacatctt gctgaaagtt   1500

gatcacattt acgacgccat ccgtaactat gtaactcaga aaccctacag taaggacaag   1560

tttaagttat actttcagaa tccgcagttc atgggtggat gggatcgcga caaagagaca   1620

gactaccgtg ctactatctt acgctacggg tcgaagtatt accttgcaat tatggataag   1680
```

```
aagtacgcaa aatgcttgca gaagatcgat aaagacgacg tcaacggaaa ttatgaaaag   1740
atcaattata aattattacc cgggcctaat aaaatgttgc ccaaagtatt tttctctaag   1800
aaatggatgg cctactacaa tccatcagaa gacattcaga agatctataa aaacggcaca   1860
ttcaaaaaag gcgatatgtt caacttgaac gattgccaca aactgattga tttctttaag   1920
gatagcatta gccgttaccc gaagtggtcc aacgcttatg actttaactt cagcgaaaca   1980
gagaagtata aagacattgc agggttctac cgtgaggtag aagaacaagg atataaagtt   2040
tctttcgaaa gtgcaagtaa gaaggaagta gataaattgg ttgaggaggg caaactgtat   2100
atgtttcaga tttacaataa ggatttctct gacaagtccc acggcacacc caatttgcat   2160
actatgtact tcaaacttct gtttgacgag aataaccatg ggcagatccg tcttagtggg   2220
ggagctgagt tatttatgcg ccgtgcgtct ttgaaaaagg aggagttagt tgttcacccg   2280
gcaaattcac ccattgccaa caaaaatcca gataacccca agaagacaac cactctttca   2340
tacgatgtgt acaaagataa gcgtttctct gaagatcaat acgaactgca tattccgatc   2400
gcaatcaaca agtgcccaaa gaacatcttt aaaatcaata cggaagttcg cgttcttctg   2460
aaacatgatg ataacccgta tgttattgga attgatcgtg gggagcgtaa cttgttgtat   2520
attgtcgtag tagatggaaa aggtaacatc gtcgaacagt actcgctgaa tgagattatt   2580
aacaacttca acgggattcg catcaagact gattaccact cacttcttga caaaaaggag   2640
aaggagcgct ttgaagcccg tcaaaattgg acatcaatcg aaaatattaa ggagctgaaa   2700
gccggataca tctctcaagt ggtccataaa atttgtgaac tggtcgagaa atatgatgcc   2760
gtgatcgcgc ttgaggacct gaatagtgga ttcaaaaact cgcgtgtgaa agttgagaaa   2820
caggtgtatc agaaatttga gaaaatgtta attgacaaat tgaactacat ggtagataaa   2880
aagagtaacc catgtgcgac gggcggtgca ttgaagggat accagatcac caataagttt   2940
gagtctttca aaagtatgtc tacgcagaat ggttttattt tctacatccc ggcttggctg   3000
acatctaaaa ttgacccttc gacgggtttt gtcaatctgc tgaaaacaaa gtatacaagt   3060
attgcggatt caaaaaaatt catctcatct ttcgatcgca tcatgtacgt cccagaagaa   3120
gacttatttg agtttgcact ggattataag aatttttccc gtactgacgc agactatatc   3180
aagaaatgga aattatattc atacgggaac cgcattcgta tcttccgtaa tcctaaaaag   3240
aacaacgttt tcgactggga agaagtatgc ttaaccagtg cttacaaaga attgttcaac   3300
aaatacggca ttaactacca gcagggcgac attcgcgcat tattatgcga acagtcagat   3360
aaagcgttct actccagctt tatggcgtta atgtcgctta tgttacagat gcgcaacagc   3420
attacaggcc gcaccgatgt cgattttctg atttcgccgg tgaaaaacag cgatggcatt   3480
ttttacgatt ctcgcaatta cgaggcgcag gaaaatgcaa ttcttccgaa gaacgcagac   3540
gcaaacggcg cttacaacat cgcacgtaaa gttctttggg cgatcggaca atttaaaaaa   3600
gccgaggatg aaaaattgga caaggttaaa attgctatct cgaataaaga gtggcttgag   3660
tacgcgcaaa cttctgttaa gcactga                                       3687
```

<210> SEQ ID NO 43
<211> LENGTH: 3903
<212> TYPE: DNA
<213> ORGANISM: Artificial Sequence
<220> FEATURE:
<223> OTHER INFORMATION: FnCpf1-K611R

<400> SEQUENCE: 43

```
atgtctatct accaggagtt tgtaaacaag tattctctta gtaaaacgtt gcgttttgaa     60
```

```
cttattccac agggtaaaac cctggagaat attaaggctc gtggcttaat tcttgatgac    120
gaaaagcgcg caaaggatta caaaaaggca aaacaaatta ttgataagta ccatcagttc    180
ttcattgaag agattttatc cagcgtttgt atctccgagg acctgttaca gaactacagc    240
gatgtatatt tcaaattgaa aaaatccgat gatgacaatc tgcaaaagga ttttaaatcg    300
gccaaggaca ctatcaagaa acaaatttct gagtacatca aagatagcga gaaattcaag    360
aatttattta accaaaatct gatcgacgcg aagaaggggc aggagtcaga cttgattttg    420
tggttgaaac agtcgaaaga taatggaatc gaactgttca aagccaactc tgacattaca    480
gatattgatg aagctctgga aattattaag agctttaagg ggtggaccac ctatttcaaa    540
gggttccacg agaaccgtaa aaacgtgtac tcttcgaatg atattcctac tagcattatt    600
tatcgtattg tagacgacaa ccttcctaaa ttcttggaga ataaagctaa atatgaatcg    660
ctgaaggata aggcgcccga agcaatcaat tacgaacaaa tcaaaaaaga tctggctgaa    720
gaactgacct ttgacattga ctataaaact tctgaagtaa accagcgcgt tttcagtctt    780
gacgaggttt ttgaaatcgc taattttaat aattatttaa atcaatccgg gattacaaaa    840
tttaacacga ttattggtgg caagttcgta aatggagaga acactaagcg taagggaatt    900
aacgagtaca ttaatttata ctcgcagcag attaacgaca aaacgctgaa aaaatataaa    960
atgagcgttt tatttaagca aattctgagc gataccgagt caaagtcctt cgtaattgac   1020
aagcttgagg atgactctga cgttgtcacg acgatgcagt cattctatga acagattgcg   1080
gcttttaaaa ccgtggaaga aaaatcaatc aaagagacct tgtcattatt atttgacgat   1140
ctgaaagctc aaaagttgga cttaagtaag atctacttta agaatgataa gagtctgacg   1200
gatttatccc aacaagtctt tgacgactac tctgtaattg gcacagccgt cttggaatac   1260
atcacccaac aaatcgctcc taaaaattta gacaatccga gtaaaaagga acaagagctg   1320
attgcaaaaa agaccgagaa agcgaaatat ttatcgttag aaactattaa attagcgctg   1380
gaagaattta ataaacaccg tgacattgac aagcaatgtc gtttcgaaga gattttagct   1440
aactttgcgg ccatcccgat gatctttgac gagattgcac aaaataaaga caatcttgcg   1500
cagatctcga ttaagtatca gaaccaaggt aagaaagacc tgttgcaggc ttccgcagag   1560
gatgacgtta aagcgatcaa agatctgtta gaccaaacca acaatttgct tcacaagtta   1620
aagatttttc acatttcaca gtcagaggat aaagcaaaca ttcttgataa agacgaacac   1680
ttttatttag ttttcgagga atgttatttt gagctggcga acattgttcc cctttataat   1740
aagatccgta attatatcac tcagaaacct tattctgacg agaaattcaa gttgaatttt   1800
gaaaactcca ctcttgcgaa cggctgggat cgcaataagg aacccgataa tactgccatt   1860
ctgtttatta aagacgacaa atattactta ggagttatga ataagaaaaa caataagatc   1920
tttgatgaca aagctattaa ggagaacaaa ggcgagggct acaaaaaaat tgtatacaaa   1980
cttctgcctg gagctaacaa gatgttgcca aaagtatttt tcagtgcaaa atcgattaag   2040
ttctacaacc catcggagga tattttacgt attcgcaacc attccaccca tacgaaaaat   2100
gggtcacccc aaaagggtta cgaaaagttt gagtttaata ttgaagattg ccgtaagttt   2160
attgattttt ataaacaatc tatctctaaa caccccgaat ggaaggattt cggattccgt   2220
ttctctgaca cacaacgcta caattcgatc gatgaattct atcgtgaggt tgagaaccaa   2280
ggatataagt tgacatttga aaacatttcc gaatcataca tcgattcggt cgtgaaccag   2340
ggtaagttat atttatttca gatctacaac aaggattttt ccgcctatag caaaggccgt   2400
```

```
ccgaacttac atacgttgta ctggaaggcc ctgtttgatg agcgcaatct gcaagatgtc   2460

gtatataagt taaatggcga agctgaactg ttttaccgca agcagtcgat cccgaagaag   2520

atcacacatc ctgctaagga ggcaattgct aacaagaata aagacaatcc aaagaaagaa   2580

agtgtcttcg agtatgactt aattaaagat aaacgtttta ctgaggacaa gtttttcttt   2640

cattgcccaa tcacaatcaa tttcaaatca agtggagcaa acaagtttaa cgacgaaatt   2700

aacttactgc tgaaggaaaa ggcgaatgac gtgcacattc tgtccattga tcgcggagaa   2760

cgtcacctgg cgtactatac gttggtcgac gggaagggaa acatcattaa acaggacacg   2820

tttaatatta tcggcaatga tcgcatgaag acaaattatc acgacaagct ggcggcaatt   2880

gagaaggatc gtgactcagc tcgcaaagac tggaagaaga ttaacaacat caaggagatg   2940

aaagagggtt atcttagcca agtcgtccat gagattgcaa aattggttat tgaatacaat   3000

gcgattgttg tcttcgaaga tcttaatttt gggttcaaac gtggtcgctt caaagtcgag   3060

aagcaggttt accaaaagct ggaaaagatg cttattgaga aattgaatta cttggttttc   3120

aaggacaatg aattcgataa gacaggcggt gtacttcgtg cgtatcaact tacggcaccc   3180

tttgaaacct tcaaaaaaat gggcaaacaa actgggatca tctactacgt gccggcgggg   3240

ttcaccagca aaatttgtcc tgtaactggg ttcgtgaacc agttgtaccc caaatacgaa   3300

tcagtcagta agtcccagga gtttttttct aagttcgata agatctgtta taatcttgac   3360

aaaggctact ttgagttttc tttcgattat aagaactttg gcgataaagc agccaaaggg   3420

aagtggacta ttgcgtcgtt cggctcacgt cttatcaact ttcgcaacag cgataagaac   3480

cataactggg atacacgtga agtttatcca acgaaggagc ttgagaagtt attaaaagat   3540

tacagtattg aatatgggca cggggagtgc attaaagcag ctatctgtgg tgagtcggac   3600

aagaaattct tcgcaaaact gacgtctgtt cttaatacca tccttcaaat gcgtaattcc   3660

aagacgggta cggagctgga ttacctgatc agtcccgttg ccgatgttaa tggtaatttt   3720

ttcgactcgc gtcaggcccc gaagaacatg cctcaggacg ccgatgccaa cggtgcgtac   3780

catattggcc ttaagggctt aatgctgtta ggacgtatta agaacaacca ggagggtaaa   3840

aaactgaatc tggtcattaa aaacgaagaa tatttcgaat ttgtacagaa ccgcaataac   3900

tga                                                                 3903
```

<210> SEQ ID NO 44
<211> LENGTH: 32
<212> TYPE: DNA
<213> ORGANISM: Artificial Sequence
<220> FEATURE:
<223> OTHER INFORMATION: CoV2-E- RPA-F

<400> SEQUENCE: 44

```
tgtactcatt cgtttcggaa gagacaggta cg                                   32
```

<210> SEQ ID NO 45
<211> LENGTH: 35
<212> TYPE: DNA
<213> ORGANISM: Artificial Sequence
<220> FEATURE:
<223> OTHER INFORMATION: Cov2-E- RPA-R

<400> SEQUENCE: 45

```
tagaccagaa gatcaggaac tctagaagaa ttcag                                35
```

<210> SEQ ID NO 46
<211> LENGTH: 308

<212> TYPE: DNA
<213> ORGANISM: Artificial Sequence
<220> FEATURE:
<223> OTHER INFORMATION: SARS-CoV-2-E

<400> SEQUENCE: 46
taatacgact cactataggg agatctagaa ataattttgt ttaactttaa gaaggagata 60
taccatgatg tactcattcg tttcggaaga gacaggtacg ttaatagtta atagcgtact 120
tctttttctt gctttcgtgg tattcttgct agttacacta gccatcctta ctgcgcttcg 180
attgtgtgcg tactgctgca atattgttaa cgtgagtctt gtaaaacctt ctttttacgt 240
ttactctcgt gttaaaaatc tgaattcttc tagagttcct gatcttctgg tctaattttt 300
ttgaattc 308

<210> SEQ ID NO 47
<211> LENGTH: 44
<212> TYPE: RNA
<213> ORGANISM: Artificial Sequence
<220> FEATURE:
<223> OTHER INFORMATION: CoV2-E-Cr1

<400> SEQUENCE: 47
uaauuucuac uaaguguaga uacaagacuc acguuaacaa uauu 44

<210> SEQ ID NO 48
<211> LENGTH: 44
<212> TYPE: RNA
<213> ORGANISM: Artificial Sequence
<220> FEATURE:
<223> OTHER INFORMATION: CoV2-E-Cr2

<400> SEQUENCE: 48
uaauuucuac uaaguguaga uacacgagag uaaacguaaa aaga 44

<210> SEQ ID NO 49
<211> LENGTH: 44
<212> TYPE: RNA
<213> ORGANISM: Artificial Sequence
<220> FEATURE:
<223> OTHER INFORMATION: CoV2-E-Cr3

<400> SEQUENCE: 49
uaauuucuac uaaguguaga uaacacgaga guaaacguaa aaag 44

<210> SEQ ID NO 50
<211> LENGTH: 44
<212> TYPE: RNA
<213> ORGANISM: Artificial Sequence
<220> FEATURE:
<223> OTHER INFORMATION: CoV2-E-Cr4

<400> SEQUENCE: 50
uaauuucuac uaaguguaga uuacguuuac ucucguguua aaaa 44

<210> SEQ ID NO 51
<211> LENGTH: 44
<212> TYPE: RNA
<213> ORGANISM: Artificial Sequence
<220> FEATURE:
<223> OTHER INFORMATION: CoV2-E-Cr5

<400> SEQUENCE: 51
uaauuucuac uaaguguaga uuaacacgag aguaaacgua aaaa 44

<210> SEQ ID NO 52
<211> LENGTH: 44
<212> TYPE: RNA
<213> ORGANISM: Artificial Sequence
<220> FEATURE:
<223> OTHER INFORMATION: CoV2-E-Cr6

<400> SEQUENCE: 52
uaauuucuac uaaguguaga uacguuuacu cucguguuaa aaau 44

<210> SEQ ID NO 53
<211> LENGTH: 44
<212> TYPE: RNA
<213> ORGANISM: Artificial Sequence
<220> FEATURE:
<223> OTHER INFORMATION: CoV2-E-Cr7

<400> SEQUENCE: 53
uaauuucuac uaaguguaga ucguuuacuc ucguguuaaa aauc 44

<210> SEQ ID NO 54
<211> LENGTH: 1228
<212> TYPE: PRT
<213> ORGANISM: Lachnospiraceae bacterium ND2006

<400> SEQUENCE: 54

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255
```

```
Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670
```

```
Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
            725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
            805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
            885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
            965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
        995                 1000                 1005

Gly Phe  Val Asn Leu Leu Lys  Thr Lys Tyr Thr Ser  Ile Ala Asp
    1010                 1015                 1020

Ser Lys  Lys Phe Ile Ser Ser  Phe Asp Arg Ile Met  Tyr Val Pro
    1025                 1030                 1035

Glu Glu  Asp Leu Phe Glu Phe  Ala Leu Asp Tyr Lys  Asn Phe Ser
    1040                 1045                 1050

Arg Thr  Asp Ala Asp Tyr Ile  Lys Lys Trp Lys Leu  Tyr Ser Tyr
    1055                 1060                 1065

Gly Asn  Arg Ile Arg Ile Phe  Arg Asn Pro Lys Lys  Asn Asn Val
    1070                 1075                 1080

Phe Asp  Trp Glu Glu Val Cys  Leu Thr Ser Ala Tyr  Lys Glu Leu
```

```
    1085                1090                1095

Phe Asn  Lys Tyr Gly Ile Asn  Tyr Gln Gln Gly Asp  Ile Arg Ala
    1100                1105                1110

Leu Leu  Cys Glu Gln Ser Asp  Lys Ala Phe Tyr Ser  Ser Phe Met
    1115                1120                1125

Ala Leu  Met Ser Leu Met Leu  Gln Met Arg Asn Ser  Ile Thr Gly
    1130                1135                1140

Arg Thr  Asp Val Asp Phe Leu  Ile Ser Pro Val Lys  Asn Ser Asp
    1145                1150                1155

Gly Ile  Phe Tyr Asp Ser Arg  Asn Tyr Glu Ala Gln  Glu Asn Ala
    1160                1165                1170

Ile Leu  Pro Lys Asn Ala Asp  Ala Asn Gly Ala Tyr  Asn Ile Ala
    1175                1180                1185

Arg Lys  Val Leu Trp Ala Ile  Gly Gln Phe Lys Lys  Ala Glu Asp
    1190                1195                1200

Glu Lys  Leu Asp Lys Val Lys  Ile Ala Ile Ser Asn  Lys Glu Trp
    1205                1210                1215

Leu Glu  Tyr Ala Gln Thr Ser  Val Lys His
    1220                1225


<210> SEQ ID NO 55
<211> LENGTH: 1300
<212> TYPE: PRT
<213> ORGANISM: Francisella novicida U112

<400> SEQUENCE: 55

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220
```

```
Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
```

```
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
    1055                1060                1065
```

```
Lys Gln  Thr Gly Ile Ile Tyr  Tyr Val Pro Ala Gly  Phe Thr Ser
    1070                 1075                 1080

Lys Ile  Cys Pro Val Thr Gly  Phe Val Asn Gln Leu  Tyr Pro Lys
    1085                 1090                 1095

Tyr Glu  Ser Val Ser Lys Ser  Gln Glu Phe Phe Ser  Lys Phe Asp
    1100                 1105                 1110

Lys Ile  Cys Tyr Asn Leu Asp  Lys Gly Tyr Phe Glu  Phe Ser Phe
    1115                 1120                 1125

Asp Tyr  Lys Asn Phe Gly Asp  Lys Ala Ala Lys Gly  Lys Trp Thr
    1130                 1135                 1140

Ile Ala  Ser Phe Gly Ser Arg  Leu Ile Asn Phe Arg  Asn Ser Asp
    1145                 1150                 1155

Lys Asn  His Asn Trp Asp Thr  Arg Glu Val Tyr Pro  Thr Lys Glu
    1160                 1165                 1170

Leu Glu  Lys Leu Leu Lys Asp  Tyr Ser Ile Glu Tyr  Gly His Gly
    1175                 1180                 1185

Glu Cys  Ile Lys Ala Ala Ile  Cys Gly Glu Ser Asp  Lys Lys Phe
    1190                 1195                 1200

Phe Ala  Lys Leu Thr Ser Val  Leu Asn Thr Ile Leu  Gln Met Arg
    1205                 1210                 1215

Asn Ser  Lys Thr Gly Thr Glu  Leu Asp Tyr Leu Ile  Ser Pro Val
    1220                 1225                 1230

Ala Asp  Val Asn Gly Asn Phe  Phe Asp Ser Arg Gln  Ala Pro Lys
    1235                 1240                 1245

Asn Met  Pro Gln Asp Ala Asp  Ala Asn Gly Ala Tyr  His Ile Gly
    1250                 1255                 1260

Leu Lys  Gly Leu Met Leu Leu  Gly Arg Ile Lys Asn  Asn Gln Glu
    1265                 1270                 1275

Gly Lys  Lys Leu Asn Leu Val  Ile Lys Asn Glu Glu  Tyr Phe Glu
    1280                 1285                 1290

Phe Val  Gln Asn Arg Asn Asn
    1295                 1300
```

<210> SEQ ID NO 56
<211> LENGTH: 44
<212> TYPE: RNA
<213> ORGANISM: Artificial Sequence
<220> FEATURE:
<223> OTHER INFORMATION: CoV2-S-cr3

<400> SEQUENCE: 56
uaauuucuac uaaguguaga uacaagacuc acguuaacaa uauu 44

<210> SEQ ID NO 57
<211> LENGTH: 44
<212> TYPE: RNA
<213> ORGANISM: Artificial Sequence
<220> FEATURE:
<223> OTHER INFORMATION: CoV2-S-cr4

<400> SEQUENCE: 57
uaauuucuac uaaguguaga uacacgagag uaaacguaaa aaga 44

<210> SEQ ID NO 58
<211> LENGTH: 44
<212> TYPE: RNA
<213> ORGANISM: Artificial Sequence
<220> FEATURE:

<223> OTHER INFORMATION: CoV2-S-cr5

<400> SEQUENCE: 58
uaauuucuac uaaguguaga uaacacgaga guaaacguaa aaag 44

<210> SEQ ID NO 59
<211> LENGTH: 44
<212> TYPE: RNA
<213> ORGANISM: Artificial Sequence
<220> FEATURE:
<223> OTHER INFORMATION: CoV2-S-cr6

<400> SEQUENCE: 59
uaauuucuac uaaguguaga uuacguuuac ucucguguua aaaa 44

<210> SEQ ID NO 60
<211> LENGTH: 44
<212> TYPE: RNA
<213> ORGANISM: Artificial Sequence
<220> FEATURE:
<223> OTHER INFORMATION: CoV2-S-cr7

<400> SEQUENCE: 60
uaauuucuac uaaguguaga uuaacacgag aguaaacgua aaaa 44

<210> SEQ ID NO 61
<211> LENGTH: 44
<212> TYPE: RNA
<213> ORGANISM: Artificial Sequence
<220> FEATURE:
<223> OTHER INFORMATION: CoV2-S-cr8

<400> SEQUENCE: 61
uaauuucuac uaaguguaga uacguuuacu cucguguuaa aaau 44

<210> SEQ ID NO 62
<211> LENGTH: 44
<212> TYPE: RNA
<213> ORGANISM: Artificial Sequence
<220> FEATURE:
<223> OTHER INFORMATION: CoV2-S-cr9

<400> SEQUENCE: 62
uaauuucuac uaaguguaga ucguuuacuc ucguguuaaa aauc 44

<210> SEQ ID NO 63
<211> LENGTH: 44
<212> TYPE: RNA
<213> ORGANISM: Artificial Sequence
<220> FEATURE:
<223> OTHER INFORMATION: CoV2-S-cr10

<400> SEQUENCE: 63
uaauuucuac uaaguguaga uacuccuggu gauucuucuu cagg 44

<210> SEQ ID NO 64
<211> LENGTH: 44
<212> TYPE: RNA
<213> ORGANISM: Artificial Sequence
<220> FEATURE:
<223> OTHER INFORMATION: CoV2-M-cr1

<400> SEQUENCE: 64
uaauuucuac uaaguguaga uuagaagcgg ucuggucaga auag 44

<210> SEQ ID NO 65
<211> LENGTH: 44
<212> TYPE: RNA
<213> ORGANISM: Artificial Sequence
<220> FEATURE:
<223> OTHER INFORMATION: CoV2-M-cr2

<400> SEQUENCE: 65
uaauuucuac uaaguguaga uggcaggucc uugaugucac agcg 44

<210> SEQ ID NO 66
<211> LENGTH: 44
<212> TYPE: RNA
<213> ORGANISM: Artificial Sequence
<220> FEATURE:
<223> OTHER INFORMATION: CoV2-M-cr3

<400> SEQUENCE: 66
uaauuucuac uaaguguaga uuuuaggcag guccuugaug ucac 44

<210> SEQ ID NO 67
<211> LENGTH: 44
<212> TYPE: RNA
<213> ORGANISM: Artificial Sequence
<220> FEATURE:
<223> OTHER INFORMATION: CoV2-M-cr4

<400> SEQUENCE: 67
uaauuucuac uaaguguaga uuaauaagaa agcguucgug augu 44

<210> SEQ ID NO 68
<211> LENGTH: 44
<212> TYPE: RNA
<213> ORGANISM: Artificial Sequence
<220> FEATURE:
<223> OTHER INFORMATION: CoV2-M-cr5

<400> SEQUENCE: 68
uaauuucuac uaaguguaga uuuauuacaa auugggagcu ucgc 44

<210> SEQ ID NO 69
<211> LENGTH: 44
<212> TYPE: RNA
<213> ORGANISM: Artificial Sequence
<220> FEATURE:
<223> OTHER INFORMATION: CoV2-N-cr1

<400> SEQUENCE: 69
uaauuucuac uaaguguaga uuugaacugu ugcgacuacg ugau 44

<210> SEQ ID NO 70
<211> LENGTH: 44
<212> TYPE: RNA
<213> ORGANISM: Artificial Sequence
<220> FEATURE:
<223> OTHER INFORMATION: CoV2-N-cr2

<400> SEQUENCE: 70
uaauuucuac uaaguguaga ucugcugcuu gacagauuga acca 44

<210> SEQ ID NO 71
<211> LENGTH: 44
<212> TYPE: RNA
<213> ORGANISM: Artificial Sequence
<220> FEATURE:
<223> OTHER INFORMATION: CoV2-N-cr3

<400> SEQUENCE: 71
uaauuucuac uaaguguaga ucucucaagc ugguucaauc uguc 44

<210> SEQ ID NO 72
<211> LENGTH: 44
<212> TYPE: RNA
<213> ORGANISM: Artificial Sequence
<220> FEATURE:
<223> OTHER INFORMATION: CoV2-N-cr4

<400> SEQUENCE: 72
uaauuucuac uaaguguaga ugccuuguug uuguuggccu uuac 44

<210> SEQ ID NO 73
<211> LENGTH: 32
<212> TYPE: DNA
<213> ORGANISM: Artificial Sequence
<220> FEATURE:
<223> OTHER INFORMATION: CoV2-S- RPA-F

<400> SEQUENCE: 73
ggaaagtgag ttcagagttt attctagtgc ga 32

<210> SEQ ID NO 74
<211> LENGTH: 30
<212> TYPE: DNA
<213> ORGANISM: Artificial Sequence
<220> FEATURE:
<223> OTHER INFORMATION: CoV2-S- RPA-R

<400> SEQUENCE: 74
cacagtctac agcatctgta atggttccat 30

<210> SEQ ID NO 75
<211> LENGTH: 30
<212> TYPE: DNA
<213> ORGANISM: Artificial Sequence
<220> FEATURE:
<223> OTHER INFORMATION: CoV2-M- RPA-F

<400> SEQUENCE: 75
ctacttcatt gcttctttca gactgtttgc 30

<210> SEQ ID NO 76
<211> LENGTH: 30
<212> TYPE: DNA
<213> ORGANISM: Artificial Sequence
<220> FEATURE:
<223> OTHER INFORMATION: CoV2-M- RPA-R

<400> SEQUENCE: 76
ttatagttgc caatcctgta gcgactgtat 30

<210> SEQ ID NO 77
<211> LENGTH: 30
<212> TYPE: DNA
<213> ORGANISM: Artificial Sequence
<220> FEATURE:
<223> OTHER INFORMATION: CoV2-N- RPA-F

<400> SEQUENCE: 77
atcgtgctac aacttcctca aggaacaaca 30

<210> SEQ ID NO 78
<211> LENGTH: 30

<212> TYPE: DNA
<213> ORGANISM: Artificial Sequence
<220> FEATURE:
<223> OTHER INFORMATION: CoV2-N- RPA-R

<400> SEQUENCE: 78
gcaatttgcg gccaatgttt gtaatcagtt 30

<210> SEQ ID NO 79
<211> LENGTH: 416
<212> TYPE: DNA
<213> ORGANISM: Artificial Sequence
<220> FEATURE:
<223> OTHER INFORMATION: SARS-CoV2-S-

<400> SEQUENCE: 79
ggaaagtgag ttcagagttt attctagtgc gaataattgc acttttgaat atgtctctca 60
gccttttctt atggaccttg aaggaaaaca gggtaatttc aaaaatctta gggaatttgt 120
gtttaagaat attgatggtt attttaaaat atattctaag cacacgccta ttaatttagt 180
gcgtgatctc cctcagggtt tttcggcttt agaaccattg gtagatttgc caataggtat 240
taacatcact aggtttcaaa ctttacttgc tttacataga agttatttga ctcctggtga 300
ttcttcttca ggttggacag ctggtgctgc agcttattat gtgggttatc ttcaacctag 360
gacttttcta ttaaaatata atgaaaatgg aaccattaca gatgctgtag actgtg 416

<210> SEQ ID NO 80
<211> LENGTH: 333
<212> TYPE: DNA
<213> ORGANISM: Artificial Sequence
<220> FEATURE:
<223> OTHER INFORMATION: SARS-CoV2-M-

<400> SEQUENCE: 80
ctacttcatt gcttctttca gactgtttgc gcgtacgcgt tccatgtggt cattcaatcc 60
agaaactaac attcttctca acgtgccact ccatggcact attctgacca gaccgcttct 120
agaaagtgaa ctcgtaatcg gagctgtgat ccttcgtgga catcttcgta ttgctggaca 180
ccatctagga cgctgtgaca tcaaggacct gcctaaagaa atcactgttg ctacatcacg 240
aacgctttct tattacaaat tgggagcttc gcagcgtgta gcaggtgact caggttttgc 300
tgcatacagt cgctacagga ttggcaacta taa 333

<210> SEQ ID NO 81
<211> LENGTH: 446
<212> TYPE: DNA
<213> ORGANISM: Artificial Sequence
<220> FEATURE:
<223> OTHER INFORMATION: SARS-CoV2-N-

<400> SEQUENCE: 81
atcgtgctac aacttcctca aggaacaaca ttgccaaaag gcttctacgc agaagggagc 60
agaggcggca gtcaagcctc ttctcgttcc tcatcacgta gtcgcaacag ttcaagaaat 120
tcaactccag gcagcagtag gggaacttct cctgctagaa tggctggcaa tggcggtgat 180
gctgctcttg ctttgctgct gcttgacaga ttgaaccagc ttgagagcaa aatgtctggt 240
aaaggccaac aacaacaagg ccaaactgtc actaagaaat ctgctgctga ggcttctaag 300
aagcctcggc aaaaacgtac tgccactaaa gcatacaatg taacacaagc tttcggcaga 360

-continued

```
cgtggtccag aacaaaccca aggaaatttt ggggaccagg aactaatcag acaaggaact    420

gattacaaac attggccgca aattgc                                          446
```